US008541532B2

(12) United States Patent
Sugioka

(10) Patent No.: US 8,541,532 B2
(45) Date of Patent: Sep. 24, 2013

(54) SILANE COMPOUND, PRODUCTION METHOD THEREOF, AND RESIN COMPOSITION CONTAINING SILANE COMPOUND

(75) Inventor: Takuo Sugioka, Nishinomiya (JP)

(73) Assignee: Nippon Shokubai Co., Ltd., Osaka (JP)

( * ) Notice: Subject to any disclaimer, the term of this patent is extended or adjusted under 35 U.S.C. 154(b) by 455 days.

(21) Appl. No.: 12/526,002

(22) PCT Filed: Feb. 7, 2008

(86) PCT No.: PCT/JP2008/052480
§ 371 (c)(1),
(2), (4) Date: Nov. 5, 2009

(87) PCT Pub. No.: WO2008/099904
PCT Pub. Date: Aug. 21, 2008

(65) Prior Publication Data
US 2010/0317774 A1     Dec. 16, 2010

(30) Foreign Application Priority Data

| Feb. 9, 2007 | (JP) | 2007-031177 |
| May 15, 2007 | (JP) | 2007-129633 |
| Jun. 5, 2007 | (JP) | 2007-149576 |
| Oct. 18, 2007 | (JP) | 2007-271791 |

(51) Int. Cl.
*C08G 77/26* (2006.01)
*C08F 283/12* (2006.01)

(52) U.S. Cl.
USPC .............. 528/27; 528/26; 528/28; 525/474

(58) Field of Classification Search
USPC ................. 525/474; 528/26, 27, 28
See application file for complete search history.

(56) References Cited

U.S. PATENT DOCUMENTS

| 4,271,074 A | 6/1981 | Lohmann et al. |
| 4,364,808 A | 12/1982 | Lohmann et al. |
| 4,565,873 A | 1/1986 | Lohmann et al. |
| 5,879,436 A | 3/1999 | Kramer et al. |
| 6,268,457 B1 | 7/2001 | Kennedy et al. |
| 6,365,765 B1 | 4/2002 | Baldwin et al. |
| 6,387,590 B1 | 5/2002 | Mizutani et al. |
| 6,506,497 B1 | 1/2003 | Kennedy et al. |
| 2002/0055000 A1 | 5/2002 | Kennedy et al. |
| 2002/0095018 A1 | 7/2002 | Baldwin et al. |
| 2002/0106581 A1 | 8/2002 | Mizutani et al. |
| 2002/0128388 A1 | 9/2002 | Kennedy et al. |
| 2003/0120018 A1 | 6/2003 | Baldwin et al. |
| 2005/0058929 A1 | 3/2005 | Kennedy et al. |
| 2005/0112382 A1* | 5/2005 | Allen et al. ................. 428/447 |
| 2005/0192409 A1* | 9/2005 | Rhodes et al. ............. 525/326.7 |
| 2005/0245717 A1 | 11/2005 | Kennedy et al. |
| 2006/0009578 A1 | 1/2006 | Dershem |
| 2006/0189779 A1* | 8/2006 | Allen et al. ..................... 528/40 |
| 2007/0022909 A1 | 2/2007 | Kennedy et al. |
| 2008/0029739 A1 | 2/2008 | Jeganathan et al. |
| 2008/0210948 A1 | 9/2008 | Sugawara et al. |

FOREIGN PATENT DOCUMENTS

| JP | 63-146891 | 6/1988 |
| JP | 63-174967 A | 7/1988 |
| JP | 09-279034 A | 10/1997 |
| JP | 11-508927 | 8/1999 |
| JP | 2001-100417 A | 4/2001 |
| JP | 2001-100418 A | 4/2001 |
| JP | 2001-206926 A | 7/2001 |
| JP | 2002-069084 A | 3/2002 |
| JP | 2003-0502449 | 1/2003 |
| JP | 2003-217915 A | 7/2003 |
| JP | 2003-217916 A | 7/2003 |
| JP | 2005-120333 A | 5/2005 |
| JP | 2006-045392 A | 2/2006 |
| JP | 2006-073950 A | 3/2006 |
| JP | 2007-031321 A | 2/2007 |
| JP | 2008-009406 A | 1/2008 |

OTHER PUBLICATIONS

POSS Handbook. Polyhedral oligomeric silsesquioxane handbook. Phantom Plastics. 2010. Evidentiary Reference.*
M.C. Gravel, et al., Octa (3-Chloroammoniumpropyl) Octasilsesquioxane, Applied Organometallic Chemistry, 1999, vol. 13, No. 4, pp. 329-336, Scheme 7.
"Jikken Kagaku Kouza No. 22; Yuki Gosei IV—acid, amino acid, peptide—", 4th edition, edited by The Chemical Society of Japan, Maruzen Co., Ltd., 1992, p. 168.

* cited by examiner

*Primary Examiner* — Mike M Dollinger
(74) *Attorney, Agent, or Firm* — Novak Druce Connolly Bove + Quigg LLP

(57) ABSTRACT

A siloxane compound comprising a structure unit formed by connecting at least one organic skeleton having an imido bond to a silicon atom forming a siloxane bond, wherein the silane compound is defined by the following average formula: $X_a Y_b Z_c SiO_d$. X denotes groups including an organic skeleton having an imido bond, represented by formula (1) in the specification; Z denotes an organic groups having no imido bond; Y denotes at least one of hydrogen, hydroxyl, halogen, and OR; R denotes at least one of alkyl, acyl, aryl, and unsaturated aliphatic residual groups and may have a substituent; a is $\leq 3$ and $>0$; b is $0 \leq 3$; c is $0 \leq 3$; d is $\leq 2$ and $>0$; and $a+b+c+2d=4$, $R^1$ denotes at least one from aromatic, heterocyclic, and alicyclic rings; x and z independently $\geq 0$ and $\leq 5$; and y is 0 or 1.

7 Claims, No Drawings

US 8,541,532 B2

SILANE COMPOUND, PRODUCTION METHOD THEREOF, AND RESIN COMPOSITION CONTAINING SILANE COMPOUND

CROSS REFERENCE TO RELATED APPLICATIONS

This application is a national phase of PCT/JP2008/0052480, filed on Feb. 7, 2008 which claims priority to JP 2007-031177 filed Feb. 9, 2007, JP 2007-129633 filed May 15, 2007, JP 2007-149576 filed Jun. 5, 2007 and JP 2007-271791 filed Oct. 18, 2007, the entire contents of all are hereby incorporated by reference.

TECHNICAL FIELD

The invention relates to a silane compound, its production method, and a resin composition containing a silane compound. More particularly, the invention relates to a silane compound useful for mounting uses, optical uses, optodevice uses, display device uses, mechanical part materials, electric and electronic part materials, thermosetting binder resin compositions for bond magnets, and so forth; a silane compound useful for their intermediates; a production method of the silane compound; and a resin composition containing the silane compound.

BACKGROUND ART

Silane compounds having a siloxane bond are compounds having at least one Si—O bond (siloxane bond) and include polysiloxanes (generally called as silicones) and polysilsesquioxanes and have been used widely as raw materials of various kinds of industrial products so far. Today, owing to the characteristics attributed to the siloxane bond, silane compounds have been employed for various uses. For example, they have been employed for various materials such as mounting uses, optodevice uses, display device uses, mechanical part, electric and electronic parts, automotive part materials, and so forth and optical materials such as optical fibers, optical waveguides, optical recording disks, optical films, substrates for displays, and so forth. In such uses, in order to reform or improve various characteristics of resins to be used, try and error have presently been repeated and silane compounds which can exhibit characteristics attributed to the siloxane bond have also been investigated for applications to those uses.

DISCLOSURE OF THE INVENTION

Problems to be Solved by the Invention

With respect to conventional silane compounds, the following were developed: novel compounds characterized in that they have a maleimido group and an alkoxysilyl group via a urethane bond (e.g. reference to Japanese Kokai Publication No. 2002-69084 on page 2, claim 1), silane compounds having an imido group (e.g. reference to Japanese Kokai Publication No. Sho-63-146891 on page 9), triethoxysilylpropyl-1,8-naphthalimides as organic absorption compounds (e.g. reference to Japanese Kohyo Publication No. 2003-502449 on page 2, claim 9), polynadic imidesiloxane precursors (e.g. reference to Japanese Kokai Publication No. Hei-09-279034 on page 5, paragraph 24), rod-like polysiloxanes having ammonium cation on the surfaces (e.g. reference to Japanese Kokai Publication No. 2006-45392 on page 2), and layered polyaminoalkylsiloxane composites (e.g. reference to Japanese Kokai Publication No. 2005-120333 on pages 2 to 4). However, there is still room for improvement to give compounds excellent in various functions and capable of exhibiting sufficient functions for heat resistance or the like for preferable usability in fields where further developments are strongly desired for mounting uses.

Various kinds of materials such as mechanical part materials, electric and electronic part materials, and automotive part materials have been required to be materials which can be durable for uses under severe conditions in addition to high functionality of products. For instance, there are wide gap semiconductors such as silicon carbide (SiC) and gallium nitride (GaN) as new semiconductor materials. As compared with silicon (Si) type semiconductor devices of conventional technology, while having high operation upper limit temperature, high pressure resistance, mechanical and chemical stability, and high heat conductivity, these semiconductor materials are easy for adding (doping) impurities and have many analogous points in process for fabricating Si semiconductor devices and accordingly, it has been recognized that a technical hurdle for fabricating device products is low for these semiconductor materials and use of these semiconductor materials for substrates of power semiconductor devices makes it possible to actualize high pressure resistance, low electric power loss, and high operational temperature and reduce the power loss of semiconductor devices by half. Therefore, use of these semiconductor materials for rectifying elements, switching electric power IC for domestic appliances and PC, motor-driven IC for electric vehicles, and inverter IC has been promoted.

Particularly in these years, electric vehicles and hybrid cars come to the forefront and along with the tendency, car electronization has drastically been carried out and it has been required strongly to unit various kinds of electronic control units, actuators, sensors, and communication IC and dispose them in high temperature environments near engines and transmissions in order to keep wide interior spaces and leave wide options of layout of vehicular interiors. Further, in terms of the safety for drivers and users for vehicular uses, suppression of erroneous operation is more severely required than that for uses for domestic electric appliances. Therefore, as plastic materials for mechanical parts, electric and electronic parts, and automotive parts have been desired plastic materials which are less deteriorated in various physical properties in a higher temperature range than before.

Conventionally, epoxy type materials have generally been employed in such fields and if being left for a long time at a temperature as high as, for example, 200° C. or higher, these materials are found considerably losing weight and deteriorated in mechanical strength and therefore heat resistance improvement is required. There are engineering plastics such as polyimides as high heat resistant materials, however, the plastics are inferior in handling property and difficult to have the workability as good as that of epoxy materials and therefore their use is limited to flexible substrates or the like. Accordingly, it is required for the materials to suppress weight loss, have improved heat resistance, actualize excellent workability, and be usable for various uses.

Further, various kinds of polysiloxanes/polysilsesquioxanes or nanocomposite materials are exemplified as organic-inorganic hybrid materials, however, these materials are, as a whole, insufficient in heat resistance improvement or costly since they require to contain noble metal catalysts at the time of use even if they have excellent heat resistance and therefore these materials are unsuitable for uses for mass consumption such as automobiles (e.g. reference to Japanese Kokai Publication No. 2006-73950 on pages 2 to 4).

The bond magnet generally means a magnet produced by molding a resin composition which includes a magnetic substance such as ferrite, Alnico alloy, and rare earth, and a binder as a matrix for the magnetic substance. Such a bond magnet is easily molded in comparison to a conventional magnet generally produced by a sintering method, and can be molded into a complicate shape with a high accuracy. Therefore, use of such a bond magnet has been rapidly stored in various applications. For example, the bond magnet has been used in various products and components such as automobiles, common electric appliances, communication facilities, and audio equipment, medical equipment, and common industrial equipment.

The bond magnet is generally produced by curing and molding a mixture of a magnetic substance and a binder resin through a heat molding step such as an injection molding and an extrusion molding. In such a case, the mixture is exposed to a high temperature of 200° C. to 300° C. in the injection molding, for example. In addition, the magnet bond recently needs to be operated at a high temperature of 200° C. or more if used in a motor for electric vehicles. Under such a situation, there is a technical problem in that the magnet surface is oxidized and covered with an oxide and such heat history reduces a coercive force of the magnetic substance.

With respect to a conventional resin composition for a magnet bond, for example, Japanese Kokai Publication No. 2001-206926 on pages 1 and 2 proposes a resin composition which can be cured at a low temperature without being exposed to a high temperature during a molding process. The resin composition is a rare earth composition for a bond magnet which includes (A) a binder resin composed of a polymerizable compound obtained vinyl-esterifying 50% or more and less than 100% of epoxy groups in an epoxy compound, with unsaturated monobasic acid, (B) a thermal polymerization initiator, and (C) rare earth alloy powders. Further, for example, Japanese Kokai Publication No. 2003-217915 on page 2 discloses a high weather resistant magnet powder including a phosphate coating (B1) of 5 to 10 nm for the average film thickness and a phosphate coating (B2) of 5 to 100 nm for the average film thickness on the surface of a magnet powder (A) consisting of an iron magnet alloy powder containing a rare earth element, wherein an iron/rare earth element ratio of the phosphate coating (B1) is equal to or larger than 5 and smaller than 8, and an iron/rare earth element ratio of the phosphate coating (B2) is equal to or larger than 8. In addition, Japanese Kohyo Publication No. 2003-217916 on page 2 discloses a high heat resistance magnet powder, in which a copper coating (B1) of 1 to 10 nm for the average film thickness and an inorganic phosphate coating (B2) of 5 to 10 nm for the average film thickness are successively formed on the surface of a magnet powder (A) consisting of a transition metal magnet alloy powder containing a rare earth element. It has been tried to form a phosphorus coating on the magnet powder surface, thereby suppressing the oxidization of the bond magnet surface during the molding process from deteriorating the magnetic characteristics. However, the performances need to be further improved in order to sufficiently solve the problems such as heat resistance of a conventional bond magnet. Such a conventional bond magnet has room improvement in order to be preferably used in a field in which development has been strongly desired, as well as in, applications where the bond magnet has been currently used.

Under the above-mentioned state of the art, the invention aims to provide a silane compound excellent in heat resistance, pressure resistance, mechanical and chemical stability, and heat conductivity and advantageously usable for mounting uses in form of a resin composition capable of forming cured materials with scarce deterioration of various physical properties even if a large share force is applied to the resin composition or even under severe environments such as high temperature and high pressure, its production method, and a resin composition containing such a silane compound.

Means for Solving the Problems

The inventors have made various investigations on a silane compound and have found a silane compound having an organic skeleton having an imido bond and an amido bond and forming a siloxane skeleton by silicon atoms bonding the organic skeleton via oxygen atoms. The inventors have found that it is possible for a resin composition containing the compound and an organic resin to exhibit excellent heat resistance without losing the excellent characteristics which the organic resin has such as lightweight of products, capability of making products compact, formability, and flexibility and accordingly solve the above-mentioned aim. Further, the inventors have found that a resin composition containing such a silane compound and an organic resin is particularly advantageously usable for mounting uses for various kinds of materials, for instance, mechanical part materials, electric and electronic part materials, automotive part materials, and thermosetting resin compositions for bond magnets. In addition, the inventors have found also a method for efficiently producing a silane compound having such a specified structure and finally have accomplished the invention.

That is, the invention provides a silane compound having a siloxane bond and an imido bond, wherein the silane compound includes a structure unit formed by connecting at least one organic skeleton having an imido bond to a silicon atom forming a siloxane bond, wherein the silane compound is defined by the following average composition formula:

X$_a$Y$_b$Z$_c$SiO$_d$ in the formula,

X may be same or different and denotes a group including an organic skeleton having an imido bond, represented by the following formula (1); Z may be same or different and denotes an organic group having no imido bond; Y may be same or different and denotes at least one selected from the group consisting of hydrogen atom, hydroxyl group, halogen atom, and OR group; R may be same or different and denotes at least one selected from the group consisting of alkyl, acyl, aryl, and unsaturated aliphatic residual groups and may have a substituent; a is a numeral of 3 or lower but not 0; b is 0 or a numeral less than 3; c is 0 or a numeral less than 3; d is a numeral less than 2 but not 0; and a+b+c+2d=4,

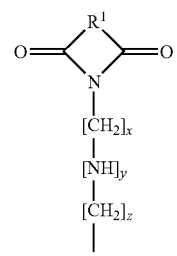

(1)

in the formula, R$^1$ denotes at least one structure selected from the group consisting of aromatic, heterocyclic, and alicyclic rings; x and z may be same or different and independently denote an integer of 0 or higher and 5 or lower; and y is 0 or 1.

Hereinafter, the invention will be described in detail.

A silane compound of the invention has a structure unit (hereinafter, referred to also as structure unit (I)) formed by connecting at least one organic skeleton having an imido bond to a silicon atom and a siloxane bond (siloxane skeleton). Since the above-mentioned silane compound (referred to also as silane compound (i)) has such a structure, the silane compound is excellent in heat resistance, pressure resistance, mechanical and chemical stability, and heat conductivity and capable of providing various characteristics such as heat resistance to various materials. For example, structures such as siloxane skeletons, organic skeletons having an imido bond, and the structure unit (I) may properly be selected to give a silane compound having high compatibility with various kinds of polymers and accordingly the polymers are easily provided with heat resistance and pressure resistance.

The polymers provided with heat resistance and pressure resistance can form cured articles with scarce deterioration of various physical properties even under severe environments such as high temperature and high pressure and are thus preferably usable for mounting uses. As described, the above-mentioned silane compound can be preferably usable for mechanical part materials, electric and electronic part materials, automotive part materials, civil engineering and construction materials, molding materials, and materials for coatings and adhesives and also for molding materials for electronic materials and materials for ink, coatings, varnish, and adhesives. Further, the above-mentioned silane compound can be used as a low dielectric material used in a semiconductor device and the like, or as a thermosetting resin composition for bond magnets. Especially, the compound is preferably usable for implementation fields such as most-advanced microprocessor unit (MPU) and vehicle mounting materials which are required to have higher thermal stability than conventional materials for domestic electric appliances.

In the above-mentioned silane compound (i), "organic skeleton having imido bond" is not particularly limited if the structure indispensably has an imido bond, however, it is preferably (1) a structure containing an imido structure and an alkylene group of 1 to 6 carbon atom(s), (2) a structure containing an imido structure and a secondary amino group, and (3) a structure containing an imido structure and a tertiary amino group. Especially, (1) a structure containing an imido structure and an alkylene group of 1 to 6 carbon atom(s) is more preferable since it gives a silane compound with high thermal stability.

In the above-mentioned silane compound (i), the ratio of the above-mentioned organic skeleton having an imido bond is preferably 20 to 100 mole based on 100 mole of silicon atom contained in the silane compound (i). It is more preferably 50 to 100 mole, and still more preferably 70 to 100 mole, and particularly preferably 100 to 80 mole, and most preferably 100 mole. According to this, the solubility of the silane compound to an organic resin as well as the heat resistance, the resistance to hydrolysis, and the like, can be improved.

Silicon atom attached to the above-mentioned organic skeleton having an imido bond is connected to at least one oxygen atom in addition to at least one organic skeleton having an imido bond and forms a siloxane skeleton through oxygen atom. That is, the silicon atom attached to the organic skeleton having an imido bond is connected to the organic skeleton having an imido bond, oxygen atom, and optionally other skeletons and the total of the bonds of the organic skeleton, oxygen atom, and other skeletons is 4 and both of the organic skeleton and oxygen atom are connected at least one each in number.

Other skeletons may include at least one selected from the group consisting of organic groups having no imido bond, hydrogen atom, hydroxyl group, halogen atom, and OR group. R may be same or different and denotes at least one selected from the group consisting of alkyl, acyl, aryl, and unsaturated aliphatic residual groups and may have a substituent. The organic groups having no imido group are preferably at least one selected from the group consisting of alkyl, aromatic residual groups such as aryl, and aralkyl and unsaturated aliphatic residual groups and these groups may have substituents. Particularly preferable examples are optionally substituted alkyl having 1 to 8 carbon atom(s), aromatic residual groups such as aryl, or aralkyl. These organic groups may have a substituent. Practical examples are methyl, ethyl, phenyl, vinyl, chloropropyl, mercaptopropyl, (epoxycyclohexyl)ethyl, glycidoxypropyl, N-phenyl-3-aminopropyl, (meth)acryloxypropyl, hexyl, decyl, octadecyl, and trifluoropropyl.

The number of the above-mentioned organic skeleton having an imido bond connected to silicon atom is 1 to 3, preferably 1 to 2, and more preferably 1. The number of oxygen atom to be connected (oxygen atom to be connected to the silicon atom attached to the organic skeleton having an imido bond) is 1 to 3, preferably 2 to 3, and more preferably 3. The number of other organic skeletons to be connected is 0 to 2, preferably 0 to 1, and more preferably 0. Preferable combinations (number of bonds) of the skeletons (groups) to be boned to silicon atom are (organic skeleton having an imido bond, oxygen atom, other skeletons) (1, 3, 0), (2, 2, 0), (1, 2, 1), (3, 1, 0), (2, 1, 1), and (1, 1, 2).

The above-mentioned silane compound (i) has a siloxane skeleton (referred to also as a main chain skeleton). The siloxane skeleton may include any skeletons if the skeletons indispensably have a siloxane bond, and the structure of the siloxane skeleton may be chain or branched and polysilsesquioxanes having a ladder, cage-like, or cubic structure are preferable.

The ratio of the siloxane skeleton in the above-mentioned silane compound (i) is preferably 10 to 80% by weight, more preferably 15 to 70% by weight, and even more preferably 20 to 50% by weight based on 100% by weight of the silane compound (i).

The above-mentioned silane compound (i) is not particularly limited if it has the above-mentioned structure, and examples of preferable embodiments may be (1) a silane compound having a siloxane bond and an imido bond, wherein the silane compound contains a main chain skeleton indispensably having a siloxane bond (a polysiloxane bond) and has a structure formed by connecting a structure indispensably containing an imido bond to the main chain skeleton; (2) a silane compound indispensably having a structure unit in which at least one organic skeleton having an imido bond is connected to silicon atom and at least one oxygen atom is connected to the above-mentioned silicon atom, wherein the above-mentioned silicon atom of the structure unit forms a siloxane skeleton through oxygen atom; (3) a silane compound having a main chain skeleton comprising a siloxane bond and an organic skeleton having an imido bond, wherein the silicon compound contains a structure unit formed by connecting some of silicon atoms of the main chain skeleton to the organic skeleton as an indispensable unit; and (4) a silane compound comprising a siloxane bond and an organic skeleton having an imido bond, wherein the silane compound has a main chain skeleton indispensably having a polysiloxane bond and the organic skeleton having an imido bond is connected to at least one silicon atom of the main chain skeleton.

In the above-mentioned preferable embodiment (1), "structure formed by connecting a structure indispensably containing an imido bond to the main chain skeleton" may include a structure formed by connecting at least one structure indispensably containing an imido bond (organic skeleton having an imido bond) to the main skeleton (siloxane skeleton) of the silane compound (i). That is, the structure may include a structure having the above-mentioned structure indispensably containing an imido bond besides the main chain skeleton. Practically, the above-mentioned silane compound (i) is preferably those having a structure indispensably containing an imido bond in a side chain. In this case, the structure indispensably containing an imido bond is not limited to those containing repeating units forming "chain"-like structure but those having at least one structure as a side chain.

In the above-mentioned preferable embodiment (2), "structure unit in which at least one organic skeleton having an imido bond is connected to silicon atom and at least one oxygen atom is connected to the silicon atom" is preferably defined by the following general formula:

in the formula, X denotes an organic skeleton having an imido bond; s is an integer of 1 to 3; 2t is an integer of 1 to 3; and s+2t=4.

The above-mentioned silane compound is preferable to be defined by the following average composition formula:

X$a$Y$b$Z$c$SiO$d$ in the formula,

X may be same or different and denotes an organic skeleton having an imido bond; Z may be same or different and denotes an organic skeleton having no imido bond; Y may be same or different and denotes at least one selected from the group consisting of hydrogen atom, hydroxyl group, halogen atom, and OR group; R may be same or different and denotes at least one selected from the group consisting of alkyl, acyl, aryl, and unsaturated aliphatic residual groups and may have a substituent; a is a numeral of 3 or lower but not 0; b is 0 or a numeral less than 3; c is 0 or a numeral less than 3; d is a numeral less than 2 but not 0; and a+b+c+2d=4. That is, the coefficient a for X is a numeral satisfying $0<x\leq3$; the coefficient b for Y is a numeral satisfying $0\leq y<3$; the coefficient c for Z is a numeral satisfying $0\leq z<3$; and the coefficient d for O is a numeral satisfying $0<d<2$. The above-mentioned formula (1) is mentioned below.

In the above-mentioned silane compound, if the proportion of the organic skeleton having an imide bond relative to the silicon atom is increased, the solubility of the silane compound to the organic resin can be improved. From viewpoint of the solubility to the organic resin, it is preferable that, in the average composition formula, a coefficient a for X satisfies 0.2 or more. If the coefficient a for X is that is an organic skeleton having an imido bond is less than 0.2, the solubility to the organic resin might be reduced. Therefore, if the above-mentioned silane compound is dissolved to an organic resin to form a resin composition, the resin composition might not sufficiently exhibit the characteristics attributed to the silane compound. The coefficient a for X is more preferably 0.5 or more, and still more preferably 0.7 or more, and particularly preferably 0.8 or more, and most preferably 1.0 or more. The coefficient a is preferably 1.0 or less in view of the heat resistance of the above-mentioned silane compound. If the coefficient a is more than 1.0, a functional group other than X is connected to Si, and therefore the heat resistance might be deteriorated. As mentioned above, it is preferable that the coefficient a for X satisfies 0.2 or more and 1.0 or less, in order to for the resin composition to have a more excellent heat resistance, an improved solubility to an organic resin, and an excellent resistance to hydrolysis. The coefficient a for X is more preferably 0.5 or more and 1.0 or less, and still more preferably 0.7 or more and 1.0 or less, and particularly preferably 0.8 or more and 1.0 or less, and most preferably is 1.0. In the above-mentioned average composition formula, a+b+c is preferably 0.5 or more, and more preferably 0.7 or more, and still more preferably 0.7 or more and 1.0 or less, and particularly preferably 1. The coefficient d for oxygen is preferably 1.50.

It is preferable in the silane compound that a ratio of a silanol group amount, calculated by the following formula (α), is 0.1 or less.

[molar number of Si—OH bond]/[molar number of Si—O bond]   (α)

According to this, the composition including the above-mentioned silane compound has a significantly low viscosity. In addition, the composition and a cured article thereof can obtain an extremely excellent resistance to moisture absorption. The silanol group amount calculated from the above formula (α) is more preferably 0.05 or less and still more preferably 0.01 or less. Particularly preferably, the above-mentioned silane compound has no remaining silanol groups. Herein, the molar number of Si—OH bond means the number of bonds between Si and OH, represented by the molar number. For example, if two OH groups are connected to each Si atom per mole, the molar number of Si—OH bond is 2. In the same manner, the molar number of Si—O bond is also calculated.

In the above-mentioned average composition formula: X$_a$Y$_b$Z$_c$SiO$_d$: Y is preferably hydroxyl group or OR group. Y is more preferably OR group and even more preferably OR group in which R is an alkyl having 1 to 8 carbon atom(s). Further, Z is preferably one selected from the group consisting of aromatic residual groups such as alkyl, aryl, and aralkyl and unsaturated aliphatic residual groups. They may have substituents. Z is more preferably optionally substituted aromatic residual groups such as alkyl having 1 to 8 carbon atom(s), aryl, or aralkyl.

The above-mentioned silane compound is, for example, defined as follows:

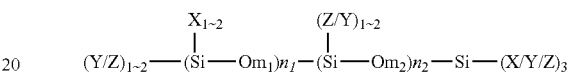

in the formula, X, Y, and Z may be independently same or different and same as described above; $n_1$ and $n_2$ denote polymerization degree, and $n_1$ is a positive integer but not 0 and $n_2$ is 0 or a positive integer. In this connection, Y/Z—expresses that Y or Z is connected: $X_{1-2}$—expresses that 1 or 2 X groups are connected: $(Z/Y)_{1-2}$—expresses that 1 of Z or Y group is connected, or 2 of Z or Y groups are connected, or each one of Z and Y groups in total 2 groups are connected: and Si—(X/Y/Z)$_3$ expresses that arbitrary three of X, Y, and Z groups are connected to silicon atom. In the above-mentioned formula, Si-Om$_1$ and Si-Om$_2$ do not define the bonding order of Si-Om$_1$ and Si-Om$_2$ but preferably define, for example, the reciprocal or random copolycondensation state of Si-Om$_1$ and Si-Om$_2$ and the bonding state of polysiloxane of Si-Om$_1$ and polysiloxane of Si-Om$_2$, and the condensation structure is arbitrary.

The above-mentioned silane compound can be defined by the above-mentioned average composition formula: X$_a$Y$_b$Z$_c$-SiO$_d$: and the siloxane skeleton of the silane compound (main chain structure indispensably having a siloxane bond) may be defined as (SiO$_m$)$_n$. The structure other than (SiO$_m$)$_n$ includes the organic skeleton having an imido bond (the structure indispensably having an imido bond) for X; hydrogen atom, hydroxyl group, or the like for Y; and organic group having no imido bond for Z and they are connected to silicon atom. X, Y, and Z may or may not be contained in a repeating unit formed in "chain". For example, X may be contained at least one as a side chain in a single molecule. In the above-mentioned (SiO$_m$)$_n$, n denotes the polymerization degree and it expresses that the polymerization degree of the main chain skeleton and the organic skeleton having an imido bond is not necessarily required to exist n in number. In other word, the organic skeleton having an imido bond is not necessarily required to exist one by one for each (SiO$_m$)$_n$. Further, the organic skeleton having an imido bond may exist one or more in one molecule and in the case a plurality of organic skeletons having an imido bond are contained, as described above, two or more organic skeletons having an imido bond may be connected to one silicon atom.

In the above-mentioned main skeleton (SiO$_m$)$_n$, m is preferably a numeral of 1.0 or higher and less than 2.0, and more preferably m=1.5 to 1.8, and particularly preferably m=1.5. In the above-mentioned main chain skeleton (SiO$_{m1}$)$_{n1}$ and (SiO$_{m2}$)$_{n2}$, it is preferable that the range of $(n_1+1)/(n_1+n_2+1)$ is the same as the preferable range of the a in the above average composition formula X$a$Y$b$Z$c$SiO$d$. Further, it is preferable that the number of X connected to the Si atom connected to (X/Y/Z)$_3$ in the above formula and the Si atom in (SiO$_{m1}$) is 1.

The above-mentioned reference character n denotes the polymerization degree and is preferably 1 to 5000. It is more preferably 1 to 2000, furthermore preferably 1 to 1000, and even more preferably n=1 to 200.

The silane compound in the case n is 2 may include those containing two structure units (structure unit (I)) formed by connecting at least one organic skeleton having an imido bond to silicon atom and those containing only one structure unit. Practical examples are as follows:

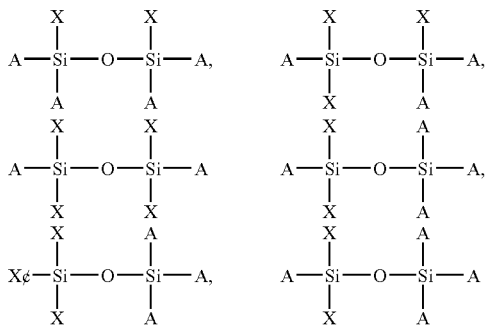

in the formula, A denotes Y or Z; and X, Y, and Z are same as described above and may include those having a homopolymer structure containing two same structure units (I), those having a homopolymer structure containing two different structure units (I), and those having a copolymer structure (copolycondensation structure) containing only one structure unit (I).

The silane compound of the invention (silane compound (i)) has the above-mentioned structure, and X in the above-mentioned average composition formula of the silane compound is defined by the above-mentioned formula (1).

The "X in the above-mentioned average composition formula of the silane compound is defined by the above-mentioned formula (1)" means "a silane compound having an average composition formula in which X in the above-mentioned average composition formula: $X_aY_bZ_cSiO_d$: (Z, Y, a, b, c, and d are as described above) is defined by the formula (1). Hereinafter, it is the same for the following formula (2).

In the above-mentioned $R^1$, at least one structure selected from the group consisting of aromatic, heterocyclic, and alicyclic rings means that $R^1$ denotes at least one selected from the group consisting of groups having ring structures of aromatic moieties (aromatic rings), groups having ring structures of heterocyclic moieties (hetero rings), and groups having ring structures of alicyclic moieties (alicyclic rings). $R^1$ is preferably phenylene group, naphthylidene group, divalent group of norbornene, (alkyl)cyclohexylene group, and cyclohexenyl group. In the case $R^1$ is phenylene group, a silane compound in which the above-mentioned X is defined by the following formula (2) is obtained: in the case $R^1$ is (alkyl)cyclohexylene group, a silane compound in which the above-mentioned X is defined by the following formula (3) is obtained: in the case $R^1$ is naphthylidene group, a silane compound in which the above-mentioned X is defined by the following formula (4) is obtained: in the case $R^1$ is divalent norbornene group, a silane compound in which the above-mentioned X is defined by the following formula (5) is obtained: and in the case $R^1$ is cyclohexenyl group, a silane compound in which the above-mentioned X is defined by the following formula (6) is obtained.

In the above-mentioned formula (1), x and z may be same or different and independently denote an integer of 0 or higher and 5 or lower.

Additionally, x+z may be an integer of 0 or higher and 10 or lower, preferably 3 to 7, more preferably 3 to 5, and even more preferably 3.

The above-mentioned y is 0 or 1 and preferably 0.

The above-mentioned silane compound (1) can be used preferably for application described in the above-mentioned silane compound (i) and particularly preferably employed for implementation fields such as most advanced MPU and vehicle mounting materials which are required to have higher thermal stability than conventional materials for domestic electric appliances. Further, the above-mentioned silane compound (1) has a very high heat resistance and high compatibility with various kinds of polymers, so that it can easily provide heat resistance. Practically, in the case the silane compound is added to various kinds of materials such as aromatic plastics to improve the heat resistance, it is not necessary to employ a conventional addition method for silicone compounds of adding and dispersing the silane compound to and in the materials later and for example, the silane compound may be added previously to raw materials of various kinds of polymers and the raw materials are reacted to obtain various kinds of polymers, so that the silane compound can be more evenly mixed and provide excellent heat resistance. In such a manner, if the above-mentioned silane compound (1) is added to heat resistant aromatic plastics, the heat resistance is further improved and the plastics can be employed preferably for the above-mentioned uses.

The silane compound (i) defined by the above-mentioned average composition formula $X_aY_bZ_cSiO_d$ can be produced by any method, however, it is preferable to obtain the silane compound by the following production methods (a) and (b). (a) A production method involving imidizing an intermediate defined by an average composition formula $X'_aY_bZ_cSiO_d$ (silane compound) having an organic skeleton X' having an amido bond corresponding to the organic skeleton X having an imido bond in the above-mentioned silane compound (i) and a siloxane bond and (b) a production method involving hydrolyzing and condensing an intermediate of a silane compound in which an organic skeleton having an amido bond corresponding to the organic skeleton X having an imido bond in the above-mentioned silane compound (i) is connected to silicon atom and which has hydrolyzable group.

The above-mentioned silane compound (1) is preferable to be obtained by a production method involving imidizing an intermediate composed of a silane compound defined by an average composition formula $X'_aY_bZ_cSiO_d$ (X' denotes an organic skeleton having an amido bond; and others are same as those of the above-mentioned average composition formula) in which X' is defined by the following formula (8) or a production method involving a step of hydrolyzing and polycondensing an intermediate composed of a silane compound defined by the following formula (10). These production methods will be described later.

The above-mentioned silane compound is preferably a silane compound (referred to also as silane compound (2)) (in the silane compound (i) or (1)), X in the above-mentioned average composition formula of the silane compound is defined by the following formula (2):

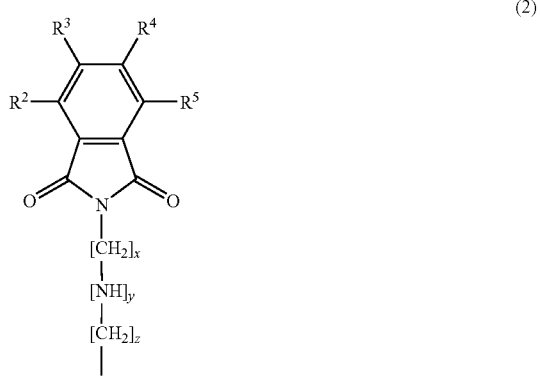

(2)

in the formula, $R^2$ to $R^5$ may be same or different and independently denote at least one selected from the group consisting of hydrogen atom, alkyl group, halogen atom, or aromatic groups; x and z may be same or different and independently denote an integer of 0 or higher and 5 or lower; and y is 0 or 1).

The above-mentioned $R^2$ to $R^5$ are preferably all hydrogen atoms.

The above-mentioned x, y, and z are preferable to be the same as described above.

The above-mentioned silane compound is preferably a silane compound (referred to also as silane compound (3)) (in the silane compound (i) or (1)), X in the above-mentioned average composition formula of the silane compound is defined by the following formula (3):

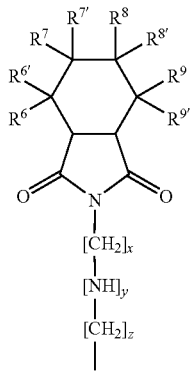

(3)

in the formula, $R^6$ to $R^9$ and $R^{6'}$ to $R^{9'}$ may be same or different and independently denote at least one selected from the group consisting of hydrogen atom, alkyl group, halogen atom, or aromatic groups; x and z may be same or different and independently denote an integer of 0 or higher and 5 or lower; and y is 0 or 1).

With respect to the above-mentioned $R^6$ to $R^9$ and $R^{6'}$ to $R^{9'}$, it is preferable that $R^7$ or $R^8$ is methyl group and the remaining are all hydrogen atoms, or that $R^6$ to $R^9$ and $R^{6'}$ to $R^{9'}$ are all hydrogen atoms, or that $R^6$ to $R^9$ and $R^{6'}$ to $R^{9'}$ are all fluorine atoms. It is more preferably that $R^7$ or $R^8$ is methyl and the remaining is all hydrogen atoms.

The above-mentioned x, y, and z are preferable to be the same as described above.

The above-mentioned silane compound is preferably a silane compound (referred to also as silane compound (4)) (in the silane compound (i) or (1)), X in the above-mentioned average composition formula of the silane compound is defined by the following formula (4):

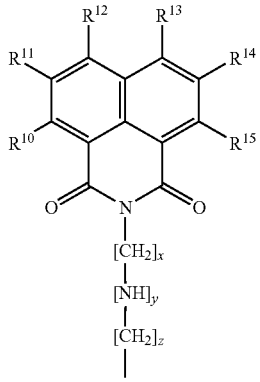

(4)

in the formula, $R^{10}$ to $R^{15}$ may be same or different and independently denote at least one selected from the group consisting of hydrogen atom, alkyl group, halogen atom, or aromatic groups; x and z may be same or different and independently denote an integer of 0 or higher and 5 or lower; and y is 0 or 1).

With respect to the above-mentioned $R^{10}$ to $R^{15}$, it is preferable that $R^{10}$ to $R^{15}$ are all hydrogen atoms or that $R^{10}$ to $R^{15}$ are all fluorine atoms. It is more preferably that $R^{10}$ to $R^{15}$ are all hydrogen atoms.

The above-mentioned x, y, and z are preferable to be the same as described above.

The above-mentioned silane compound is preferably a silane compound (referred to also as silane compound (5)) (in the silane compound (i) or (1)), X in the above-mentioned average composition formula of the silane compound is defined by the following formula (5):

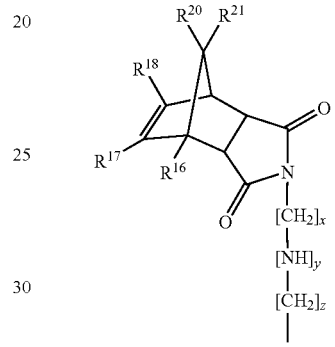

(5)

in the formula, $R^{16}$ to $R^{21}$ may be same or different and independently denote at least one selected from the group consisting of hydrogen atom, alkyl group, halogen atom, or aromatic groups; x and z may be same or different and independently denote an integer of 0 or higher and 5 or lower; and y is 0 or 1).

With respect to the above-mentioned $R^{16}$ to $R^{21}$, it is preferable that $R^{16}$ to $R^{21}$ are all hydrogen atoms or that $R^{16}$ to $R^{21}$ are all fluorine atoms. It is more preferably that $R^{16}$ to $R^{21}$ are all hydrogen atoms.

The above-mentioned x, y, and z are preferable to be the same as described above.

The above-mentioned silane compound is preferably a silane compound (referred to also as silane compound (6)) (in the silane compound (i) or (1)), X in the above-mentioned average composition formula of the silane compound is defined by the following formula (6):

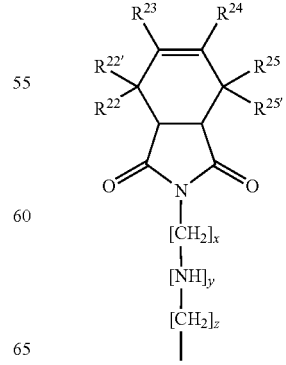

(6)

in the formula, $R^{22}$ to $R^{25}$ and $R^{22'}$ to $R^{25'}$ may be same or different and independently denote at least one selected from the group consisting of hydrogen atom, alkyl group, halogen atom, or aromatic groups; x and z may be same or different and independently denote an integer of 0 or higher and 5 or lower; and y is 0 or 1).

With respect to the above-mentioned $R^{22}$ to $R^{25}$ and $R^{22'}$ to $R^{25'}$, it is preferable that $R^{22}$ to $R^{25}$ and $R^{22'}$ to $R^{25'}$ are all hydrogen atoms, or that $R^{22}$ to $R^{25}$ and $R^{22'}$ to $R^{25'}$ are all fluorine atoms, or that $R^{22}$ to $R^{25}$ and $R^{22'}$ to $R^{25'}$ are all chlorine atoms. It is more preferably that all are hydrogen atoms.

The above-mentioned x, y, and z are preferable to be the same as described above.

The above-mentioned silane compounds (5) and (6) each include an unsaturated bond inside the molecule and form a cross-linking structure through the same mechanism as in the below-mentioned maleimide compound. Therefore, if a maleimide compound is mixed with each of the silane compounds (5) and (6), the mixture can be used as the resin composition, and shows excellent low-dielectric characteristics particularly because the cross-linking structure is a saturated ring structure and generates no polar groups after the crosslinking. That is, it is preferable that the resin composition is a resin composition for low dielectric materials. The compound (5) is preferable as the silane compound. The mixing ratio of the silane compound to the above-mentioned maleimide is 10/90 to 90/10, and more preferably 15/85 to 85/15, and still more preferably 20/80 to 80/20, base on the ratio of the unsaturated bond equivalent.

Preferable examples of the application of the above-mentioned resin composition for low dielectric materials include a printed-circuit board for a high-speed computer or a high-speed communication facility, an antenna for wireless communications, used for Wi-Fi, WiMAX, Bluetooth, RF tag and the like, a printed-circuit board for satellite broadcasting converters, a board for semiconductor packages, and a memory card. If the above-mentioned resin composition including the silane compound and the organic resin is used as a low dielectric material in such an application, a parasitic capacitance generated between electrodes forming an electronic device can be suppressed, for example. As a result, response characteristics can be improved and heat generation can be suppressed in the electronic device.

It is preferable that the above-mentioned resin composition for low dielectric materials has a relative dielectric constant of 3.4 or less at a measuring frequency of 1 GHz or 5 GHz. The relative dielectric constant is more preferably 3.2 or less and still more preferably 3.1 or less. It is preferable that the resin composition for low-dielectric materials has a dielectric loss tangent of 0.02 or less at a measuring frequency of 1 GHz or 5 GHz. The dielectric loss tangent is more preferably 0.01 or less and still more preferably 0.009 or less. Thus, if the resin composition for a low dielectric material has a small relative dielectric constant or a small dielectric loss tangent, such a resin composition can exhibit excellent characteristics used in the above-mentioned applications.

If the above-mentioned resin composition is a resin composition for low dielectric materials, it is preferable that the resin composition includes a silane compound and a maleimide compound. According to this, a value of the dielectric loss tangent can be decreased. Therefore, in the electronic device used in the board for a semiconductor package and the like, the response characteristics can be improved, or the heat generation can be suppressed. Further, the above-mentioned resin composition may include another compound, in addition to the silane compound and the maleimide compound. For example, an epoxy compound, a phenol compound, and the like, may be included. If the resin composition at least one of the epoxy resin and the phenol resin, the dielethe dielectric constant of the resin composition can be reduced, and thereby such a resin composition can exhibit more excellent characteristics as the resin composition for low dielectric materials.]

In the above-mentioned silane compounds (the silane compounds (i), and (1) to (6), X in the above-mentioned average composition formulas of the silane compounds is defined by the following formula (7):

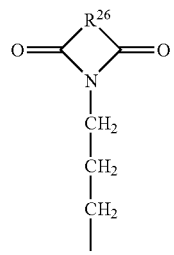

(7)

in the formula, $R^{26}$ denotes at least one structure selected from the group consisting of aromatic, heterocyclic, and alicyclic rings.

The above-mentioned $R^{26}$ is preferably same as $R^{1}$ described in description of the above-mentioned silane compound (1).

Particularly preferable examples of the above-mentioned silane compound is poly(γ-phthalimidoproylsilsesquioxane) in which $R^{26}$ is phenylene group, poly{γ-(hexahydro-4-methylphthalimido)propylsilsesquioxane} in which $R^{26}$ is methylcyclohexylene group, poly{γ-(1,8-naphthalimido)propylsilsesquioxane} in which $R^{26}$ is naphthylidene group, poly{γ-(5-norbornene-2,3-imido)propylsilsesquioxane) in which $R^{26}$ is divalent norbornene group, and poly[(cis-4-cyclohexen-1,2-imido)propylsilsesquioxane) in which $R^{26}$ is cyclohexenyl group. The structures of these compounds can be measured and identified by $^1$H-NMR, $^{13}$c-NMR, MALDI-TOF-MS.

It is preferable that the number of bonds between a silicon atom to which X is connected and an oxygen atom is 3. According to this, the silicon atom attached to X is not connected to another functional group, and therefore the above-mentioned silane compound is excellent in heat resistance, moisture resistance, and resistance to hydrolysis. For example, if the silicon atom attached to X is connected to one oxygen and further connected to another functional group, the heat resistance, the moisture resistance, and the resistance to hydrolysis might be reduced depending on the species of the functional group. It is preferable that the number of bonds between the silicon atom forming the siloxane bond and an oxygen atom is 3. According to this, the silicon atom forming the siloxane chain is connected to only the organic group represented by X. Therefore, such a siloxane compound can be more excellent in heat resistance and resistance to hydrolysis.

As the molecular structures of the above-mentioned silane compounds may be exemplified chain structures (chain and branched), ladder structures, net-like, cyclic, and cyclic structures comprising ladder structures, and cage-like structures, and among them, ladder-like, net-like, and cage-like ones are preferable since the effects are easily caused even if the addition amount of the above-mentioned silane compounds is slight. More preferable molecular structures differ in accordance with required effects, and for example, it is made possible to further lower the viscosity of a silane compound-containing composition and considerably suppress the moisture absorption of a cured article of the composition by forming cage-like molecular structure and it is made possible to further lower the viscosity of a silane compound-containing composition and considerably improve the heat resistance of a cured article of the composition although not so significantly suppress the moisture absorption by forming ladder-like molecular structure. That is, to lower the viscosity and suppress the moisture adsorption, the cage-like molecular structure is preferable and as described, the above-mentioned silane compounds having ladder-like molecular structures are also preferable embodiments of the invention. Possession of the cage-like molecular structures results in considerable decrease of viscosity of a composition containing the above-mentioned silane compounds and the composition or its cured article becomes highly excellent in the low moisture absorption property and at the same time the mechanical strength and heat resistance of the cured article can be improved further, so that the composition is made useful for various uses (especially, electronic parts and devices such as sealing materials for semiconductors). If the molecular structure has a ladder-like structure, the silane compound-containing composition has a lower viscosity. In addition, a cured article thereof obtains a significantly improved heat resistance, although such an improvement in the heat resistance is not remarkably observed in comparison to the reduction in the moisture absorption. That is, the preferable embodiments of the present invention include an embodiment in which the above-mentioned silane compound has a ladder-like molecular structure. Herein, the above-mentioned ladder-like, net-like and cage-like molecular structures are defined by the following structural formulas:

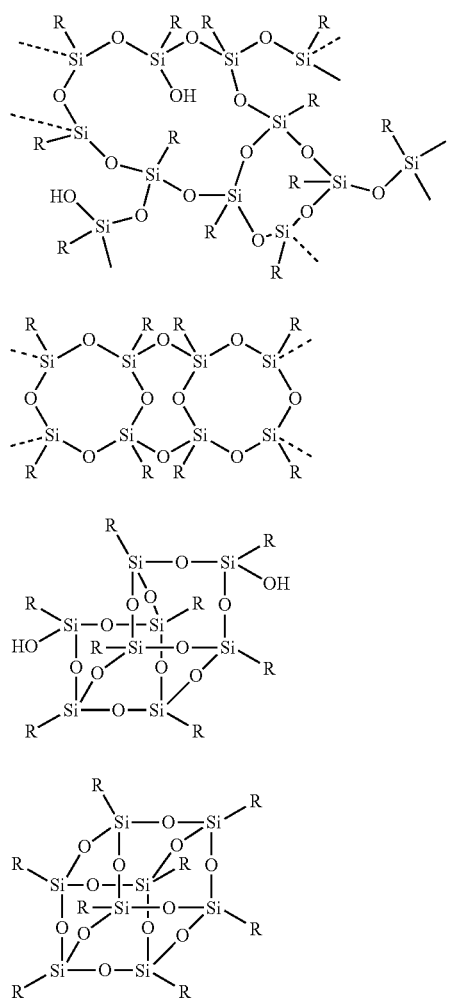

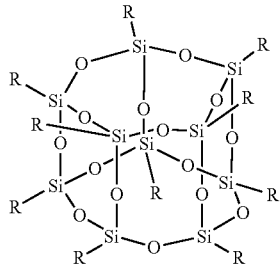

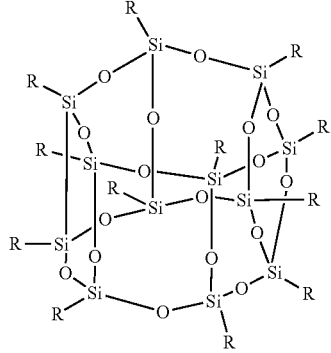

in the formula, R denotes the organic skeleton defined by "$X_aY_bZ_c$" in the above-mentioned average composition formula.

The above-mentioned structural formula (a) is a random (net-like) structure (Random structure): the structural formula (b) is a ladder-like structure (Ladder structure): the structural formula (c) is an incomplete cage-like structure (Incomplete condensed case): and the structural formulas (d) to (f) are cage-like structures (Completely condensed structures).

As exemplified by the above-mentioned structural formulas (c) to (f), the silane compounds having the above-mentioned cage-like molecular structures are preferable to comprise an organic skeleton layer forming a shell part and an inorganic skeleton layer forming a core part.

The silane compounds having the above-mentioned cage-like molecular structures are preferable to be those having a ring structure as X in the above-mentioned average composition formulas, and especially preferable to be silane compounds in which X is defined by the above-mentioned general formula (1), that is, the above-mentioned silane compound (1) having the ladder-like molecular structure. More preferable silane compounds are those having at least one structure selected from the group consisting of aromatic rings, saturated alicyclic hydrocarbons and unsaturated alicyclic hydrocarbons as $R^1$ in the above-mentioned general formula (1). It is made possible to sufficiently cause the above-mentioned effect that a composition containing the above-mentioned silane compounds is made to have a remarkably decreased viscosity, and the composition and its cured article are remarkably excellent in the low moisture absorption property by making the silane compounds have the above-mentioned configurations. Examples of the aromatic rings are benzene, biphenylene, terphenylene, naphthalene, anthracene, and penylene: examples of the saturated alicyclic hydrocarbons are cyclobutane, cyclopentane, cyclohexane, cyclooctane, norbornane, and decahydronaphthalene: and examples of the unsaturated alicyclic hydrocarbons are cyclobutene, cyclopentene, cyclohexene, cyclooctene, and norbornene.

The above-mentioned silane compounds having the ladder-like molecular structures are further preferably those in which X defined by the above-mentioned general formula (1)

denotes the structure defined by the above-mentioned general formulas (2) to (7), that is, the above-mentioned silane compounds (2) to (7) and particularly preferably those in which $R^1$ in the above-mentioned general formula (1) denotes benzene ring or norbornene structure.

One example of the silane compounds in which $R^1$ in the above-mentioned general formula (1) denotes norbornene structure is defined by the following formula.

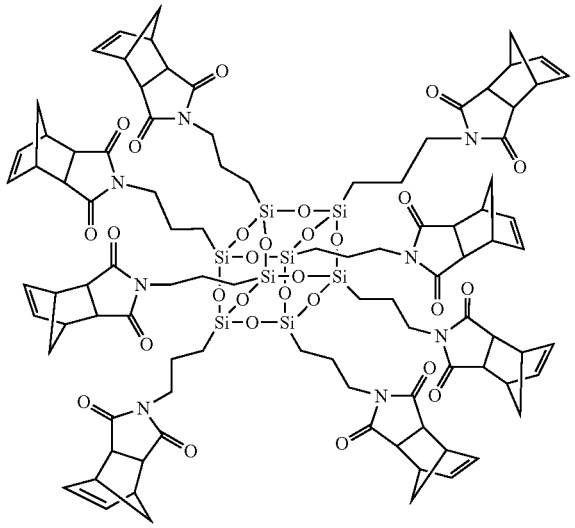

If the silane compound has a cage-like molecular structure, it is more preferable that a ratio of a silanol group amount, calculated by the following formula (α), is 0.1 or less.

[molar number of Si—OH bond]/[molar number of Si—O bond]  (α)

According to this, the composition containing the above-mentioned silane compound has a significantly low viscosity. In addition, such a composition or a cured article thereof has an extremely excellent resistance to moisture absorption. Such operation and effects can be more sufficiently exhibited. The ratio of the silanol group amount is still more preferably 0.05 or less, and particularly preferably 0.01 or less.

Most preferably, the above-mentioned silane compound contains no remaining silanol groups.

In this case, in the above-mentioned average composition formula, a+b+c is preferably 0.5 or more, and more preferably 0.7 or more, and still more preferably 0.7 or more and 1.0 or less, and particularly preferably 1. The coefficient d for oxygen is preferably 1.50.

The invention also provides a silane compound having a siloxane bond and an amido bond, wherein the silane compound is defined by the following average composition formula:

$X'_a Y_b Z_c SiO_d$:

in the formula, X' may be same or different and denotes an organic skeleton having an amido bond; z may be same or different and denotes an organic skeleton having no amido bond; Y may be same or different and denotes at least one selected from the group consisting of hydrogen atom, hydroxyl group, halogen atom, and OR group; R may be same or different and denotes at least one selected from the group consisting of alkyl, acyl, aryl, and unsaturated aliphatic residual groups and may have a substituent; a is a numeral of 3 or lower but not 0; b is 0 or a numeral less than 3; c is 0 or a numeral less than 3; d is a numeral less than 2 but not 0; and a+b+c+2d=4) and preferably a silane compound in which X' in the average composition formula is defined by the following formula (8):

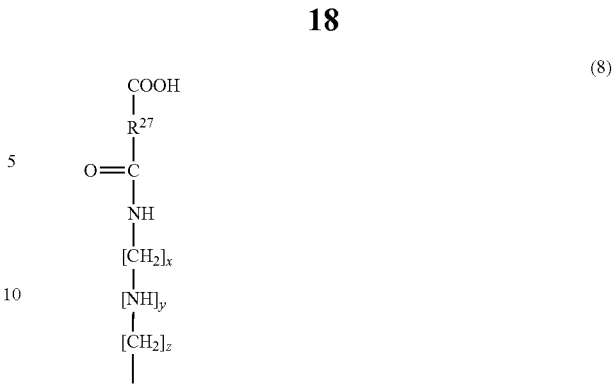

in the formula, $R^{27}$ denotes at least one structure selected from the group consisting of aromatic, heterocyclic, and alicyclic rings; x and z may be same or different and independently denote an integer of 0 or higher and 5 or lower; and y is 0 or 1. As described, the silane compound in which X' of the above-mentioned average composition formula $(X'_a Y_b Z_c SiO_d)$ is defined by the above-mentioned formula (8) is one of embodiments of the invention.

In an intermediate (8) in which X' is defined by the above-mentioned formula (8), $R^{27}$ is preferably phenylene, naphthylene, norbornene, and cyclohexylene. The reference characters x, y, and z are preferably x=0 or 2, y=0 or 1, and z=3 and more preferably x=0, y=0, and z=3. In this connection, Y, Z, a, b, c, and d are preferable to be same as those in the above-mentioned silane compound (1). Practically, Y is preferably hydroxyl group or OR group and more preferably OR group and even more preferably OR alkyl group of 1 to 8 carbon atom(s). Z is preferably at least one selected from the group consisting of alkyl group, aromatic residual groups such as aryl and aralkyl groups, and unsaturated aliphatic residual groups. These groups may have a substituent. It is more preferably alkyl having 1 to 8 carbon atom(s), or aromatic residual group such as aryl or aralkyl group which may have a substituent.

The molecular structure of the above-mentioned silane compound having the siloxane bond and amido bond is similar to that of the above-mentioned silane compound having the siloxane bond and imido bond and preferable molecular structures also differ depending on the desired effects. It is preferable that the number of bonds between a silicon atom to which X' is connected and an oxygen atom is 3. It is preferable that the number of bonds between a silicon atom forming the siloxane bond and an oxygen atom is 3. It is preferable in the silane compound that a silanol group amount calculated by the following formula (α) is 0.1 or less.

[molar number of Si—OH bond]/[molar number of Si—O bond]  (α)

The silanol group amount calculated by the above formula (α) is more preferably 0.05 or less, and still more preferably 0.01 or less. It is particularly preferable that the above-mentioned silane compound contains no remaining silanol group. Similarly, to lower the viscosity and actualize the low moisture absorption property, the cage-like molecular structure is preferable and accordingly, the above-mentioned silane compound having the cage-like molecular structure is one of preferable embodiments of the invention. It is preferable in such a silane compound having a cage-like molecular structure that $R^{27}$ in X' in the above-mentioned average composition formula is the same as $R^1$ in X in the above-mentioned silane compound having the siloxane chain and imido bond. It is preferable that the silane compound has a ring structure. As described above, the silane compound is further preferable to have at least one structure selected from the group consisting of aromatic rings, saturated alicyclic hydrocarbons and unsaturated alicyclic hydrocarbons as $R^{27}$ in the above-mentioned general formula (8) and even more preferable to have a benzene ring or a norbornene structure as $R^{27}$ in the above-mentioned general formula (8).

One example of the compounds defined by the above-mentioned general formula (8) in which $R^{27}$ denotes the norbornene structure is defined by the following formula.

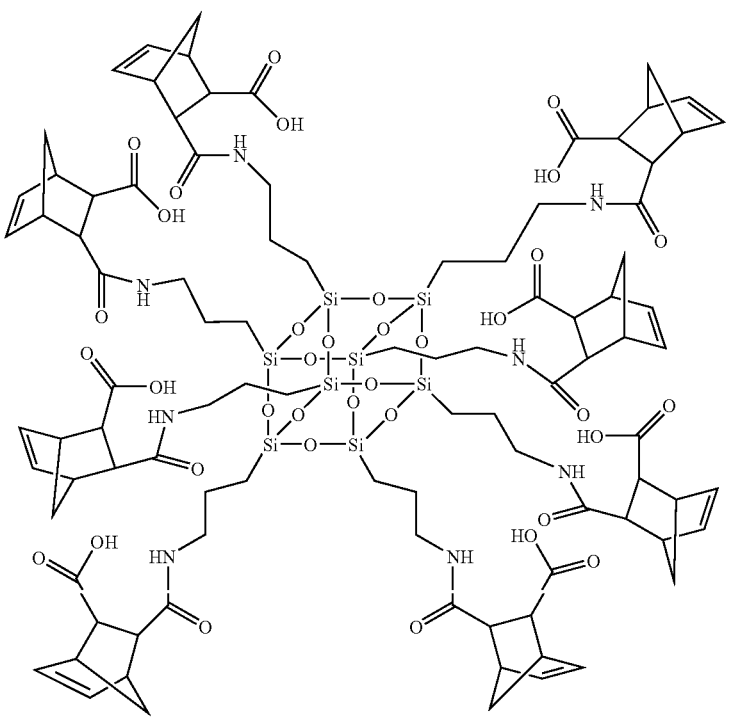

As described above, the above-mentioned silane compound having the cage-like molecular structure is also preferable to be those having no residual silanol group and also in this case, the mole ratio of the organic skeleton defined as "$X'_a Y_b Z_c$" and "Si" is preferably 1:1 and in the case the ratios of the organic skeleton and "Si" are both 1 mole, it is preferable that the ratio of "O (oxygen atom)" is 1.5 mole.

The invention also provides a silane compound having a siloxane bond and an amido bond, wherein the silane compound is defined by the following formula (9):

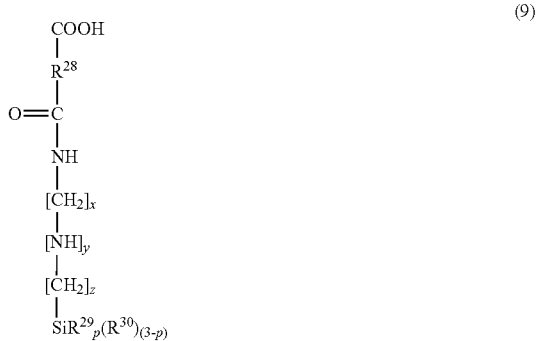

(9)

in the formula, $R^{28}$ denotes at least one structure selected from the group consisting of aromatic, heterocyclic, and alicyclic rings; $R^{29}$ may be same or different and denotes an organic group; $R^{30}$ may be same or different and denotes at least one selected from hydrogen atom, hydroxyl group, halogen atom, and $OR^{30'}$ group; $R^{30'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and p is an integer of 0 or higher and 2 or lower.

In the above-mentioned formula (9), $R^{28}$ is preferably phenylene, naphthylene, norbornene, and cyclohexylene. $R^{29}$ is preferably an organic group containing no amido bond. Practically, it is preferably one selected from the group consisting of alkyl group, aromatic residual groups such as aryl and aralkyl groups, and unsaturated aliphatic residual groups. These groups may have a substituent. It is more preferably alkyl group having 1 to 8 carbon atom(s), or aromatic residual group such as aryl or aralkyl group which may have a substituent. These organic groups may have a substituent. It is even more preferably methyl or ethyl. $R^{30}$ is preferably hydroxyl group or $OR^{30'}$ group, more preferably $OR^{30'}$ group, furthermore preferably $OR^{30'}$ group of which $R^{30'}$ group is an alkyl group having 1 to 8 carbon atom(s), and even more preferably $OR^{30'}$ group of which $R^{30'}$ is methyl, ethyl, or propyl. The reference characters x, y, and x are preferable to be x=0 or 2, y=0 or 1, and z=3 and more preferable to be x=0, y=0, and z=3 and p is an integer of 0 or 1.

The invention also provides a silane compound having a siloxane bond and an imido bond, wherein the silane compound is defined by the following formula (10):

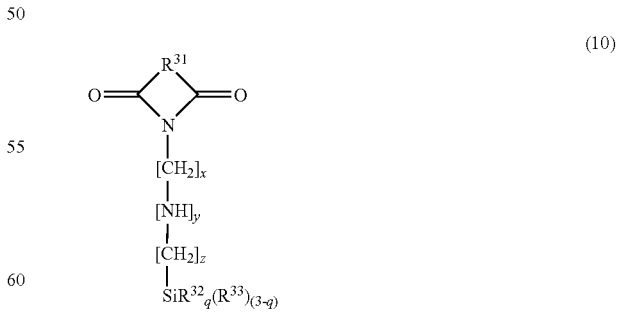

(10)

in the formula, $R^{31}$ denotes at least one structure selected from the group consisting of aromatic, heterocyclic, and alicyclic rings; $R^{32}$ may be same or different and denotes an organic group; $R^{33}$ may be same or different and denotes at least one selected from hydrogen atom, hydroxyl group, halogen atom, and $OR^{33'}$ group; $R^{33'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and q is an integer of 0 or higher and 2 or lower.

In the above-mentioned formula (10), $R^{31}$ is preferably phenylene, naphthylene, norbornene, and cyclohexylene. $R^{32}$ is preferably an organic group containing no imido bond. Practically, it is preferably one selected from the group consisting of alkyl group, aromatic residual groups such as aryl and aralkyl groups, and unsaturated aliphatic residual groups. These groups may have a substituent. It is more preferably alkyl group having 1 to 8 carbon atom(s), or aromatic residual group such as aryl or aralkyl group which may have a substituent. These organic groups may have a substituent. It is even more preferably methyl or ethyl. $R^{33}$ is preferably hydroxyl group or $OR^{33'}$ group, more preferably $OR^{33'}$ group, further preferably $OR^{33'}$ group of which $R^{33'}$ is an alkyl group having 1 to 8 carbon atom(s), and even more preferably $OR^{33'}$ group of which $R^{33'}$ is methyl, ethyl, or propyl. The reference characters x, y, and x are preferable to be x=0 or 2, y=0 or 1, and z=3 and more preferable to be x=0, y=0, and z=3 and q is an integer of 0 or 1.

Production methods of the above-mentioned intermediates (8) to (10) are not particularly limited, however, it is preferable to produce these intermediates by the following production methods. The intermediate (8) produced by the following production method involving production process (II-1) or production process (II-2); the intermediate (9) produced by the following production method involving production process (III-1); and the intermediate (10) produced by the following production method involving production process (V-1) or production process (V-2) are also preferable embodiments of the invention.

The invention also provides a silane compound production method for producing the above-mentioned silane compounds.

The above-mentioned silane compound production method is practically preferable to involve the following processes (I) to (V). Due to the involvement of the processes, there are advantages: usability of industrially available materials, suitability for industrial production processes, and efficient production by selecting production routes and intermediates.

As the above-mentioned production method, the invention provides a method for producing the above-mentioned silane compound (the above-mentioned silane compound (i) or silane compound (1) defined by the above-mentioned formula (1)), wherein the production method is a method for producing the silane compound (the silane compound (1) or silane compound (i)) involving imidizing an intermediate composed of a silane compound defined by the following average composition formula:

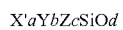

in the formula, X' may be same or different and denotes an organic skeleton having an amido bond; z may be same or different and denotes an organic skeleton having no amido bond; Y may be same or different and denotes at least one selected from the group consisting of hydrogen atom, hydroxyl group, halogen atom, and OR group; R may be same or different and denotes at least one selected from the group consisting of alkyl, acyl, aryl, and unsaturated aliphatic residual groups and may have a substituent; a is a numeral of 3 or lower but not 0; b is 0 or a numeral less than 3; c is 0 or a numeral less than 3; d is a numeral less than 2 but not 0; and a+b+c+2d=4: in the formula, X' in the average composition formula is defined by the following formula (8):

in the formula, $R^{27}$ denotes at least one structure selected from the group consisting of aromatic, heterocyclic, and alicyclic rings; x and z may be same or different and independently denote an integer of 0 or higher and 5 or lower; and y is 0 or 1. "The intermediate composed of a silane compound, in which X' is defined by the formula (8)" means that a silane compound in which X' is defined by the formula (8) is used as the intermediate. The above-mentioned Y, Z, a, b, c, and d are preferable to be same respectively as those described in the above-mentioned average composition formula and the above-mentioned $R^{27}$, x, y, and z are preferable to be same respectively as those described for $R^1$, x, y, and z in the above-mentioned silane compound (1).

With respect to the above-mentioned production method (referred to also as production method (I)), the method is not particularly limited if it involves imidizing process (referred to also as imidation process (I)) of the intermediate defined by the above-mentioned formula (8) (hereinafter, referred to also as intermediate (8)). The imidation process (I) is a process of imidizing the intermediate by dehydration ring-closing reaction of an amic acid and the reaction conditions are as follows.

The reaction temperature of the above-mentioned imidation process is preferably 80 to 300° C. It is more preferably 100 to 200° C. and further preferably it is kept at an azeotropic temperature of water and a solvent or higher since water is produced as a byproduct. The reaction pressure may be ambient or pressurized or vacuumed pressure, however, since reaction is well promoted by efficiently removing the produced water outside of the reaction system, it is preferably ambient pressure or vacuumed. Practically, pressure of 0.01 to 0.5 MPa is preferable.

As reaction catalysts, conventionally known and useful amines such as pyridine, triethylamine, imidazole diazabicycloundecene, tetramethylammonium hydroxide or the like may be used and azeotropic solvents with water such as toluene and xylene are preferable to be added.

Although differing in accordance with the reaction temperature and the reaction composition, the reaction time is preferably 2 to 48 hours.

The above-mentioned production method (the production method (I)) is preferable to involve processes of hydrolysis and polycondensation of an intermediate composed of a silane compound defined by the following formula (9):

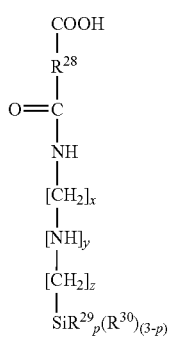

(9)

in the formula, $R^{28}$ denotes at least one structure selected from the group consisting of aromatic, heterocyclic, and alicyclic rings; $R^{29}$ may be same or different and denotes an organic group; $R^{30}$ may be same or different and denotes at least one selected from hydrogen atom, hydroxyl group, halogen atom, and $OR^{30'}$ group; $R^{30'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and p is an integer of 0 or higher and 2 or lower.

That is, the production method (referred to also as production method (II)) involves, in addition to the imidation process (I), a process (referred to also as process (II-1)) of obtaining the intermediate (8) from the intermediate defined by the above-mentioned formula (9) (referred to also as intermediate (9)). In this connection, $R^{28}$, x, y, and z are preferable to be same respectively as those described for $R^1$, x, y, and z in the above-mentioned silane compound (1). Further, $R^{29}$ and $R^{30}$ are preferable to be same as the above-mentioned $R^{29}$ and $R^{30}$. The reference character p is preferably 0 or 1.

The above-mentioned process (II-1) is a process of obtaining the intermediate (8) by forming a polysiloxane skeleton by hydrolysis and polycondensation of alkoxysilyl group of the intermediate (9).

If the above-mentioned process (II-1) is involved, since the intermediate (9) (intermediate defined by the above formula (9)) with high hydrophilicity is formed as a precursor of the intermediate (8), the reaction efficiency of the hydrolysis and polycondensation of the alkoxysilyl group is heightened to result in increasing of the polymerization degree of the polysiloxane skeleton.

In the above-mentioned process (II-1), the intermediate (9) is mixed with water or an organic solvent containing water to carry out hydrolysis and condensation of the intermediate (9).

It is made possible to form the polysiloxane skeleton as hydrolyzed and condensed product by such hydrolysis and condensation. The hydrolyzed and condensed product is a compound obtained by further promoting condensation reaction of a product obtained by hydrolysis reaction.

Hereinafter, the hydrolysis reaction and condensation reaction of the intermediate (9) are shown.

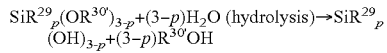

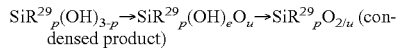

in the formula, $R^{29}$, $R^{30}$, and p are as described above, and e and u are arbitrary numerals.

It is made possible to obtain the intermediate (8) having a polysiloxane skeleton with a high polymerization degree by hydrolyzing and condensing the intermediate (9) in the above-mentioned manner.

In the above-mentioned hydrolysis and condensation reaction, water is used and the reaction is preferable to be carried out by adding 10 to 50% by weight of water based on 100% by weight of the intermediate (9). It is more preferable to add 20 to 40% by weight.

Water to be used for the above-mentioned reaction is any such as ion exchanged water, pH-adjusted water, or the like, however, it is preferable to use water at pH around 7. Use of such water makes it possible to lower the ionic impurity amount in the composition and give a resin composition with low moisture absorption property ad high insulation property. In terms of the purity of water, pH 7 is better, however, pH may be adjusted in a range of 2 to 12 since hydrochloric acid, oxalic acid, pyridine or triethylamine is evaporated outside of the reaction system at a high temperature.

The above-mentioned water use may be carried out by dropwise adding water to the intermediate (9) or collectively loading water.

The reaction temperature of the above-mentioned hydrolysis and polycondensation reaction of alkoxysilyl group is preferable room temperature to 200° C., more preferably room temperature to 100° C., and even more preferably to be kept at azeotropically fluxing temperature of alcohol, water, and the solvent since alcohol is produced as a byproduct. The reaction pressure may be normal pressure or pressurized pressure or reduced pressure, however, since reaction is well promoted by efficiently removing the produced alcohol outside of the reaction system, it is preferably normal pressure or lower. Further, although differing in accordance with the reaction temperature and the reaction composition, the reaction time is preferably 2 to 48 hours.

The above-mentioned intermediate (8) may be produced from an intermediate (hereinafter referred to also as intermediate (12)) in which X in the above-mentioned average composition formula is defined by the following formula (12):

(12)

in the formula, x and z may be same or different and independently denote an integer of 0 or higher and 5 or lower; and y is 0 or 1. The process of obtaining the intermediate (8) from the above-mentioned intermediate (12) (referred to also as process (II-2)) is also one of preferable embodiments. In the case the intermediate (12) is poly(γ-aminopropyl)silsesquioxane, the intermediate (12) has high water-solubility and presently there is no organic solvent which has sufficient solubility. In the process (II-2), the intermediate (12) and an acid anhydride are reacted, however, in the presence of water, the reaction is inhibited due to the hydration ring-opening reaction of the acid anhydride and therefore, the yield of the intermediate (8) is not so sufficiently high to carry out the production industrially at a low cost. Accordingly, it is adequate to employ the process (I) for producing the above-mentioned silane compound (1) via the process (II-1) in the case the intermediate (12) is poly(γ-aminopropyl)silsesquioxane.

The above-mentioned reference characters x, y, and z are preferable to be same respectively as x, y, and z described in the above-mentioned silane compound (1).

The above-mentioned process (II-2) is a process of obtaining the intermediate (8) from the intermediate (12) and the reaction conditions are generally preferable to be the same as those of a process for introducing the amic acid structure of the following process (III-1).

The production method of the above-mentioned intermediate (9) is not particularly limited, however, it is preferable to obtain the intermediate (9) from a compound (referred to as compound (13)) defined by the following formula (13). That is, the above-mentioned production method (production method (II)) is preferable to involve a process (referred to also as process (III-1)) of obtaining an intermediate composed of a silane compound defined by the formula (9) by ring-opening addition of an acid anhydride to a compound defined by the following formula (13):

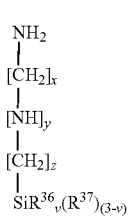

(13)

in the formula, $R^{36}$ may be same or different and denotes an organic group; $R^{37}$ may be same or different and denotes at least one selected from hydrogen atom, hydroxyl group, halogen atom, and $OR^{37'}$ group; $R^{37'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and v is an integer of 0 or higher and 2 or lower, or a process (referred to also as process (III-2)) of obtaining an intermediate composed of a silane compound in which X is defined by the formula (12) by hydrolyzing and polycondensing a compound defined by the above-mentioned formula (13).

That is, such production method (referred to also as production method (III)) involves, in addition to the imidation process, the hydrolysis and polycondensation process (II-1) or the amic acid structure introduction process (II-2) and also the process (the process (III-1)) of obtaining the intermediate (9) from the compound (13) or a process (the process (III-2)) of obtaining the intermediate (12) from the compound (13). Involvement of such processes results in advantage that inexpensive raw materials can be utilized for production. The reference characters x, y, and z are preferable to denote independently same as the characters x, y, and z described for the above-mentioned silane compound (I). Further, $R^{36}$, $R^{37}$, and v are preferable to denote independently same as $R^{29}$, $R^{30}$, and p described for the above-mentioned silane compound (9).

The above-mentioned process (III-1) is a ring-opening addition process of obtaining the intermediate (9) from the compound (13) and the reaction conditions are described below.

With respect to the water concentration in the above-mentioned process (III-1), it is preferable to dry the solvent and the reaction apparatus, and circulate dried nitrogen gas during the reaction since the yield of the aimed compound is decreased by hydration of the acid anhydride. The solvent may be dried by using a conventionally known and employed dehydration agent such as molecular sieve, dehydrated magnesium sulfate, and dehydrated calcium chloride or by carrying out distillation before reaction.

The reaction temperature of the above-mentioned process is preferably room temperature to 100° C. and more preferably 40 to 90° C. The reaction is sufficiently promoted even at room temperature, however, depending on the reaction product, the product is precipitated during the reaction, which causes the inadequate stirring condition in some cases and therefore, it is preferable to carry out the reaction at a temperature slightly higher than room temperature. The pressure of the above-mentioned process may be ambient or pressurized or vacuumed. Although differing according to the reaction temperature and the reaction composition, the reaction time is preferably about 2 to 48 hours.

The above-mentioned process (III-2) is a process of obtaining the intermediate (12) by forming the polysiloxane skeleton by hydrolysis and polycondensation reaction of the alkoxysilyl group of the compound (13) and the reaction conditions are preferably same as those of the above-mentioned process (II-1).

Preferable embodiments of the above-mentioned production method (III) may be a method involving the process (III-1), process (II-1), and process (I) (embodiment (A)), and a method involving the process (III-2), process (II-2), and process (I) (embodiment (B)). Especially, in the embodiment (B), in the case of forming poly(γ-aminopropyl)silsesquioxane as the intermediate (12), the embodiment (A) is more preferable to be employed.

The above-mentioned embodiment (A) is a method involving obtaining the intermediate (9) by ring-opening addition reaction of an acid anhydride from the compound (13) (process (III-1)), obtaining the intermediate (8) by hydrolyzing and polycondensing the intermediate (9) (process (II-1)), and obtaining the silane compound (i) or the silane compound (1) by imidizing the intermediate (8). Further, the above-mentioned embodiment (B) is a method involving obtaining the intermediate (12) by hydrolyzing and polycondensing the compound (13) (process (III-2)), obtaining the intermediate (8) from the intermediate (12) (process (II-2)), and obtaining the silane compound (i) or the silane compound (1) by imidizing the intermediate (8).

A preferable embodiment of the invention is also a method for producing the above-mentioned silane compound (the above-mentioned silane compound (i) or the silane compound (1) defined by the above-mentioned formula (1)), wherein the production method is a method for producing a silane compound involving hydrolyzing and condensing an intermediate composed of a silane compound defined by the following formula (10):

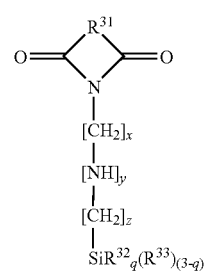

(10)

in the formula, $R^{31}$ denotes at least one structure selected from the group consisting of aromatic, heterocyclic, and alicyclic rings; $R^{32}$ may be same or different and denotes an organic group; $R^{33}$ may be same or different and denotes at least one selected from hydrogen atom, hydroxyl group, halogen atom, and $OR^{33'}$ group; $R^{33'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and q is an integer of 0 or higher and 2 or lower. The above-mentioned $R^{31}$, x, y, and z are preferable to denote independently same as $R^1$, x, y, and z described for the above-mentioned silane compound (1). Further, $R^{32}$, $R^{33}$, and q are preferable to denote independently same as $R^{29}$, $R^{30}$, and p described for the above-mentioned silane compound (9).

The production method involving the above-mentioned process (referred to also as production method (IV)) is not particularly limited if it involves the process (referred to also as hydrolysis and polycondensation process (IV)) of hydrolyzing and polycondensing the intermediate (hereinafter, referred to as intermediate (10)) defined by the above-mentioned formula (10). The reaction conditions in the hydrolysis and polycondensation process (IV) are same as those of the above-mentioned process (II-1). Involvement of the hydrolysis and polycondensation process (IV) makes it possible to use the intermediate (10) which is previously highly purified, so that the method can be advantageous in that a process of removing impurity of the obtained silane compound (1) can be omitted.

The above-mentioned production method (production method (IV)) is preferable to involve a process of obtaining the intermediate composed of the silane compound defined by the above-mentioned formula (10) from a compound defined by the following formula (11):

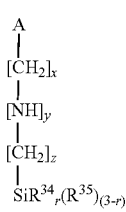

(11)

in the formula, A denotes halogen atom or isocyanato group; $R^{34}$ may be same or different and denotes an organic group; $R^{35}$ may be same or different and denotes at least one selected from hydrogen atom, hydroxyl group, halogen atom, and $OR^{35'}$ group; $R^{35'}$ may be same or different and denotes at least one selected from the group consisting of alkyl, acyl, aryl, and unsaturated aliphatic residual groups and may have a substituent; x and z may be same or different and independently denote an integer of 0 or higher and 5 or lower; y is 0 or 1, and r is an integer of 0 or higher and 2 or lower.

That is, such a production method (referred to also as production method (V)) involves, in addition to the hydrolysis and polycondensation process (IV), a process (referred to also as process (V)) of obtaining the intermediate (10) from the compound (11). Involvement of the process is advantageous in that a wide variety of raw materials for introducing the imido skeleton can be selected. The reference characters x, y, and z are preferable to denote independently same as x, y, and z described for the above-mentioned silane compound (1). Further, $R^{34}$, $R^{35}$, and r are preferable to denote independently same as $R^{29}$, $R^{30}$, and p described for the above-mentioned silane compound (9).

In the process (V), in the case A of the compound (11) is isocyanato group (referred to also as process (V-1)), the process (V-1) is imidation process of the isocyanato group and the following reaction conditions are preferable.

With respect to the water concentration in the above-mentioned process (V-1), it is preferable to dry the solvent and the reaction apparatus, and circulate dried nitrogen gas during the reaction since the yield of the aimed compound is decreased by hydrolysis of the isocyanato group. The solvent may be dried by using a conventionally known and employed dehydration agent such as molecular sieve, dehydrated magnesium sulfate, and dehydrated calcium chloride or by carrying out distillation before reaction. The reaction temperature of the above-mentioned process is preferably 60 to 250° C. and more preferably 120 to 180° C. Depending on the reaction product, the product is precipitated during the reaction to make it impossible to stir the reaction system and therefore, the reaction temperature is slightly higher than room temperature. The pressure of the above-mentioned process may be normal pressure or pressurized pressure or reduced pressure. Since carbon dioxide in an amount equimolecular to that of the raw material is generated as a byproduct, the reaction apparatus is preferable to be an open system. Although differing according to the reaction temperature and the reaction composition, the reaction time is preferably about 2 to 48 hours.

In the above-mentioned process (V), in the case A of the compound (11) is halogen atom (referred to also as process (V-2)), the process (V-2) is an imidation process of the haloalkyl and the following reaction conditions are preferable.

The reaction temperature in the above-mentioned process (V-2) is preferably room temperature to 150° C. and more preferably 40 to 120° C. Depending on the reaction product, the reaction product is precipitated during the reaction to make stirring of the reaction system impossible and therefore, the reaction is preferable to be carried out at a temperature higher than room temperature.

It is preferable to add, as a reaction catalyst in the above-mentioned process (V-2), an alkaline compound capable of forming a salt with hydrogen halide, e.g. carbonates such as potassium carbonate, cesium carbonate, lithium carbonate, and sodium carbonate; basic ion exchange resins; and amine compounds such as triethylamine, pyridine, diazabicycloundecene. The addition amount is preferable to be equimolecular to that of a raw material or more. After the reaction, since the salt is precipitated in the reaction solution, the salt is preferable to be removed by filtration, washing with water, or washing with an alcohol. It is preferable to employ filtration process in the case alkoxysilyl group exists in the reaction raw material.

The pressure of the above-mentioned process may be normal temperature or pressurized pressure or reduced pressure. Since carbon dioxide in an amount equimolecular to that of the raw material is generated as a byproduct, the reaction apparatus is preferable to be an open system. According to the reaction temperature and the reaction composition, the reaction time is adjustable and preferably about 2 to 48 hours.

Preferable embodiments of the above-mentioned production method (V) may be a method involving the process (V-1) and process (IV) (embodiment (C)), and a method involving the process (V-2) and process (IV) (embodiment (D)).

The above-mentioned embodiment (C) is a method involving obtaining the intermediate (10) from the compound (11) in which A is isocyanato group (process (V-1)) and obtaining the silane compound (i) or the silane compound (1) hydrolyzing and polycondensing the intermediate (10). Further, the above-mentioned embodiment (D) is a method involving obtaining the intermediate (10) from the compound (11) in which A is halogen atom (process (V-2)) and obtaining the silane compound (i) or the silane compound (1) by hydrolyzing and polycondensing the intermediate (10).

The above-mentioned embodiments (A) to (D) are preferable for the method of obtaining the silane compound (1) in the invention, and especially, in terms of industrially safe and low cost production and high yield, the embodiments (A), (C), and (D) are more preferable. The embodiment (A) is even more preferable.

In the above-mentioned production methods (I) to (V), the methods involve the process of forming the siloxane skeleton (process (II-1), (III-2), and (IV)); the process of introducing the amic acid structure (process (II-2) (III-1); and the process of forming the organic skeleton having an imido bond (process (I), (V-1), (V-2)). In the process of forming the siloxane skeleton, hydrolysis and polycondensation are carried out to form the siloxane bond and as one example, a production method (IV) (hydrolysis and polycondensation process (IV)) will be described.

In the above-mentioned production method (IV), it is preferable to carry out hydrolysis and polycondensation of a structure unit obtained by bonding at least one organic skeleton having an imido bond with solely a monomer (monomer $M^1$) having a structure in which a hydrolysable and polycondensable group is connected to silicon atom or also with another monomer (monomer $M^2$). Practically the monomer $M^1$ is preferably those defined by a general formula:

$$X_f Z_h Y^1_g Si$$

in the formula, X and Z denote same as described above; $Y^1$ denotes a hydrolysable group; f and g may be same or different and denote an integer of 1 to 3; h is an integer of 0 to 2; and f+g+h=4. Practically, preferable examples are the following.

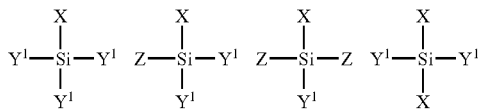

The organic silicon monomer $M^2$ is preferably those defined by a general formula:

$$Z_k Y^1_j Si$$

in the formula, $Y^1$ and Z denote same as described above; k denotes an integer of 0 to 3; j is an integer of 1 to 4; and k+j=4. In addition, in the above-mentioned monomers $M^1$ and $M^1$, $Y^1$ is preferable atom and group described for the above-mentioned Y.

As described, since two or more kinds monomers indispensably including the monomer $M^1$ are used, it is made possible to produce a silane compound having a polysiloxane skeleton comprising a structure unit formed by connecting at least one organic group having an imido bond derived from the monomer $M^1$ to silicon atom (in the case of co-condensation of two or more kind monomers $M^1$, a silane compound having a polysiloxane skeleton having the co-condensation composition). It is also made possible to produce a silane compound having a polysiloxane skeleton formed by co-condensation of a structure unit formed by connecting at least one organic group having an imido bond derived from the monomer $M^1$ to silicon atom with a structure unit formed by connecting an arbitrary organic group derived from the monomer $M^2$ to silicon atom or with a structure unit in which no organic group is connected to silicon atom.

In the same manner as the above-mentioned production method (IV), a silane compound defined by the above-mentioned formula (9) and another silane compound monomer having no amido bond are also co-hydrolyzed and condensed in the production process (II-1) to obtain an intermediate (8), which is a silane compound, comprising various kinds of combinations of various structure units, and the intermediate (8) is imidized to obtain the silane compound (1).

Similarly, in also the production process (III-2), a silane compound defined by the above-mentioned formula (13) and another silane compound monomer are co-hydrolyzed and condensed, and further the production process (II-2) and the production process (I) are successively carried out to obtain a silane compound having polysiloxane skeleton which may have various compositions indispensably comprising the structure unit formed by connecting the organic skeleton having an imido bond to at least one silicon atom.

The above-mentioned production methods (e.g. the embodiments (A) to (D)) may be selected properly in accordance with the silane compounds to be obtained. The silane compounds obtained in the above-mentioned manner can be used preferable for the above-mentioned uses and a silane compound to be produced by the above-mentioned production methods is also one of preferable embodiments of the invention. For example, the silane compounds are also preferably composed of copolymers obtained by co-hydrolyzing and condensing organic silicon monomers $M^1$, which are obtained by connecting at least one organic skeleton having an imido bond to a silicon atom and connecting at least a group hydrolysable and/or capable of forming siloxane bond (called also as hydrolysable group: e.g. alkoxy, hydrogen atom, halogen atom, and hydroxyl group) to the same silicon atom, either alone (including homopolymers and co-condensed polymers of two or more kinds of organic silicon monomers $M^1$) or with hydrolysable and condensable silicon monomers $M^2$ containing no organic skeleton X.

The following compounds are preferable as the above-mentioned silicon monomers $M^2$. Tetraalkoxysilanes such as tetramethoxysilane, tetraethoxysilane, tetra-n-propoxysilane, tetra-iso-propoxysilane, tetra-n-butoxysilane, tetra-iso-butoxysilane, tetra-sec-butoxysilane, and tetra-tert-butoxysilane; trialkoxysilane such as methyltrimethoxysilane, methyltriethoxysilane, ethyltrimethoxysilane, ethyltriethoxysilane, n-propyltrimethoxysilane, n-propyltrimethoxysilane, iso-propyltrimethoxysilane, iso-propyltriethoxysilane, 3,3,3-trifluoropropyltrimethoxysilane, 3,3,3-trifluoropropyltriethoxysilane, 3-mercaptopropyltrimethoxysilane, 3-aminopropyltrimethoxysilane, 3-aminopropyltriethoxysilane, phenyltrimethoxysilane, phenyltriethoxysilane, benzyltrimethoxysilane, benzyltriethoxysilane, 3-glycidyloxypropyltrimethoxysilane, 3-glycidyloxypropyltriethoxysilane, 2-(3,4-epoxycyclohexyl)ethyltrimethoxysilane, 2-(3,4-epoxycyclohexyl)ethyltriethoxysilane, vinyltrimethoxysilane, vinyltriethoxysilane, 3-(meth)acryloxypropyltrimethoxysilane, and 3-(meth)acryloxypropyltriethoxysilane; dialkoxysilanes such as dimethyldimethoxysilane, dimethyldiethoxysilane, diethyldimethoxysilane, diethyldiethoxysilane, di-n-propyldimethoxysilane, di-n-propyldiethoxysilane, di-iso-propyldimethoxysilane, di-iso-propyldiethoxysilane, diphenyldimethoxysilane, and diphenyldiethoxysilane; tetraacyloxysilanes such as tetraacetyloxysilane and tetrapropionyloxysilane; triacyloxysilanes such as methyltriacetyloxysilane and ethyltriacetyloxysilane; and diacyloxysilanes such as dimethyldiaceyloxysilane and diethyldiacetyloxysilane. Among these silanes are tetramethoxysilane, tetraethoxysilane, methyltrimethoxysilane, methyltriethoxysilane, dimethyldimethoxysilane, dimethyldiethoxysilane preferable. As described, it is preferable to contain silicon alkoxides. Further, the trialkoxysilanes are preferable as each of $M^1$ and $M^2$.

It is also preferable to produce the above-mentioned silane compound having the cage-like molecular structure (the above-mentioned silane compound (i) or the silane compound (1) defined by the above-mentioned general formula (1)) by the above-mentioned production methods (the above-mentioned production methods (I), (II), (III), (IV), and (V)) and more particularly, it is more preferable to produce the compound by the above-mentioned method (III) or the above-mentioned method (IV). In this case, the compound defined by the formula (13) is preferable as a starting material in the above-mentioned method (III). Further, the compound defined by the formula (11) is preferable as a starting material in the above-mentioned method (IV).

The compound defined by the formula (13) or the formula (11) having the cage-like molecular structure can be produced by the synthesis procedure described in, for example, Reference Document 1 (F. J. Feher and K. D. Wyndham, Chem. Comm., 1998, 323-324) using a compound defined by the following formula (g):

$$NH_2-R^1-SiX_3 \qquad (g)$$

in the formula, $R^1$ denotes at least one structure selected from the group consisting of aromatic, heterocyclic, and alicyclic rings; and X may be same or different and denotes hydrolysable group or hydroxyl group; wherein the hydrolysable group is hydrogen atom, halogen atom, alkoxy, or acyloxy group: as a starting substance.

One example of the production method of obtaining the silane compound having the cage-like molecular structure by using a starting substance defined by the above-mentioned formula (g) will be shown by the following formula, however, the method is not particularly limited to this embodiment.

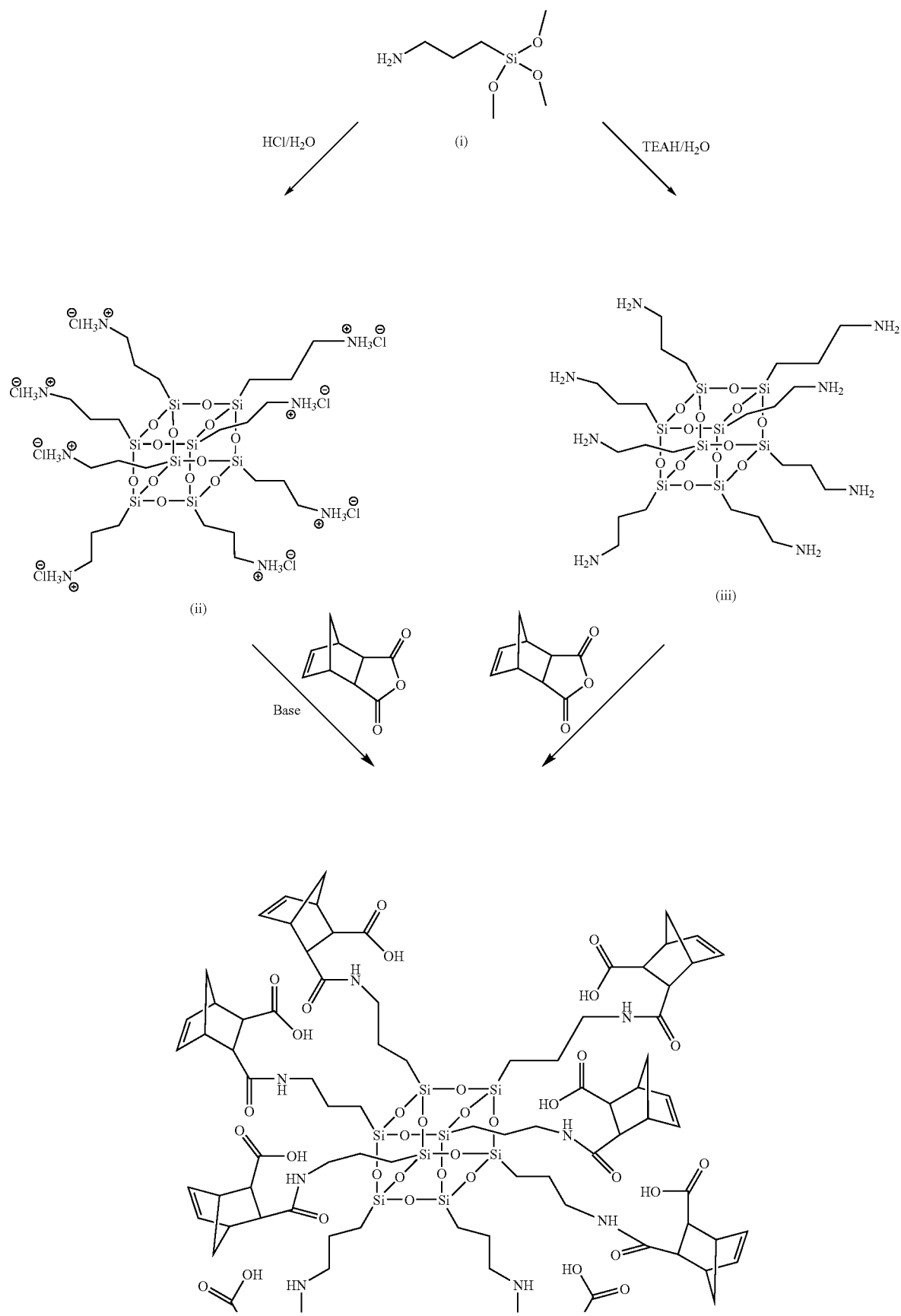

-continued

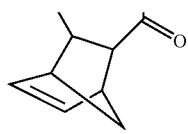
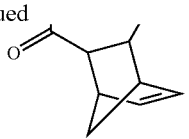

(iv)

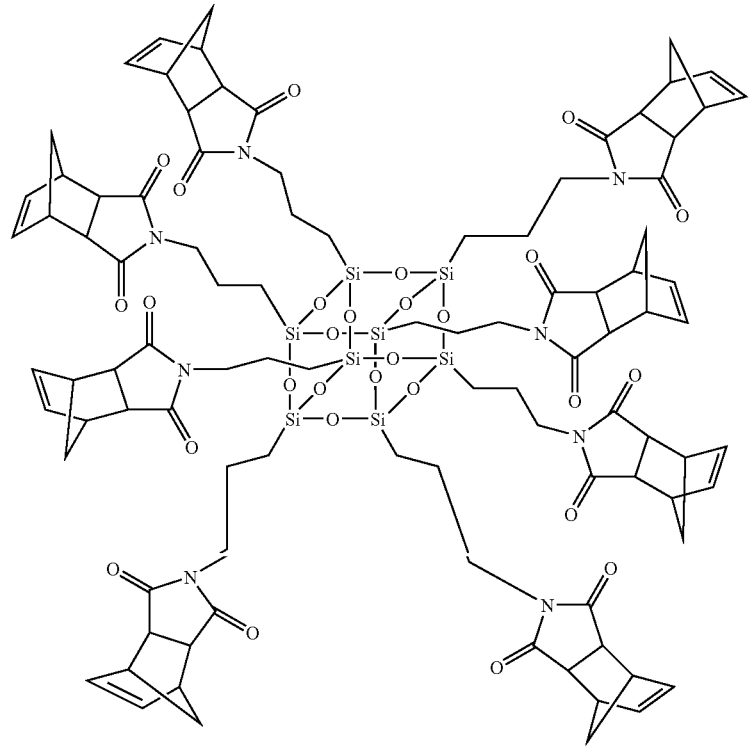

(v)

The above-mentioned formula will be described.

As the means of obtaining the silane compound having the ladder-like amic acid structure (iv) from the compound defined by the above-mentioned formula (g), which is a starting substance, can be exemplified two procedures; one is a procedure of obtaining the silane compound via a compound having NH3+ ion (the counter ion is arbitrary) (the process of obtaining (ii) from (i) in the formula) and the other is a procedure of obtaining the silane compound via a compound having amino group (the process of obtaining (iii) from (i) in the formula).

In the formula, the process of obtaining (ii) from (i) is a process of subjecting the compound defined by the formula (g) to hydrolysis and condensation reaction in the presence of hydrochloric acid, and furthermore, the process from (i) to (iii) is a process of the compound defined by the formula (g) to hydrolysis and condensation reaction.

Through these processes, the compound having no silanol group and defined as (ii) or (iii) can be obtained. The compound corresponds to the above-mentioned compound defined by the formula (13) or (11) and having the cage-like molecular structure.

Thereafter, the compound (ii) or (iii) is reacted with an acid anhydride, that is, in the formula, 5-norbornene-2,3-dicarboxylic acid anhydride, by ring-opening addition reaction to obtain cage-like silsesquioxane (iv) with amic acid structure defined as (iv).

Further, the compound (iv) is subjected to dehydration and cyclization reaction to obtain a cage-like silsesquioxane having an imido bond and defined as (iv).

The invention is also a resin composition containing the above-mentioned silane compound (the above-mentioned silane compound (i) or the above-mentioned silane compound (1) defined by the formula (1)) and an organic resin. Such a resin composition is a composition containing the silane compound mixed with a polymer and since the composition contains the silane compound, the composition shows excellent heat resistance and scarcely causes weight decrease or mechanical physical deterioration even if being left at a high temperature for a long duration and therefore is particularly useful for mounting materials with high heat resistance. Further, the composition is usable not only for the mounting fields where high thermal stability is required but also for optical uses, optodevice uses, display device uses, mechanical part materials, electric and electronic part materials, automotive part material, civil engineering and construction materials, molding materials, and materials for coatings and adhesives.

With respect to the particularly preferable uses, the composition can be preferably used in semiconductor sealing materials, liquid sealing materials, under fill, transparent sealing materials for light emitting devices, passivation, semiconductor-mounting substrates, solder resist, adhesives for lead frames, adhesive films for semiconductor lamination, semiconductor mounting process films, e.g. die attachment film (DAF)/back-grinding films (BG)/dicing tapes (DC), and the like. In addition, the composition is also preferably used in semiconductor mounting uses (uses for semiconductor devices). Examples of such uses include: adhesives for conductive pastes; and adhesives for CCL (copper clad laminates) including copper foils and flexible films, e.g. crystalline polyesters such as polyimide and PEN (polyethylene naphthalate), PEEK (registered trade name, polyether ether ketone), and the like. Further, the composition is preferably used as a thermosetting binder resin composition for bond magnets, or a low dielectric material used in a semiconductor device and the like. There are materials having various mechanical physical properties from soft to highly rigid properties corresponding to the uses as these semiconductor mounting parts (parts for semiconductor devices) and use of the resin composition of the invention gives high insulation property, low moisture absorption, high heat resistance, and high adhesive property and thus the resin composition efficiently functions in form of any parts. As described, the embodiment of the resin composition for a semiconductor device (resin composition for mounting semiconductor) is one of preferable embodiments of the invention. Especially, a semiconductor sealing material and a semiconductor-mounting substrate using the above-mentioned resin composition for a semiconductor device are included in the invention. The resin composition is also preferable to be used as a resin composition for forming an adhesive layer for a semiconductor mounting process film.

The silane compound to be contained in the above-mentioned resin composition may be the above-mentioned silane compound (i) or the silane compound (1) defined by the above-mentioned formula (1) and preferable silane compounds are as described above.

In addition, if the above-mentioned resin composition is used as the resin composition for forming an adhesive layer for a semiconductor mounting process film, the above-mentioned silane compounds are preferable to be selected properly in accordance with the property of the organic resin.

For example, in the case the organic resin is a resin with high hydrophobicity, it is preferable in the above-mentioned silane compound that X in the above-mentioned average composition formula is defined by the following formula (A);

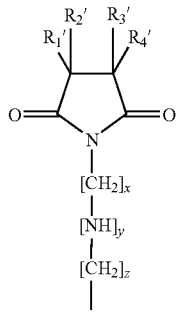

(A)

in the formula, $R^{1\prime}$, $R^{2\prime}$, $R^{3\prime}$, and $R^{4\prime}$ may be same or different and denote hydrogen atom or an organic group and may be connected to one another) wherein one of $R^{1\prime}$ and $R^{4\prime}$ is a non-aromatic organic group. It is more preferable that $R^{1\prime}$ and/or $R^{4\prime}$ is an alicyclic hydrocarbon group or an aliphatic chain hydrocarbon group. This configuration includes a configuration in which $R^{1\prime}$ and $R^{3\prime}$ are connected to each other to form a ring structure which is an aliphatic ring structure. It is further preferable that $R^{1\prime}$ and/or $R^{4\prime}$ is an aliphatic chain hydrocarbon even more preferably a group defined by the following formula;

—CH$_2$—CH(CH$_3$)=CH—R$^{5\prime}$ in the formula, $R^{5\prime}$ denotes a hydrocarbon group of 4 to 8 carbon atoms.

In the case the organic resin is a resin having a high polarity, it is preferable in the above-mentioned silane compound defined by the above-mentioned formula (A) that $R^{1\prime}$ and $R^{3\prime}$ are connected to each other to form a ring structure which is an aromatic ring. In addition, in this case $R^{1\prime}$ and $R^{4\prime}$ do not exist.

If at least one of $R^{1\prime}$ to $R^{4\prime}$ is a silane compound containing a succinimide group that is an olefin group, hydrophobic group such as polyolefine and silicon is particularly preferably used. According to this, both of the heat resistance and the resistance to moisture absorption can be improved without a reduction in adhesion. The resin composition can be particularly preferably used as an adhesion for mounting a semiconductor, such as a die attachment film (DAF), a back-grinding film (BG), and a dicing tape (DC).

The resin composition of the invention contains an organic resin and the organic resin is preferably compounds having at least glycidyl and/or epoxy group, polyphenol compounds and maleimide compounds, and these compounds may be used alone or two or more of them may be used in combination. As described, the above-mentioned resin composition may be a resin composition (referred to also as resin composition (1)) containing a compound having at least glycidyl and/or epoxy group, a resin composition (referred to also as resin composition (2)) containing a polyphenol compound, and a resin composition (referred to also as resin composition (3)) containing maleimide compound and these resin compositions are also preferable embodiments of the invention.

Further, the organic resin preferably include, beside the above-mentioned resins, thermoplastic resins such as (modified) polyethylene type resins, (modified) polypropylene type resins, ABS type resins, AES type resins, AAS resins, methacrylic resins, polystyrene type resins, polyamide type resins (including thermoplastic polyamide type elastomers), thermoplastic polyurethane type resins (including thermoplastic polyurethane type elastomers), polyacetal type resins, polyphenylene ether type resins, modified polyphenylene ether type resins, polycarbonate type resins, polyester type resins (including thermoplastic polyester type elastomers), polysulfone type resins, polyether sulfone type resins, polyphenylene sulfide type resins, polyacrylate type resins, polyether ketone type resins, polyether ketone type resins, polyimide type resins, polyetherimide type resins, and polyamide imide type resins; and thermosetting resins such as melamine resins, guanamine resins, urea resins, xylene resins, polyurethane resins, alkyd resins, unsaturated polyester resins, epoxy(meth)acrylate resins, vinyl ether resins, bismaleimide-triazine resins, and polyaniline resins. If the resin composition is used as a thermosetting resin, it is preferable that a silane compound containing an imidopropyl group is dissolved into an organic resin containing any of an epoxy group, a glycidyl group, a phenol group, an unsaturated double bond-containing imide group. According to this, the heat resistance, the resistance to moisture absorption, the low dielectric characteristics can be more improved. Therefore, such a resin composition can be particularly preferably used as a thermosetting resin.

Hereinafter, compounds having at least epoxy and/or glycidyl group, polyphenol compounds, maleimide compounds, and resin compositions containing these compounds, which are preferably usable for the organic resin of the invention will be described.

The compounds having at least epoxy and/or glycidyl group are preferably the following compounds. Examples are high molecular weight epibis-type glycidyl ether epoxy resins obtained by addition reaction of epibis-type glycidyl ester epoxy resins, which are obtained by condensation reaction of bisphenols such as bisphenol A, bisphenol F, bisphenol S with epihalohydrin, with the above-mentioned bisphenols such as bisphenol A, bisphenol F, bisphenol S; novolak aralkyl type glycidyl ether epoxy resins obtained by condensation reaction of polyphenols, which are obtained by condensation reaction of phenols such as phenol, cresol, xylenol, naphthol, resorcin, catechol, bisphenol A, bisphenol F, bisphenol S with formaldehyde, acetaldehyde, propionaldehyde, benzaldehyde, hydroxybenzaldehyde, salicylaldehyde, dicyclophetadiene, terpene, coumarin, p-xylene glycol dimethyl ether, dichloro-p-xylylene and bis(hydroxymethyl)biphenyl with epihalohydrin; aromatic crystalline epoxy resins obtained by condensation reaction of tetramethylbisphenol, tetramethylbisphenol F, hydroquinone, naphthalene diol and epihalohydrin; and high molecular weight polymers of aromatic crystalline epoxy resins obtained by further addition reaction of the above-mentioned bisphenols as well as tetramethylbisphenol, tetramethylbisphenol F, hydroquinone, naphthalene diol; aliphatic glycidyl ether type epoxy resins obtained by condensation reaction of alicyclic glycols obtained by hydrogenating aromatic skeletons of the above-mentioned bisphenols as well as tetramethylbisphenol, tetramethylbisphenol F, hydroquinone, naphthalene diol, ethylene glycol, diethylene glycol, triethylene glycol, tetraethylene glycol, PEG 600, propylene glycol, dipropylene glycol, tripropylene glycol, tetrapropylene glycol, polypropylene glycol, PPG, glycerol, diglycerol, tetraglycerol, polyglycerol, trimethylol propane and its polymer, pentaerythritol and its polymers, mono/polysaccharides such as glucose, fructose, lactose, and maltose with epihalohydrin; epoxy resins having skeletons of epoxycyclohexane such as (3,4-epoxycyclohexane)methyl 3',4'-epoxycyclohexylcarboxylate; glycidyl ester type epoxy resins obtained by condensation reaction of tetrahydrophthalic acid, hexahydrophthalic acid, benzoic acid with epihalohydrin; and tertiary amine-containing glycidyl ether type epoxy resins in solid-phase at room temperature obtained by condensation reaction of hydantoin, cyanuric acid, melamine, benzoguanamine, and the like with epihalohydrin. Especially, the above-mentioned aliphatic glycidyl ether type epoxy resins and epoxy resins having the epoxycyclohexane skeleton are more preferably usable for suppressing the apparent deterioration at the time of light radiation.

In the resin composition (1), in the case the total weight of the organic resin and the silane compound (if a curing agent is used, the total weight of the organic resin, the silane compound, and the curing agent) is set to be 100% by weight, the content of the above-mentioned silane compound is preferably 3% by weight in the lower limit, more preferably 10% by weight, and even more preferably 15% by weight. The upper limit is preferably 80% by weight, more preferably 70% by weight, and even more preferably 60% by weight.

With respect to the content of the glycidyl and/or epoxy group-containing compound in the resin composition (1), in the case the total weight of the organic resin and the silane compound (if a curing agent is used, the total weight of the organic resin, the silane compound, and the curing agent) is set to be 100% by weight, the lower limit is preferably 10% by weight, more preferably 20% by weight, and even more preferably 30% by weight. The upper limit is preferably 95% by weight, more preferably 90% by weight, and even more preferably 85% by weight.

With respect to the epoxy equivalent in the above-mentioned resin composition (1), the lower limit is preferably 100 g/mol, more preferably 120 g/mol, and even more preferably 150 g/mol. The upper limit is preferably 450 g/mol, more preferably 420 g/mol, and even more preferably 400 g/mol.

With respect to the viscosity of the above-mentioned resin composition (1) at 25° C. or 60° C., the lower limit is preferably 1200 mPa·s, more preferably 1500 mPa·s, and even more preferably 1800 mPa·s. The upper limit is preferably 4200 mPa·s, more preferably 4000 mPa·s, and even more preferably 3800 mPa·s.

With respect to the heat softening temperature of the above-mentioned resin composition (1), the lower limit is preferably 45° C. and more preferably 70° C. The upper limit is preferably 200° C. and more preferably 150° C.

With respect to the melting point, the lower limit is preferably 80° C. and more preferably 100° C. The upper limit is preferably 300° C. and more preferably 250° C.

The above-mentioned resin composition may contain an additive besides the above-mentioned constituent elements such as a stabilizer, a release agent, a coupling agent, a coloring agent, a plasticizer, a diluent such as reactive diluent, a flexing agent, various kinds of rubber-like materials, a photosensitizing agent, a filler, a flame-retardant, and a pigment.

The above-mentioned resin composition (1) gives a cured article by thermosetting with a curing agent.

The above-mentioned curing agent may be one or more compounds, for example, acid anhydrides such as methyltetrahydrophthalic acid anhydride, hexahydrophthalic acid anhydride, dehydrated methylhexahydrophthalic acid, pyromellitic anhydride, and methylnadic acid; various kinds of phenol resins such as phenol novolak resin, cresol novolak resin, bisphenol A novolak resin, dicyclopentadiene phenol resin, phenol aralkyl resin, and terpene phenol resin; various kinds of phenol resins such as polyphenol resins obtained by condensation reaction of various phenols and various aldehydes such as hydroxybenzaldehyde, croton aldehyde, and glyoxal; $BF_3$ complex, sulfonium salts, and imidazoles.

For the above-mentioned curing, a curing promoting agent may be used and for example, one or more organic phosphorus compounds such as triphenylphosphine, tributylhexadecylphosphonium bromide, tributylphosphine, and tris(dimethoxyphenyl)phosphine are preferable.

Temperature of the above-mentioned curing is preferably 70 to 200° C. and more preferably 80 to 150° C. The curing time is preferably 1 to 15 hours and more preferably 5 to 10 hours.

Examples of cured articles to be obtained in the above-mentioned manner are molded bodies such as articles with irregular shapes, films, sheets, and pellets and a cured article obtained using the resin composition (1) of the invention is one of preferable embodiments of the invention. The resin composition (1) which can be cured is also referred to as a curable resin composition (1).

The above-mentioned resin composition (1) is preferably usable for, for example, mechanical part materials, electric and electronic part materials, part materials of vehicles, ships and aircrafts, civil engineering and construction materials, molding materials, and materials for coatings and adhesives. Practically, the composition is preferably usable for printed wiring boards, build-up type wiring boards, solder resist, laminate plates, materials for light emitting diodes (LED), seal materials for liquid crystal displays and organic electroluminescent devices (organic EL), materials for semiconductor devices, materials relevant to civil engineering such as fiber-reinforced plastics (FRP), injection materials, adhesives, and raw materials for electric insulation coatings, and a semiconductor device or a printed wiring board comprising a cured article of the resin composition (1) is also one of preferable embodiments of the invention.

Polyphenols suitable as the organic resin contained in the resin composition (2) (referred to also as non-flammable resin composition) of the invention will be described. Examples to be preferably used as the above-mentioned polyphenol compounds are those having a structure formed by connecting aromatic skeletons having at least one phenolic hydroxyl group via an organic skeleton of 2 or more carbon atoms. In the above-mentioned polyphenol compounds, the aromatic skeletons are aromatic rings having at least one phenolic hydroxyl group. The aromatic skeletons are portions having phenol type structure and phenol type, hydroquinone type, naphthol type, anthracenyl type, bisphenol type, and biphenol type are preferable. Especially, phenol type is preferable. Further, the portions having phenol type structure may be properly substituted with alkyl, alkylene, aralkyl, phenyl, and phenylene group.

In the above-mentioned polyphenol compounds, the organic skeleton means a portion indispensably comprising carbon atoms and connecting aromatic ring skeletons composing the polyphenol compounds. Further, the organic skeleton having two or more carbon atoms is preferable to have a ring structure. The ring structure means a structure having a ring such as aliphatic rings and aromatic rings, and preferable rings are cyclopentane ring, cyclohexane ring, benzene ring, naphthalene ring, and anthracene ring. Further, the organic skeleton is preferable to have a nitrogen atom-containing ring structure such as triazine ring and phosphazene ring and/or an aromatic ring, and even more preferable to have a triazine ring and/or an aromatic ring. The polyphenol compounds may have another aromatic skeleton and organic skeleton other than those described above and may simultaneously have a structure formed by connecting aromatic skeletons each having at least one phenolic hydroxyl group through an organic skeleton (methylene) having 1 carbon atom.

The above-mentioned polyphenol compounds are preferable to have a nitrogen atom content of 1 to 50% by weight in the case the compounds have a nitrogen atom-containing ring structure as an organic skeleton. If it is less than 1% by weight, non-flammability of molding materials for electronic materials, adhesives, and coating materials possibly becomes insufficient, and if it exceeds 50% by weight, it may possibly become difficult to simultaneously satisfy the physical properties and non-flammability. It is more preferably 3 to 30% by weight and even more preferably 5 to 20% by weight. The nitrogen atom content means the weight ratio of nitrogen atoms composing a polyphenol compound in the case the weight of the polyphenol compound is set to be 100% by weight.

The polyphenol compounds to be used in the invention are preferably those which are produced from reaction raw materials which indispensably contain a compound forming an aromatic skeleton having at least one phenolic hydroxyl group (hereinafter, referred to also as a compound forming an aromatic skeleton) and a compound forming an organic skeleton of 2 or more carbon atom(s) (hereinafter, referred to also as a compound forming an organic skeleton).

The above-mentioned reaction raw materials mean mixtures containing a compound forming an aromatic skeleton and a compound forming an organic skeleton as indispensable components and optionally another compound, and further a solvent to be optionally used for reaction. One or more compounds may be used respectively for forming an aromatic skeleton and forming an organic skeleton.

The above-mentioned compounds for forming an aromatic skeleton may be compounds comprising an aromatic ring and one or more phenolic hydroxyl groups, and optionally one or more substituent(s) other than hydroxyl group. Examples of the above-mentioned compounds for forming an aromatic skeleton are preferably phenol, o-cresol, m-cresol, p-cresol, o-ethylphenol, p-ethylphenol, mixed cresol, p-hydroxyethylphenol, p-n-propylphenol, o-isopropylphenol, p-isopropylphenol, mixed isopropylphenol, o-sec-butylphenl, m-tert-butylphenol, p-tert-butylphenol, pentylphenol, p-octylphenol, p-nonylphenol, 2,3-dimethylphenol, 2,4-dimethylphenol, 2,6-dimethylphenol, 3,4-dimethylphenol, 2,4-di-sec-butylphenol, 3,5-dimethylphenol, 2,6-di-sec-butylphenol, 2,6-di-tert-butylphenol, 3-methyl-4-isopropylphenol, 3-methyl-5-isopropylphenol, 3-methyl-6-isopropylphenol, 2-tert-butyl-4-methylphenol, 3-methyl-6-tert-butyphenol, and 2-tert-butyl-4-ethylphenol. Examples of compounds having two or more phenolic hydroxyl groups are preferably catechol, resorcin, biphenol, bisphenol A, bisphenol S, and bisphenol F and also compounds forming a polycyclic aromatic skeleton such as α-naphthol and β-naphthol are preferable.

The above-mentioned compounds forming an organic skeleton are preferably (1) aromatic compounds having α-hydroxyalkyl, α-alkoxyalkyl or α-acetoxyalkyl, (2) compounds having an unsaturated bond, (3) compounds having carbonyl group such as aldehydes and ketones, (4) compounds having two or more of these specified active groups or active portions, and (5) compounds having amino group, hydroxyalkylamino group, or di(hydroxyalkyl)amino group.

Examples of the above-mentioned aromatic compounds (1) are preferably p-xylylene glycol, o-xylylene glycol dimethyl ether, p-diacetoxymethylbenzene, m-xylylene glycol, m-xylylene glycol dimethyl ether, m-diacetoxymethylbenzene, p-dihydroxyisopropylbenzene, p-dimethoxyisopropylbenzene, p-diacetoxyisopropylbenzene, trihydroxymethylbenzene, trihydroxyisopropylbenzene, trimethoxymethylbenzene, trimethoxyisopropylbenzene, 4,4'-hydroxymethylbiphenyl, 4,4'-methoxymethylbiphenyl, 4,4'-acetoxymethylbiphenyl, 3,3'-hydroxymethylbiphenyl, 3,3'-methoxymethylbiphenyl, 3,3'-acetoxymethylbiphenyl, 4,4'-hydroxyisopropylbiphenyl, 4,4'-methoxyisopropylbiphenyl, 4,4'-acetoxyisopropylbiphenyl, 3,3'-hydroxyisopropylbiphenyl, 3,3'-methoxyisopropylbiphenyl, 3,3'-acetoxyisopropylbiphenyl, 2,5-hydroxymethylnaphthalene, 2,5-methoxymethylnaphthalene, 2,5-acetoxymethylnaphthalene, 2,6-hydroxymethylnaphthalene, 2,6-methoxymethylnaphthalene, 2,6-acetoxymethylnaphthalene, 2,5-hydroxyisopropylnaphthalene, 2,5-methoxyisopropylnaphthalene, 2,5-acetoxyisopropylnaphthalene, 2,6-hydroxyisopropylnaphthalene, 2,6-methoxyisopropylnaphthalene, and 2,6-acetoxyisopropylnaphthalene.

Examples of the above-mentioned compounds having an unsaturated bond (2) are preferably divinylbenzene, diisopropenylbenzene, trivinylbenzene, triisopropenylbenzene, dicyclopentadiene, norbornene, and terpene. Examples of the above-mentioned compounds having carbonyl (3) are preferably various kinds of aldehydes and ketones having 5 to 15 carbon atoms and benzaldehyde, octanal, cyclohexanone, acetophenone, hydroxybenzaldehyde, hydroxyacetophenone, crotonaldehyde, cinnamaldehyde, glyoxal, glutalaldehyde, terephthalaldehyde, cyclohexanedialdehyde, tricyclodecanedialdehyde, norbornanedialdehyde, and suberaldehyde.

In the compounds having two or more of specified active groups or active portions (4), compounds having carbonyl and an unsaturated bond are preferably isopropenylbenzaldehyde, isopropenylacetophenone, citronellal, citral, and perylaldehyde. Further, compounds having α-hydroxyalkyl or α-alkoxyalkyl group as well as an unsaturated bond are dihydroxymethylstyrene, dihydroxymethyl-α-methylstyrene, dimethoxymethylstyrene, dimethoxymethyl-α-methylstyrene, hydroxymethyldivinylbenzene, hydroxymethyldiisopropylbenzene, methoxymethyldivinylbenzene, and methoxymethyldiisopropylbenzene.

Examples of the compounds having amino group, hydroxyalkylamino group, or di(hydroxyalkyl)amino group (5) are preferably melamine, dihydroxymethylmelamine, trihydroxymethylmelamine, acetoguanamine, dihydroxymethylacetoguanamine, tetrahydroxymethylacetoguanamine, benzoguanamine, dihydroxymethylbenzoguanamine, tetrahydroxymethylbenzoguanamine, urea, dihydroxymethylurea, tetrahydroxymethylurea, ethylenediamine, dihydroxymethylethylenediamine, tetrahydroxymethylethylenediamine, hexaethylenediamine, dihydroxymethylhexaethylenediamine, tetrahydroxymethylhexaethylenediamine, p-xylylenediamine, p-dihydroxymethylaminobenzene, m-xylylenediamine, m-dihydroxymethylaminobenzene, 4,4'-methylenedianiline, and 4,4'-methylenedihydroxymethylaniline. Among them are compounds having triazine skeleton such as melamine, benzoguanamine, and acetoguanamine preferable.

The above-mentioned reaction raw materials preferably include a compound forming an aromatic skeleton (hereinafter, referred to also as raw material A) and a compound forming at least one organic skeleton selected from the above-mentioned compounds (1) to (5) (hereinafter, referred to also as raw material B) as indispensable components, and more preferably include the raw material. A, a compound forming at least one organic skeleton selected from the above-mentioned compounds (1) to (4) (hereinafter, referred to also as raw material B1), and compound forming at least one organic skeleton (5) (hereinafter, referred to also as raw material B2) as indispensable components. With respect to the reaction order of the reaction raw materials in this case, it is preferable to previously mix the raw material A, raw material B1, and raw material B2 before starting the reaction and to cause reaction of the raw material B2 before the reaction of the raw material A and raw material B1 is completed and for example, it is preferable that the raw material A, raw material B1, and raw material B2 are simultaneously reacted or the raw material A and raw material B2 are reacted in the first stage and thereafter the raw material B1 is further reacted in the second stage. Accordingly, the non-flammability is reliably improved and the obtained product is made more preferably suitable for molding materials for electronic materials, adhesives, and coating material. It is more preferable that after the raw material A and raw material B2 are reacted in the first stage, the raw material B1 is further reacted in the second stage.

The mixing mole ratio of the raw material A and raw material B to be used in the case of producing the above-mentioned polyphenol compounds is preferably 1/1 or higher and 10/1 or lower. If the raw material A is less than 1/1, gelation occurs at the time of producing the resin composition of the invention, and if the raw material A is more than 10/1, it may possibly become difficult to exhibit the non-flammability of the resin composition. The ratio is more preferably 1.3/1 or higher and 8/1 or lower since the resin composition can exhibit high strength at a high temperature. The ratio is furthermore preferably 1.8/1 or higher and 5/1 or lower.

The above-mentioned polyphenol compounds are preferable to be produced by reaction of the above-mentioned reaction raw materials in the presence of a catalyst. A catalyst to be used in the production of the polyphenol compounds may be any if it can promote reaction of the above-mentioned reaction raw materials. In the case of reaction of the raw material B1 using the catalyst, preferable catalysts as an acid catalyst are inorganic acids and organic sulfonic acids such as hydrochloric acid, sulfuric acid, phosphoric acid, p-toluenesulfonic acid, and methanesulfonic acid, and super strong acid such as boron trifluoride and its complexes, trifluoromethanesulfonic acid, heteropolyacid, activated white clay, solid acid catalysts such as activated white clay, synthetic zeolite, sulfonic acid type ion exchange resin, and perfluoroalkanesulfonic acid type ion exchange resin. In the case of reaction of the above-mentioned raw material B1, the use amount of the catalyst may be properly set in accordance of the respective acid strength, however, it is preferably 0.001 to 100% by weight based on that of the raw material B1. As a catalyst for a homogeneous system in the above-mentioned range, trifluoromethanesulfonic acid, methanesulfonic acid, and boron trifluoride are preferable, and use amount of these catalysts is preferably 0.001 to 5% by weight. The use amount of ion exchange resin and activated white clay of a heterogeneous system is preferably 1 to 100% by weight.

In the case of reaction of the raw material B2 using the above-mentioned catalysts, examples of basic catalysts are preferably hydroxides and oxides of alkali metals and alkaline earth metals such as sodium hydroxide, potassium hydroxide, and barium hydroxide, ammonia, primary to tertiary amines, hexamethylenetetramine, and sodium carbonate, and examples of acid catalysts are inorganic acids such as hydrochloric acid, sulfuric acid and sulfonic acid, organic acids such as oxalic acid and acetic acid, and divalent metal salt type basic catalyst such as Lewis acid and zinc acetate. In the case the resin composition of the invention is used for an epoxy resin curing agent for electric and electronic materials, since it is not preferable that inorganic substances such as metals remain as catalyst residues, it is preferable to use amines as the basic catalysts and organic acids as acidic catalysts.

Further, if necessary, after the reaction of the raw material B2, it is preferable to remove impurities of salts and the like by neutralization and washing with water. In addition, in the case amines are used as the catalysts, it is preferable not to carry out impurity removal by neutralization or washing with water and the like.

The above-mentioned polyphenol compounds are obtained by condensation of an aromatic ring of the raw material A and a substituent of the raw material B, and at that time, together with the polyphenol compounds, carboxylic acid, alcohol, and water and the like are produced as byproducts. The carboxylic acid, alcohol, and water produced as byproducts can easily be removed from the reaction products by distillation in reduced pressure during reaction or after the reaction or azeotropic boiling with a solvent with no need of complicated process. The reaction products mean mixtures containing all produced by the reaction described above and contain the polyphenol compounds, carboxylic acid, alcohol, and water produced as byproducts, and the catalyst optionally used, and also a solvent which will be described later.

With respect to the reaction conditions for the production of the above-mentioned polyphenol compounds, the reaction temperature is preferable to be adjusted at a temperature for evaporating and removing the carboxylic acid, alcohol, and water produced as byproduct and preferably 100 to 240° C., more preferably 110 to 180° C., and even more preferably 130 to 160° C. As described, in the production of the polyphenol compounds, carboxylic acid or the like is produced as a byproduct, however, it can easily be removed from the reaction products. Although depending on the raw materials to be used, the type and amount of the catalyst, and the reaction temperature, the reaction time is preferably until the time when the reaction of the raw material A and raw material B is substantially completed, that is, until the time when carboxylic acid, alcohol, or water is note produced and thus it is preferably 30 minutes to 24 hours and more preferably 1 to 12 hours.

With respect to a reaction method in the production of the above-mentioned polyphenol compounds, the reaction may be carried out in the presence of a solvent and as the solvent, it is preferable to use an organic solvent which is inactive on the reaction with the raw material A and raw material B, and toluene, xylene, monochlorobenzene, and dichlorobenzene and the like may be used. Use of the solvent makes the raw materials dissolved therein and homogeneous. In the case of reaction of the raw material B1, it is preferable to carry out the reaction in absence of a solvent.

In the case of production of the above-mentioned polyphenol compounds, when the byproducts such as the carboxylic acid, alcohol, and water are removed from the reaction products, it is preferable to remove them by distillation at the above-mentioned temperature under reduced pressure of 0.1 to 10 kPa. At that time, since un-reacted phenols may possibly be distilled, it is preferable to carry out the removal after the reaction is substantially completed.

The resin composition of the invention (resin composition (2)) is preferable to contain a silane compound dispersed in an organic resin, and a production method of the composition is preferable a method of mixing the organic resin and the above-mentioned silane compound after they are respectively produced.

With respect to the above-mentioned resin composition (2), it is preferable to contain the silane compound in the resin composition (2) in an amount of 3% by weight or more and 80% by weight or less in the case the total weight of the organic resin and the silane compound (if a curing agent is used, the total weight of the organic resin, the silane compound, and the curing agent) is set to be 100% by weight. If it is less than 3% by weight, it may be impossible to obtain excellent non-flammability and if it exceeds 80% by weight, it may possibly lower the handling property and deteriorate the moldability. It is more preferably 5% by weight or higher and 50% by weight or lower.

With respect to the above-mentioned resin composition (2), the content of a polyphenol compound is preferably 10% by weight as the lower limit, more preferably 20% by weight, and even more preferably 30% by weight in the case the total weight of the organic resin and the silane compound (if a curing agent is used, the total weight of the organic resin, the silane compound, and the curing agent) is set to be 100% by weight. The upper limit is preferably 95% by weight as the lower limit, more preferably 90% by weight, and even more preferably 85% by weight.

The thermal softening temperature of the resin composition (2) of the invention is preferably 45° C. or higher and 200° C. or lower, and more preferably 70° C. or higher and 150° C. or lower. Further, the hydroxyl value of the above-mentioned resin composition (2) is preferably 100 g/mol or higher and 280 g/mol or lower, and more preferably 120 g/mol or higher and 240 g/mol or lower.

At the time of using the resin composition (2) of the invention for preparing a curable resin composition (2) which will be described later, it is sometimes better to use the composition in form of a solution, varnish, or paste. In this case, it is required to disperse the silane compound and the polyphenol together and give good fluidity. The resin composition (2) in such a usable embodiment is preferable to contain a compound having at least one or more structures selected from ether bond, ester bond, and nitrogen atom as a solvent, a plasticizer, and a lubricant.

Examples of the above-mentioned compound having ether bond are preferably diethyl ether, dipropyl ether, diisopropyl ether, dibutyl ether, dihexyl ether, ethyl vinyl ether, butyl vinyl ether, anisole, phenetole, butyl phenyl ether, pentyl phenyl ether, methoxytoluene, benzyl ethyl ether, diphenyl ether, dibenzyl ether, veratrol, propylene oxide, 1,2-epoxybutane, dioxane, trioxane, furan, 2-methylfuran, tetrahydrofuran, tetrahydropyrane, cineol, 1,2-dimethoxyethane, 1,2-diethoxyethane, 1,2-dibutoxyethane, glycerin ether, crown ether, methylal, acetal, methyl cellosolve, ethyl cellosolve, butyl cellosolve, ethylene glycol monopropyl ether, ethylene glycol monohexyl ether, ethylene glycol dimethyl ether, diethylene glycol, diethylene glycol methyl ether, diethylene glycol ethyl ether, diethylene glycol butyl ether, diethylene glycol dimethyl ether, diethylene glycol diethyl ether, diethylene glycol dibutyl ether, triethylene glycol, triethylene glycol monomethyl ether, tetraethylene glycol, 1-methoxy-2-propanol, 1-ethoxy-2-propanol, propylene glycol methyl ether, propylene glycol dimethyl ether, propylene glycol propyl ether, propylene glycol butyl ether, dipropylene glycol, dipropylene glycol monomethyl ether, dipropylene glycol monoethyl ether, dipropylene glycol dimethyl ether, dipropylene glycol diethyl ether, dipropylene glycol dibutyl ether, tripropylene glycol, tripropylene glycol monomethyl ether, 2-methoxyethanol, 2-ethoxyethanol, 2-(methoxymethoxy)ethanol, 2-isopropoxyethanol, 2-butoxyethanol, 2-(isopentyloxy)ethanol, 2-(hexyloxy)ethanol, 2-phenoxyethanol, 2-(benzyloxy)ethanol, furfuryl alcohol, and tetrahydrofurfuryl alcohol.

Examples of the above-mentioned compound having ester bond are preferably methyl formate, ethyl formate, propyl formate, butyl formate, isobutyl formate, pentyl formate, methyl acetate, ethyl acetate, propyl acetate, isopropyl acetate, butyl acetate, isobutyl acetate, sec-butyl acetate, pentyl acetate, isopentyl acetate, 3-methoxybutyl acetate, sec-hexyl acetate, 2-ethylbutyl acetate, 2-ethylhexyl acetate, cyclohexyl acetate, benzyl acetate, methyl propionate, ethyl propionate, butyl propionate, isopentyl propionate, ethylene glycol monoacetate, diethylene glycol monoacetate, monoacetin, diacetin, triacetin, monobutylin, dimethyl carbonate, diethyl carbonate, dipropyl carbonate, dibutyl carbonate, butyric acid esters, isobutyric acid esters, isovaleric acid esters, stearic acid esters, benzoic acid esters, cinnamic acid esters, abietic acid esters, adipic acid esters, γ-butyrolactones, oxalic acid esters, malonic acid esters, maleic acid esters, tartaric acid esters, citric acid esters, sebacic acid esters, phthalic acid esters, and ethylene diacetate and the like.

Examples of the above-mentioned compound containing nitrogen atom are preferably nitromethane, nitroethane, 1-nitropropane, 2-nitropropane, nitrobenzene, acetonitrile, propionitrile, succinonitrile, butyronitrile, isobutyronitrile, valeronitrile, benzonitrile, α-tolunitrile, formamide, N-methylformamide, N,N-dimethylformamide, N,N-diethylformamide, acetamide, N-methylacetamide, N,N-dimethylacetamide, N,N-diethylacetamide, 2-pyrrolidone, N-methylpyrrolidone, and ∈-caprolactam and the like.

Examples of compounds having a plurality of structures selected from the group consisting of ether bonds, ester bond, and nitrogen atom are preferably N-ethylmorpholine, N-phenylmorpholine, methyl cellosolve acetate, ethyl cellosolve acetate, propyl cellosolve acetate, butyl cellosolve acetate, phenoxyethyl acetate, diethylene glycol monomethyl ether acetate, diethylene glycol monoethyl ether acetate, diethylene glycol monopropyl ether acetate, diethylene glycol monobutyl ether acetate, propylene glycol methyl ether acetate, propylene glycol ethyl ether acetate, propylene glycol propyl ether acetate, propylene glycol butyl ether acetate, dipropylene glycol methyl ether acetate, dipropylene glycol ethyl ether acetate, dipropylene glycol propyl ether acetate, dipropylene glycol butyl ether acetate, and tripropylene glycol methyl ether acetate and the like.

The use amount of the compounds having at least one structure selected from the group consisting of ether bonds, ester bond, and nitrogen atom is preferably 5 parts by weight or more and 1000 parts by weight or less based on 100 parts by weight of the resin composition. It is more preferably 10 parts by weight or more and 300 parts by weight or less.

The resin composition (2) of the invention can be used as a curable resin composition for semiconductor encapsulating materials and insulating materials for wiring boards (curable nonflammable resin composition) while being mixed with a compound having at least two glycidyl groups or another additive. The curable resin composition of the invention is a composition containing the above-mentioned polyphenol compound, the above-mentioned silane compound, and the compound having at least two glycidyl groups and can be obtained by a method of mixing the above-mentioned composition containing the polyphenol compound and silane compound with the compound having at least two glycidyl groups and also by mixing the above-mentioned polyphenol compound and the above-mentioned silane compound simultaneously with the compound having at least two glycidyl groups or by mixing a mixture of the silane compound dispersed in the compound having at least two glycidyl groups with the above-mentioned polyphenol compound. As described, the curable resin composition for semiconductor encapsulating materials and insulating materials for wiring boards which contains the resin composition (2) of the invention and the compound having at least two glycidyl group is also one of preferable embodiments of the invention.

Further, the above-mentioned curable resin composition (2) can form a molded body by being cured. In such a manner, a molded body obtained by curing the curable resin composition of the invention, a semiconductor devices obtained by sealing and curing a semiconductor encapsulating material of the invention, and an electric wiring board obtained by curing an insulating material for wiring boards of the invention are also included in preferable embodiments of the invention.

The above-mentioned compound having at least two glycidyl groups is preferably epoxy resins having 2 or more glycidyl groups in average per one molecule, and preferable examples are epibis type glycidyl ether epoxy resins obtained by condensation reaction of bisphenols such as bisphenol A, bisphenol F, and bisphenol S with epihalohydrin; novolak aralkyl type glycidyl ether epoxy resins obtained by further carrying out condensation reaction of polyphenols, which are obtained by reaction of phenols such as phenol, cresol, xylenol, resorcin, catechol, bisphenol A, and bisphenol F with formaldehyde, acetaldehyde, propionaldehyde, benzaldehyde, salisylaldehyde, dicyclopentadiene, terpene, coumarin, p-xylylene dimethyl ether, and dichloro-p-xylene, with epihalohydrin; glycidyl ester type epoxy resins obtained by condensation reaction of tetrahydrophthalic acid, hexahydrophthalic acid, and benzoic acid with epihalohydrin; glycidyl ether type epoxy resins obtained by condensation reaction of hydrogenated bisphenol and glycols with epihalohydrin; amine-containing glycidyl ether type epoxy resins obtained by condensation reaction of hydantoin and cianuric acid with epihalohydrin; and aromatic polycyclic epoxy resins such as biphenyl type epoxy resins and naphthalene type epoxy resins. Examples of the compound may also include compounds having epoxy group in a molecule by addition reaction of these epoxy resins with polybasic acids and/or bisphenols. These compounds may be used alone or two or more compounds may be used in combination.

The mixing ratio by weight of the above-mentioned resin composition (2) and the epoxy resin (resin composition (2)/epoxy resin) is preferable to be 30/70 or higher and 70/30 or lower. If it is less than 30/70, the mechanical physical property and the like of a formed cured article tends to be decreased, and if it exceeds 70/30, the non-flammability may possibly become insufficient. It is more preferably 35/65 or higher and 65/35 or lower.

The above-mentioned mixture may contain another additive and examples of another additive are a curing promoting agent, a filler, a coupling agent, a flame-retardant, a plasticizer, a reactive diluent, and a pigment.

Preferable examples of the curing promoting agent are imidazoles such as 2-methylimidazole and 2-ethyl-4-methylimidazole; amines such as 2,4,6-tris(dimethylaminomethyl)phenol, benzylmethylamine, DBU (1,8-diazabicyclo [5,4,0]-7-undecene), DCMU (3-(3,4-dichlorophenyl)-1,1-dimethylurea) and organic phosphorus compounds such as tributylphosphine, triphenylphosphine, tris(dimethoxyphenyl)phosphine.

Further, as described above, the above-mentioned resin composition (2) may be mixed with an epoxy resin in a state of a solution, varnish, or paste with fluidity to give a curable resin composition in form of an ink, coating material, or varnish. In this case, after being used as an ink, coating material, or varnish, the compound having at least one structure selected from the group consisting of the ether bond, ester bond, and nitrogen atom may be removed by drying under reduced pressure and/or heating to produce a rectangular product made of the resin composition (2). The drying condition of the ink and coating material may be properly adjusted in accordance with the vapor pressure or the boiling point of the employed compound having at least one structure selected from the group consisting of the ether bond, ester bond, and nitrogen atom. In the case varnish is employed for impregnation, fibrous reinforcing materials may be used as object bodies to be impregnated.

The above-mentioned reinforcing materials to be used may be conventionally known reinforcing materials, and examples are woven fabrics or non-woven fabrics of glass fibers of N type, NE type, S type, T type, D type glass, inorganic materials such as quartz, and organic materials. They may be used in form of glass roving cloths, glass cloths, chopped glass, hollow glass fibers, glass mats, glass-surface mats, glass non-woven fabrics, ceramic fiber textiles (woven fabrics, etc.), and metal fiber textiles. In addition, fillers for synthetic organic reinforcement such as organic polymers capable of forming fibers may be used for the invention. Typical examples of the reinforcing organic fibers are poly(ether ketone), polyimido benzoxazole, poly(phenylene sulfide), polyesters, aromatic polyamides, aromatic polyimides or polyether imides, acrylic resins, and poly(vinyl alcohol). Fluoropolymers such as polytetrafluoroethylene may be used in the invention. Further, as reinforcing materials, natural organic fibers known well by a person skilled in the art are made available, for example, there are cotton cloths, hemp cloths, felt, carbon fiber textiles, and natural cellulose textiles such as kraft paper and cotton paper, and glass fiber-containing paper. Such reinforcing fillers may be provided in form of monofilament or multifilament fibers and used alone or in combination of other type fibers by co-weaving or core/shell, side-by-side, orange-type, or matrix, and fibril construction or by a method which a person skilled in the fiber fabrication field has known well. Such fillers may be supplied in form of, for example, fiber reinforcing woven fabrics, non-woven fiber reinforcing materials, or paper.

The above-mentioned molded body is preferable to have flame retardancy of V-2 or higher by UL-94 standardized flame retardancy test. The flame retardancy of V-2 or higher by UL-94 standardized flame retardancy test sufficiently satisfies the inflammability required for molding materials for electronic materials, adhesives and coating materials.

The curable resin composition including the resin composition (the resin compositions (1) to (3) and others) of the present invention can be used as a sealing material such as semiconductor encapsulating material. Hereinafter, a case of using the curable resin composition of the invention as a sealing material will be described. The inorganic fillers, flame-retardants, other additives, etc. described below are preferably usable for the curable resin composition and may be used properly for the above-mentioned resin compositions, if necessary.

The curable resin composition of the invention may contain an inorganic filler for improving moisture absorption, suppressing linear expansion coefficient, increasing heat conductivity, and improving mechanical properties. Examples of inorganic fillers are powders of fused silica, crystalline silica, alumina, zircon, calcium silicate, calcium carbonate, calcium titanate, silicon carbide, silicon nitride, aluminum nitride, boron nitride, beryllia, zirconia, zircon, forsterite, steatite, spinel, mullite, and titania; beads obtained by making these materials spherical; and glass fibers. Further, examples of inorganic fillers effective for non-flammability are aluminum hydroxide, magnesium hydroxide, zinc borate and zinc molybdate. These inorganic fillers may be used alone or in combination of two or more of them. Among the above-mentioned inorganic fillers, fused silica is preferable in terms of suppressing linear expansion coefficient, alumina is preferable in terms of high heat conductivity, and the filler shape is preferably spherical in terms of the fluidity at the time of molding and mold wearing property. The addition amount of the inorganic fillers is preferably 70 parts by weight or more, more preferably 100 to 1000 parts by weight, and even more preferably 200 to 950 parts by weight based on 100 parts by weight of the curable resin composition of the invention in terms of the moldability, moisture absorption property, decrease of linear expansion coefficient, and strength improvement. If it is less than 70 parts by weight, the reflow resistance tends to be lowered, and if it exceeds 950 parts by weight, the fluidity tends to be insufficient.

As a flame retardant, conventionally known non-halogen and non-antimony type retardants may be used in combination for the curable resin composition of the invention.

Examples of the flame retardants are nitrogen-containing compounds such as cyanuric acid derivatives and isocyanuric acid derivatives, phosphorus/nitrogen-containing compounds such as cyclophosphazene, and metal compounds such as zinc oxide, iron oxide, molybdenum oxide, and ferrocene.

In terms of improvement of moisture resistance and high temperature-standing property of semiconductor devices such as IC, an anion exchanger may be added. The anion exchanger is not particularly limited and conventionally known ones may be used. Examples are hydrotalcites and hydrated oxides of elements selected from magnesium, aluminum, titanium, zirconium, and bismuth, and these compounds may be used alone or two or more of them in combination. Especially, hydrotalcite defined by the following general formula:

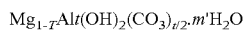

$$Mg_{1-T}Al_T(OH)_2(CO_3)_{T/2} \cdot m'H_2O$$

in the formula, $0 < T \leq 0.5$; and m' is a positive integer.

The curable resin composition of the invention may further contain, as other additives, a releasing agent such as higher fatty acids, higher fatty acid metal salts, ester type wax, polyolefin type wax, polyethylene, and polyethylene oxide; a coloring agent such as carbon black; and a stress moderating agent such as silicone oil and silicone rubber powder; if necessary.

In the case of being used as a sealing agent, the curable resin composition of the invention may be prepared by any means if the means can evenly disperse and mix the various raw materials; however, as general means, a method of sufficiently mixing prescribed amounts of raw materials by a mixer, thereafter melting and kneading the raw materials by mixing rolls or an extruder, and successively cooling and pulverizing the raw materials can be employed. If the raw materials are made to be tablets with a proper size and weight for molding conditions, handling is made easy.

Examples of electronic part apparatus to be obtained by sealing devices using the curable resin composition of the invention may be electronic part apparatus obtained by mounting elements, e.g. active elements such as semiconductor chips, transistors, diodes, thyristors, and so forth and passive elements such as capacitors, resistors, and coils on supporting members such as lead frames, already-wired tap carriers, wiring boards, glass, and silicon wafers, and sealing the necessary parts with the epoxy resin molding material for sealing of the invention. Examples of the electronic part apparatus may include common resin encapsulated type IC such as DIP (Dual Inline Package), PLCC (Plastic Leaded Chip Carrier), QFP (Quad Flat Package), SOP (Small Outline Package), SOJ (Small Outline J-lead package), TSOP (Thin Small Outline Package), and TQFP (Thin Quad Flat Package) obtained by fixing semiconductor devices on lead frames, connecting terminal parts of elements such as boning pads and lead parts by wire bonding and bumps and successively sealing the resulting elements by transfer molding using the curable resin composition of the invention. A TCP (Tape Carrier Package) obtained by sealing the semiconductor chips connected to tape carriers by bumps with the curable resin composition of the invention may be also mentioned. Further, examples there of include: electronic part apparatuses such as COB (Chip On Board) modules, hybrid IC, and multi chip modules obtained by sealing active elements such as semiconductor chips, transistors, diodes, and thyristors and/or passive elements such as capacitors; resistors, and coils, which are connected to wiring boards and wiring formed on glass by wire bonding, flip chip bonding, or soldering, with the curable resin composition of the invention; and electronic part apparatuses such as BGA (Ball Grid Array) and CSP (Chip Size Package) obtained by mounting elements on the front faces of organic substrates having terminals for wiring board connection in the rear faces, connecting the elements with the wirings formed on the organic substrates by bumps or wire bonding, and thereafter sealing the elements with the curable resin composition of the invention.

A method for sealing elements using the curable resin composition of the invention is most commonly a low pressure transfer molding method; however, an injection molding method and a compressive molding method may be employed.

Examples of electric wiring substrates to be obtained by diluting the curable resin composition of the invention with a solvent, if necessary; mixing the above-mentioned curing promoting agent, filler, flame retardant, and the like for obtaining an insulating material for wiring boards; impregnating various reinforcing materials with the insulating material or applying the insulating material to various kinds of substrates; drying and removing the solvent; and curing the insulating material may include one face or double face, or multilayered composite type laminate plates, glass-epoxy type laminate plates, aramide-epoxy type laminate plates, metal base wiring substrates, and build-up type wiring substrates.

The above-mentioned solvent is preferably those having at least one structure comprising the above-mentioned ether bonds, ester bonds, and nitrogen atoms and for optimization of the viscosity for impregnation and application process, or in accordance with the drying conditions, solvents may be used alone or two or more solvents may be used in form of a mixture. Fillers and flame retardants same as those used for the above-mentioned semiconductor encapsulating materials may be used.

As the reinforcing material, the above exemplified materials can be used and especially, woven fabrics and non-woven fabrics of glass fibers and polyaramide fibers are preferable and may be used alone or two or more of them may be used in combination.

The curable resin composition of the invention is also preferably usable for raw material of epoxy resin production; molding materials for molded products such as construction materials, housings, laminated plates, build up type wiring substrates, solder-resist, sealing materials (practically, sealing material for semiconductors), injection materials, machine parts, electron and electric parts, vehicles, ships, and aircrafts; and production raw materials such as adhesives and electric insulating coating materials.

A maleimide compound suitable as an organic resin contained in the resin composition (3) of the invention will be described. As a maleimide compound, all kinds of compounds having two or more maleimido groups in one molecule are usable. Monomaleimide compound has high toxicity and is therefore not preferable to be used in the invention.

Preferable examples of the above-mentioned maleimide compound include co-condensation products bismaleimides such as N,N'-ethylenebismaleimide, N,N'-hexamethylenebismaleimide, N,N'-m-phenylenebismaleimide, N,N'-p-phenylenebismaleimide, 2,2-bis[4-(4-maleimidophenoxy)phenyl]propane, bis[4-(4-maleimidophenoxy)phenyl]methane, 1,1,1,3,3,3-hexafluoro-2,2-bis[4-(4-maleimidophenoxy)phenyl]propane, N,N'-p,p'-diphenyldimethylsilylbismaleimide, N,N'-4,4'-diphenyl ether bismaleimide, N,N'-methylenebis(3-chloro-p-phenylene)bismaleimide, N,N'-4,4'-diphenylsulfonebismaleimide, N,N'-4,4'-dicyclohexylmethanebismaleimide, N,N'-dimethylenecyclohexanebismaleimide, N,N'-m-xylenebismaleimide, N,N'-4,4'-diphenylcyclohexanebismaleimide, and co-condensation compounds of N-phenylmaleimide and aldehyde compounds such as acetaldehyde, benzaldehyde, and hydroxyphenyl aldehyde. Further, preferable examples may include bismaleimide compounds defined by the following general formula:

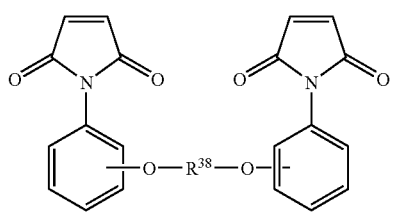

in the formula, $R^{38}$ denotes a divalent group

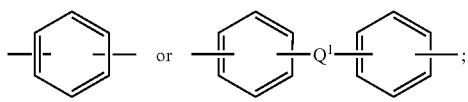

$Q^1$ is a group directly connected to two aromatic rings and denotes at least one group selected from the group consisting of divalent hydrocarbon groups having 1 to 10' carbon atom(s), hexafluorinated isopropylidene group, carbonyl group, thio group, sulfinyl group, sulfonyl group, and oxide group. Practically, preferable examples are 1,3-bis(3-maleimidophenoxy)benzene, bis[4-(3-maleimidophenoxy)phenyl]methane, 1,1-bis[4-(3-maleimidophenoxy)phenyl]ethane, 1,2-[4-(3-maleimidophenoxy)phenyl]ethane, 2,2-bis[4-(3-maleimidophenoxy)phenyl]propane, 2,2-bis[4-(3-maleimidophenoxy)phenyl]butane, 2,2-bis[4-(3-maleimidophenoxy)phenyl]-1,1,1,3,3,3-hexafluoropropane, 4,4-bis(3-maleimidophenoxy)biphenyl, bis[4-(3-maleimidophenoxy)phenyl]ketone, bis[4-(3-maleimidophenoxy)phenyl]sulfide, bis[4-(3-maleimidophenoxy)phenyl]sulfoxide, bis[4-(3-maleimidophenoxy)phenyl]sulfone, bis[4-(3-maleimidophenoxy)phenyl]ether, and compounds defined by the following general formula:

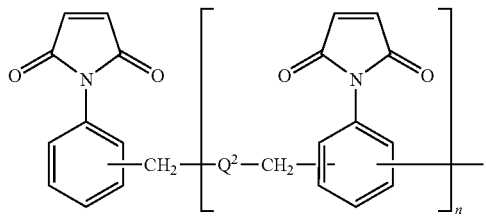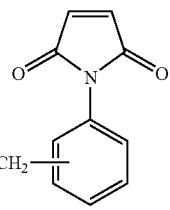

in the formula, $Q^2$ denotes a divalent group having an aromatic ring which may have a substituent; n denotes a repeating numeral of 0 to 10 in average). Practical examples of $Q^2$ are preferably divalent groups (phenylene, biphenylene, and naphthylidene groups and the like) of phenyl, biphenyl, and naphthyl groups and the like.

The above-mentioned maleimide compound is generally used while a conventionally known and employed crosslinking agent such as polyamines and aromatic amine compounds is added, and especially addition of an unsaturated compound having difference in electron density e value from that of the unsaturated bond of the maleimide forms a charge transporting complex and crosslinked structure to heighten the heat resistance and therefore, the addition is preferable.

The compound forming the charge transporting complex with the above-mentioned maleimide compound is preferably cyclic vinyl ethers represented by 6-ethoxy-2,2,4-trimethyl-1,2-dihydroquinoline, poly(2,2,4-trimethyl-1,2-dihydroquinoline), styrene, α-methylstyrene, trans-stilbene, vinylferrocene, 4-vinylpyridine, 2-isopropenylnaphthalene, N-vinylcarbazole, N-vinylindole, indole, benzofuran, furan, dihydrofuran, 3,4-dihydro-2-pyrane, and 4H-chromene; furan derivatives represented by furfuryl acetate; alkyl vinyl ethers represented by n-octadecyl vinyl ether and ethyl vinyl ether; ketones represented by ketene acetal, isopropenyl acetate, and 1-amino-1-methoxyethylene; esters, lactones, aldehydes, amides, enol ethers of carbonyl compounds such as lactams, enol esters, allyl acetate, vinyl acetate, 1,2-dimethoxyethylene, p-dioxene, 2-chloroethyl vinyl ether, 2-phenyl vinylalkyl ether, 2-phenyl alkenyl ether, heptafluoroisopropyl alkenyl ether, ethylvinyl sulfide, styryl alkenyl thioether, p-oxadiene, cyclopentine, cyclohexene, divinyl ether, butadiene, isoprene, 1,3-pentadiene, 1,4-pantadiene, and dimethyldivinylsilane.

The above-mentioned resin composition (3) is a composition containing a compound having maleimide groups. The resin composition (3) is not particularly limited if it contains a maleimide compound as an organic resin; however, the composition is preferable to contain other organic resin components in combination since the heat resistance can further be improved while the characteristics of other organic resins are maintained. The organic resins to be used in combination are preferably the above-mentioned compounds having at least one glycidyl and/or epoxy group and the above-mentioned polyphenol compounds. In the case these preferable organic resins are used in combination, the above-mentioned additives such as a curing agent may be used similarly.

With respect to the content of the organic resin in the above-mentioned resin composition (3), in the case the total weight of the organic resin and the silane compound (if a curing agent is used, the total weight of the organic resin, the silane compound, and the curing agent) is set to be 100% by weight, the lower limit value is preferably 20% by weight and more preferably 30% by weight. The upper limit value is preferably 97% by weight, more preferably 90% by weight, and even more preferably 80% by weight.

With respect to the content of the above-mentioned silane compound in the above-mentioned resin composition (3), in the case the total weight of the organic resin and the silane compound (if a curing agent is used, the total weight of the organic resin, the silane compound, and the curing agent) is set to be 100% by weight, the lower limit value is preferably 3% by weight, more preferably 10% by weight, and even more preferably 15% by weight. The upper limit value is preferably 80% by weight, more preferably 70% by weight, and even more preferably 60% by weight.

The content of the maleimide compound in the above-mentioned organic resin is preferably 2 to 100% by weight and more preferably 5 to 100% by weight based on 100% by weight of the organic resin.

The above-mentioned resin composition (3) (also referred to as a curable resin composition (3)) can be used preferably as a material excellent in processibility and heat resistance for the same uses as those of the above-mentioned resin compositions (1) and (2).

It is preferable that the above-mentioned resin composition is a thermosetting binder resin composition including a thermosetting resin and the above-mentioned silane compound. The above-mentioned silane compound essentially includes a structure unit formed by connecting at least one organic skeleton having an imido bond to a silicon atom forming a siloxane bond. According to this, the resin composition can exhibit more excellent characteristics such as heat resistance, weather resistance, moldability, pressure resistance and mechanical and chemical stability. Further, a thermosetting resin composition for bond magnets which includes this thermosetting binder resin composition and magnet powders essentially including a rare earth alloy can produce a bond magnet which hardly reduces physical properties such as magnetic characteristics even if a large share force is applied to the resin composition or the resin composition is molded under a high temperature and high pressure environment. For example, in a conventional bond magnet, if ferromagnetic metallics powders, especially rare earth magnet powders are kneaded with a resin binder to produce a bond magnet, the magnetic characteristics of the powders are deteriorated during heat molding process such as an injection molding and an extrusion molding, and thereby the coercive force is reduced. However, such a thermosetting binder resin composition including the thermosetting resin and the silane compound can sufficiently suppress the magnetic characteristics from being deteriorated due to the heat exposure during the molding process. Therefore, a bond magnet exhibiting excellent magnetic characteristics and the like can be produced. Further, such a thermosetting resin composition for bond magnets can produce a bond magnet which can be preferably used in various products such as electric appliances, communication facilities, and audio equipment, medical equipment, common industrial equipment, and electronic devices for automobiles. That is, a thermosetting binder resin composition which essentially includes an organic resin component including the above-mentioned thermosetting resin and which is used as a magnetic powder-binder forming a bond magnet, wherein the thermosetting binder resin contains the above-mentioned silane compound. In addition, the preferable embodiments of the present invention also include an embodiment in which the thermosetting resin composition for bond magnets, including the above-mentioned thermosetting binder resin composition and magnet powders essentially including a rare earth alloy.

The above-mentioned thermosetting binder resin composition essentially contains an organic resin component including a thermosetting resin and the above-mentioned silane compound. Such a thermosetting binder resin composition is excellent in heat resistance. If the composition is used as a magnetic powder-binder forming a bond magnet, a bond magnet having an excellent coercive force can be obtained without a reduction in the magnetic characteristics of the magnetic powders. In a conventional binder, if ferromagnetic metallics powders, specifically rare earth magnet powders, are kneaded with a resin binder and the mixture is subjected to a step of heat molding such as an injection molding and an extrusion molding, the magnetic characteristics of the magnetic powders are deteriorated and the coercive force is reduced. However, the use of the thermosetting binder resin composition of the present invention makes it possible to produce a bond magnet without deteriorating such characteristics.

The above-mentioned thermosetting binder resin composition essentially includes an organic resin component including a thermosetting resin. Examples of such a thermosetting resin include a compound at least one of a glycidyl group and an epoxy group, a polyphenol compound, and a maleimide compound. These compounds may be used singly or in combination of two or more species. Thus, the preferable embodiments of the present invention include embodiments in which the above-mentioned organic component includes a compound including at least one of a glycidyl group and an epoxy group (also referred to as an organic resin component (1)); the above-mentioned organic resin component includes a polyphenol compound (also referred to as an organic resin component (2)); the organic resin component includes a maleimide compound (also referred to as an organic resin component (3)).

In addition to the above-mentioned organic resins, thermosetting resins such as a melamine resin, a guanamine resin, a urea resin, a xylene resin, a polyurethane resin, an alkyd resin, a unsaturated polyester resin, a epoxy(meth)acrylate resin, a vinyl ether resin, a bismaleimide-triazine resin, and a polyaniline resin are excellent.

The content of the above-mentioned silane compound in the thermosetting binder resin composition is not especially limited as long as the silane compound is included in the thermosetting binder resin. It is preferable that the content of the silane compound is 3 to 80% by weight relative to the total solid content of the thermosetting binder resin composition. If the content of the silane compound is less than 3% by weight, the above-mentioned effects attributed to the added silane compound, such as an improvement in heat resistance, might not be sufficiently exhibited. If the content of the silane compound is tore than 80% by weight, the silane compound is not uniformly mixed with the resin component and therefore the performances might not be sufficiently exhibited. The content of the silane compound is more preferably 5 to 70% by weight and still more preferably 10 to 60% by weight. That is, the lower limit is 5%, and particularly preferably 10%. The upper limit is preferably 70% and particularly preferably 60%. The total solid content of the thermosetting binder resin component means a total weight of the organic resin component and the silane compound.

If the thermosetting binder resin composition including the above-mentioned silane compound is used for a bond magnet, the heat durability of the composition (the thermosetting resin composition for bond magnets) including magnetic powders essentially including a rare earth alloy (insoluble powders composed of a rare earth alloy) can be improved. The reason of the operation and effects in which the heat durability of the above-mentioned alloy magnetic powders is improved due to the mixing of the silane compound is because the silane compound is deposited on the magnetic particle surface. That is, if the silane compound contained in the thermosetting binder resin composition is deposited on the magnetic particle surface, the heat resistance degradation property of the thermosetting resin composition for bond magnets is improved and the magnetic characteristics are not deteriorated even if the composition is under a high temperature environment for a long time. Therefore, the thermosetting resin composition for bond magnets can be preferably used in various applications. That is, the preferable embodiments of the present invention include an embodiment in which the resin composition is a resin composition for bond magnets. The heat durability means a property in which the surface layer of the magnetic powder is oxidized under a high temperature environment, and thereby the magnetic characteristics are degraded. Such a heat durability can be evaluated based on an increase in a weight of the resin composition under a high temperature environment. In addition, such oxidization might cause deterioration of the mechanical characteristics of the bond magnet. If the above-mentioned resin composition is used to produce a bond magnet, it is preferable that the above-mentioned silane compound has a siloxane (—Si—O—Si) chain in the main chain and has a structure in which an organic component containing carbon is connected to the siloxane chain. That is, it is preferable that the above-mentioned silane compound is polysiloxane containing an organic group having an imide group. If the above-mentioned silane compound is polysiloxane, the heat resistance, pressure resistance, mechanical and chemical stability, and heat conductivity are more excellent and various characteristics such as heat resistance, excellent for various materials, can be provided. For example, if the structure such as a siloxane skeleton and an organic skeleton containing an imide bond is appropriately selected and thereby the silane compound shows a high solubility to various polymers, the polymers can be easily provide with a heat resistance, a pressure resistance, and the like. The polymers provided with a heat resistance, a pressure resistance and the like can form a cured article which hardly reduces various characteristics even in harsh environment such as a high temperature and a high pressure. Therefore, such a polymer can be preferably used in the bond magnet application and the like.

If the above-mentioned resin composition is used as a thermosetting resin composition for bond magnets, it is preferred to use a silane compound which more exhibits the effect of deposition to the magnetic powder surface, in an application which strongly needs the heat durability. In such an application, the embodiment in which the resin composition includes the silane compound is preferable because the above-mentioned deposition effect is excellent, although the degree of the effect depends on the molecular structure of the silane compound and the like.

In addition to the above-mentioned effect, the resin composition can exhibit a demolding effect because the resin composition includes the silane compound. Specifically, if the resin composition includes a thermosetting resin (particularly, an epoxy material) as the organic resin component, the thermosetting binder resin composition might adhere to a mold when the composition is cured, because the organic resin component has an adhesion effect. The resin composition containing an appropriate amount of the silane compound exhibits a demolding effect, and therefore a cured article of such a resin composition can be easily demolded. Therefore, such a resin composition is preferable for production of a bond magnet.

The preferable embodiments of the present invention include a thermosetting resin composition for bond magnets including the above-mentioned thermosetting binder resin composition and magnetic powders essentially including a rare earth alloy. Thus, if the resin composition essentially includes the thermosetting binder resin composition and the rare earth alloy, the heat resistance and the heat durability are improved and the powder magnetic characteristics are not reduced. Therefore, a bond magnet with excellent coercive force can be produced. The thermosetting resin composition for bond magnets in accordance with the present invention has these excellent effects, and therefore a bond magnet which can be preferably used in various products such as electric appliances communication facilities, and audio equipment, medical equipment, common industrial equipment, and electronic devices for automobiles can be produced. As mentioned above, the silane compound contained in the thermosetting binder resin composition is deposited on the surface of the magnetic powders essentially containing a rare earth alloy, and thereby the heat durability is exhibited.

Thus, the preferable embodiments of the present invention include a thermosetting resin composition for bond magnets containing a silane compound in the above-mentioned thermosetting bonder resin composition, or a thermosetting resin composition for bond magnets including the above-mentioned thermosetting binder resin composition (thermosetting binder resin composition) and rare earth alloy powders.

The above-mentioned magnetic powder essentially including a rare earth alloy is not especially limited as long as it includes a rare earth alloy and shows a magnetic property. That is, it is preferable that it includes at least an element of iron, cobalt, nickel, and manganese as an element having a magnetic property. That is, a powder of an alloy including a rare earth element and at least an element of iron or cobalt, nickel, and manganese. A powder of an alloy including iron or cobalt is more preferable. Various magnetic powders such as rare earth element-iron-boron powders, rare earth element-iron-nitrogen powders, and rare earth element-cobalt powders are preferable as such a rare earth magnetic alloy. Among these, rare earth element-iron-nitrogen magnetic powders are preferable. One or more species of Sm, Nd, Pr, Y, La, Ce, Gd, Dy, and Tb may be preferably used as the above-mentioned rare earth element. If two or more species of them are used, they may be used as a mixture. Among these, Sm and Nd are preferable.

The above-mentioned magnetic powders essentially including a rare earth element and iron may contain another component other than the rare earth element and iron. The another component is not especially limited as the magnetic powders exhibit a magnetic property. Various magnetic powders such as ferrite and Alnico alloy which are generally used as a raw material for bond magnets are preferable, for example. As the above-mentioned various magnetic powders that are raw materials for bond magnets, anisotropic magnetic powders and isotropic magnetic powders can be preferably used. These magnetic powders are preferably used by being mixed with the above-mentioned magnetic powders essentially including a rare earth element and iron.

The above-mentioned another component, specifically, various magnetic powders as a raw material for bond magnets, has an anisotropic magnet field (HA) of 50 kOe or more.

It is preferable that the above-mentioned magnetic powders include 5 to 40 a. % (atom %) of Sm or Nd and 50 to 90 at. % of Fe or Co.

It is preferable that the above-mentioned magnetic powder has an average particle diameter of 5 µm or less. The preferred average particle diameter is particularly 3 µm or less. If the average particle diameter is more than 5 µm, the moldability is deteriorated, and therefore the powders might not be preferably used as a raw material for bond magnets.

With respect to the ratio between the thermosetting binder resin composition to the rare earth alloy in the above-mentioned thermosetting resin composition for bond magnets, it is preferable that 0.1 to 100 parts by weight of the thermosetting binder resin composition is contained relative to 100 parts by weight of the rare earth alloy. If the thermosetting binder resin composition is less than 0.1 parts by weight, the mechanical strength of a cured article of the resin composition might be insufficient. If it is more than 100 parts by weight, desired magnetic characteristics might not be obtained. More preferably, 1 to 50 parts by weight of the thermosetting binder resin composition is included and still more preferably, 3 to 30 part by weight of it is included.

The above-mentioned resin composition for bond magnets may contain another component such as a component for curing (curing agent) if necessary, as long as the resin composition for bond magnets includes the above-mentioned thermosetting binder resin composition and rare earth alloy powders. The above-mentioned curing agents may be preferably used as the above-mentioned curing agent. Specifically, a compound containing an epoxy group and/or a glycidyl group, a polyphenol compound, a maleimide compound, and the like are preferable as the thermosetting resin of the thermosetting binder resin composition. Agents for curing such compounds and the like may be used.

The above-mentioned another component may contain an additive other than the above-mentioned curing agents. Examples thereof include a stabilizer, a demolding agent, a coupling agent, a coloring agent, a plasticizer, a diluent such as a solvent and a reactive diluent, a flexibilization agent, various rubber substances, a photosensitive agent, a filler, a flame retarder, and a pigment.

In the above-mentioned thermosetting resin composition for bond magnets, a method of mixing the respective components contained in the composition is not especially limited. Mixing machines such as a ribbon blender, a tumbler, a nauta mixer, a Henschel mixer, a super mixer, and a planetary mixer, and kneading machines such as a Banbury mixer, a kneader, a roll, a kneader Ruder, a single screw extruder, and a twin screw extruder may be used.

It is preferable that the mixing machines used for mixing the above-mentioned thermosetting resin composition for bond magnets prevents curing of the thermosetting resin composition due to frictional exotherm at the time of mixing. Specifically, it is preferable that the mixing machine has a low shearing force and has a cooling function. The composition becomes in a massive form by mixing, and therefore it is preferable that the composition is molded by the following molding method to product a bond magnet.

It is preferable that the above-mentioned curable resin composition for magnet bonds is molded by an injection method, a compression molding method, an extrusion molding method, a rolling molding method, or a transfer molding method. Thus, a bond magnet excellent in an antirust property, a mechanical strength, a flexibility, a heat resistance, as well as magnetic characteristics and a shape flexibility can be easily produced.

Effect of the Invention

The resin composition of the present invention and its cured article have the above-mentioned configuration, and the present invention provides a silane compound useful for resin compositions excellent in heat resistance, pressure resistance, mechanical and chemical stability, and heat conductivity and capable of forming cured articles which hardly reduce physical properties even under severe environments such as high temperature and high pressure; its production method, and a resin composition containing the silane compound.

BEST MODES FOR CARRYING OUT THE INVENTION

Hereinafter, the invention will be described in detail with reference to Examples, however, the invention should not be limited to these Examples. Unless otherwise specified, "part(s)" means "part(s) by weight" and "%" means "% by weight".

The reference character n in the chemical formulas described below shows repeat of the siloxane bond in the brackets and the chemical formulas of the compounds obtained in the respective Synthesis Examples show main compositions of the synthesized compounds.

Synthesis Example 1

Synthesis of poly{(γ-phthalimido)propylsilsesquioxane)}

A 500 mL of four-necked flask equipped with a stirrer, a temperature sensor, and a total condenser was loaded with 86.6 g of diglyme previously dried by molecular sieve and 179.4 g of 3-aminopropyltrimethoxysilane and while being stirred, the mixture was heated to 100° C. in condition of circulating dried nitrogen to remove water in the system. Next, the reaction solution temperature was kept at 80° C., 148.2 g of phthalic anhydride was loaded in a tetrameric manner for 30 minutes. In 3 hours after completion of the loading, it was confirmed by high performance liquid chromatography that phthalic anhydride was completely consumed.

The reaction product was sampled and subjected to measurement by $^1$H-NMR, $^{13}$C-NMR, MALDI-TOF-MS to find that the product contained the compound defined by the following chemical formula (21).

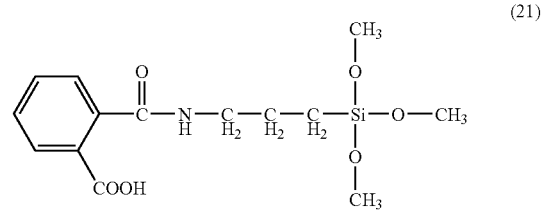

(21)

$^1$HNMR: 0.72 (t,2H), 1.81 (m,2H), 3.48 (dd, 2H), 3.72 (s, 9H), 4.71 (bs, 1H), 7.56-7.72 (m, 2H), 7.73-7.86 (m, 2H), 11.0 (bs, 1H)
$^{13}$C-NMR: 9.1, 22.2, 40.6, 50.5, 122.3, 122.4, 122.5, 132.4, 134.0, 134.2, 168.7, 172.0
MALDI-TOF-MS: 334 (M+Li)

Successively, 54.2 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 7.9 g of pyridine was loaded and as it was, the temperature was increased again and while condensation water was recovered, the temperature was increased to 160° C. for 3 hours and the reaction solution was kept at that temperature for 2 hours and cooled to room temperature.

The reaction product was a dark brown and highly viscous liquid containing 80.6% of a non-volatile component and when the molecular weight was measured by GPC, the number average molecular weight was 2310 and the weight average molecular weight was 2830. $^1$H-NMR and $^{13}$C-NMR measurement was carried out to find that the reaction product contained a compound defined by the following chemical formula (22).

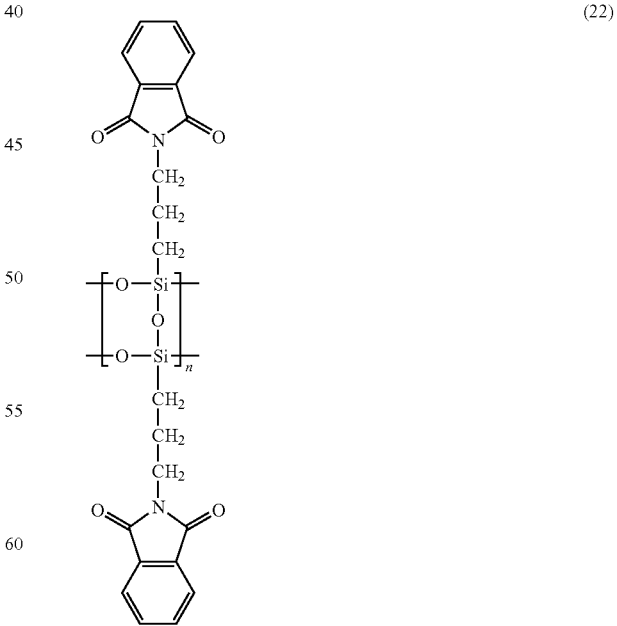

(22)

$^1$HNMR: 0.3-0.9 (bs, 2H), 1.5-1.8 (bs, 2H), 3.4-3.6 (bs, 2H), 7.1-7.7 (bs, 4H)
$^{13}$C-NMR: 10.0, 22.1, 40.4, 123.1, 132.3, 133.7, 168.1

Synthesis Example 2

Synthesis of poly{γ-(1,8-naphthalimido)propylsilsesquioxane}

A 300 mL of four-necked flask equipped with a stirrer, a temperature sensor, and a total condenser was loaded with 89.3 g of N,N'-dimethylacetamide previously dried by molecular sieve and 29.7 g of 3-aminopropyltrimethoxysilane and while being stirred, the mixture was heated to 100° C. in condition of circulating dried nitrogen to remove water in the system. Next, it was kept at 100° C. as it was, 32.8 g of 1,8-naphthalenedicarboxylic acid anhydride was loaded in a tetrameric manner for 30 minutes. In 9 hours after completion of the loading, it was confirmed by high performance liquid chromatography that 1,8-naphthalenedicarboxylic acid anhydride was completely consumed.

The reaction product was sampled and subjected to measurement by $^1$H-NMR, $^{13}$C-NMR, MALDI-TOF-MS to find that the product contained the compound defined by the following chemical formula (23).

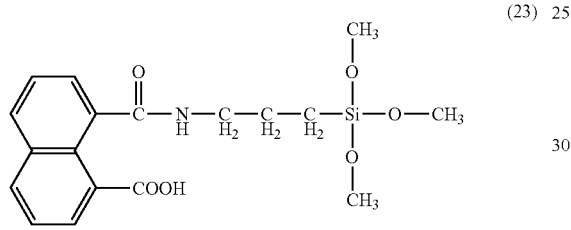

(23)

$^1$HNMR: 0.61 (t, 2H), 1.63 (m, 2H), 3.26 (dd, 2H), 3.45 (s, 9H), 3.90 (bs, 1H), 7.69 (t, 1H), 7.79 (t, 1H), 8.24-8.33 (m, 2H), 8.38 (d, 1H), 8.41 (d, 1H), 11.0 (bs, 1H)

$^{13}$C-NMR: 7.0, 21.7, 42.8, 49.2, 123.8, 127.5, 127.8, 127.9, 130.7, 130.9, 131.1, 131.9, 134.7, 135.0, 163.5, 170.3

MALDI-TOF-MS: 384 (M+Li)

Successively, 9.0 g of deionized water diluted with 6.2 g of N,N'-dimethylacetamide was collectively loaded and after the temperature was increased to reflux methanol byproduct by the total condenser and the reaction system was kept at 95° C. for 10 hours, the total condenser was replaced with a partial condenser and again the temperature was increased and while methanol byproduct and condensation water were recovered, the reaction solution temperature was increased to 120° C. for 3 hours. At the time when the temperature reached 120° C., 2.6 g of pyridine was loaded and as it was, the temperature was increased again and while condensation water was recovered, the temperature was increased to 160° C. for 3 hours and the reaction solution was kept at that temperature for 2 hours and cooled to room temperature.

The reaction product was a dark brown and highly viscous liquid containing 37.1% of a non-volatile component and when the molecular weight was measured by GPC, the number average molecular weight was 1450 and the weight average molecular weight was 1500. $^1$H-NMR and $^{13}$C-NMR measurement was carried out to find that the reaction product contained a compound defined by the following chemical formula (24).

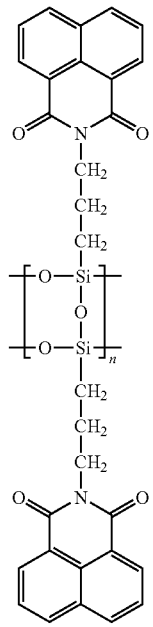

(24)

$^1$HNMR: 1.0-1.5 (bs, 2H), 2.2-2.6 (bs, 2H), 3.2-3.5 (bs, 2H), 7.2-7.6 (bs, 2H), 7.7-8.1 (bs, 2H), 8.2-8.6 (bs, 2H)

$^{13}$C-NMR: 9.7, 21.2, 41.7, 122.6, 125.8, 126.9, 129.3, 130.1, 132.4, 162.5

Synthesis Example 3

Synthesis of poly{γ-(5-norbornene-2,3-imido)propylsilsesquioxane}

A 300 mL of four-necked flask equipped with a stirrer, a temperature sensor, and a total condenser was loaded with 35.1 g of diglyme previously dried by molecular sieve and 30.8 g of 3-aminopropyltrimethoxysilane and while being stirred, the mixture was heated to 100° C. in condition of circulating dried nitrogen to remove water in the system. Next, it was kept at 100° C. as it was, 28.2 g of 5-norbornene-2,3-dicarboxylic acid anhydride was loaded in a tetrameric manner for 30 minutes. In 9 hours after completion of the loading, it was confirmed by high performance liquid chromatography that 5-norbornene-2,3-dicarboxylic acid anhydride was completely consumed.

The reaction product was sampled and subjected to measurement by $^1$H-NMR, $^{13}$C-NMR, MALDI-TOF-MS to find that the product contained the compound defined by the following chemical formula (25).

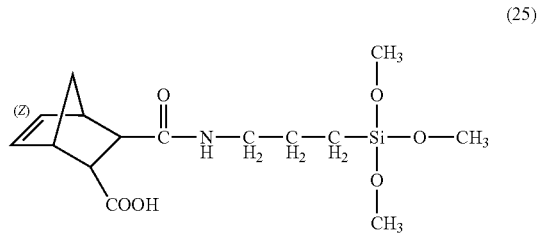

(25)

$^1$HNMR: 0.40 (t, 2H), 1.35 (m, 2H), 1.46 (dd, 2H), 3.08-3.17 (m, 1H), 3.20 (dd, 2H), 3.28-3.37 (m, 1H), 3.40 (s, 9H), 3.42 (m, 1H), 3.48 (m, 1H), 5.91 (s, 2H), 6.22 (bs, 1H), 11.0 (bs, 1H)

$^{13}$C-NMR: 8.1, 21.2, 40.6, 44.9, 45.8, 50.3, 50.6, 52.3, 134.5, 177.8, 178.1

MALDI-TOF-MS: 350 (M+Li)

Successively, 9.3 g of deionized water was collectively loaded and after the temperature was increased to reflux methanol byproduct by the total condenser and the reaction system was kept at 95° C. for 10 hours, the total condenser was replaced with a partial condenser and again the temperature was increased and while methanol byproduct and condensation water were recovered, the reaction solution temperature was increased to 120° C. for 3 hours. At the time when the temperature reached 120° C., 1.4 g of pyridine was loaded and as it was, the temperature was increased again and while condensation water was recovered, the temperature was increased to 160° C. for 3 hours and the reaction solution was kept at that temperature for 2 hours and cooled to room temperature.

The reaction product was a dark brown and highly viscous liquid containing 58.2% of a non-volatile component and when the molecular weight was measured by GPC, the number average molecular weight was 2340 and the weight average molecular weight was 2570. $^1$H-NMR and $^{13}$C-NMR measurement was carried out to find that the reaction product contained a compound defined by the following chemical formula (26).

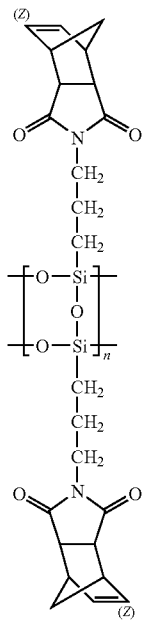

(26)

$^1$HNMR: 0.25-0.45 (bs, 2H), 1.2-1.45 (bs, 2H), 1.47 (dd, 2H), 3.0-3.2 (bs, 4H), 3.4-3.6 (bs, 2H), 5.8-6.0 (bs, 2H)

$^{13}$C-NMR: 9.7, 21.5, 40.4, 44.9, 45.7, 50.1, 134.2, 178.0

Synthesis Example 4

Synthesis of poly{γ-(hexahydro-4-methylphthalimido)propylsilsesquioxane}

A 300 mL of four-necked flask equipped with a stirrer, a temperature sensor, and a total condenser was loaded with 30.1 g of xylene previously dried by molecular sieve and 20.1 g of 3-aminopropyltrimethoxysilane and while being stirred, the mixture was heated to 100° C. in condition of circulating dried nitrogen to remove water in the system. Next, it was kept at 100° C. as it was, 18.8 g of hexahydro-4-methylphthalic anhydride was loaded in a tetrameric manner for 30 minutes. In 9 hours after completion of the loading, it was confirmed by high performance liquid chromatography that hexahydro-4-methylphthalic anhydride was completely consumed.

The reaction product was sampled and subjected to measurement by $^1$H-NMR, $^{13}$C-NMR, MALDI-TOF-MS to find that the product contained the compound defined by the following chemical formula (27).

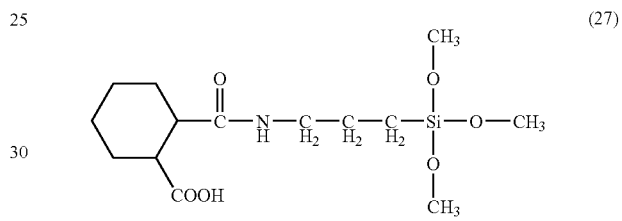

(27)

$^1$HNMR: 0.72 (t, 2H), 0.93 (d, 3H), 1.21 (m, 2H), 1.46 (m, 2H), 1.60 (m, 2H), 1.71 (m, 2H), 1.81 (m, 1H), 2.48 (m, 1H), 2.63 (m, 1H), 2.94 (s, 1H), 3.22 (m, 2H), 3.72 (s, 9H), 6.6 (s, 1H)

$^{13}$C-NMR: 6.8, 22.5, 22.9, 24.9, 27.6, 30.8, 35.0, 39.8, 40.9, 50.5, 179.6, 180.4

MALDI-TOF-MS: 350 (M+Li)

Successively, 6.1 g of deionized water was diluted with 36.0 g of diglyme and thereafter collectively loaded and after the temperature was increased to reflux methanol byproduct by the total condenser and the reaction system was kept at 95° C. for 10 hours, the total condenser was replaced with a partial condenser and again the temperature was increased and while methanol byproduct and azeotropic substance of condensation water and xylene were recovered, the reaction solution temperature was increased to 120° C. for 3 hours. At the time when the temperature reached 120° C., 1.4 g of pyridine was loaded and as it was, the temperature was increased again and while the azeotropic substance of the condensation water and xylene was recovered, the temperature was increased to 160° C. for 3 hours and the reaction solution was kept at that temperature for 2 hours and cooled to room temperature.

The reaction product was a dark brown and highly viscous liquid containing 47.3% of a non-volatile component and when the molecular weight was measured by GPC, the number average molecular weight was 4080 and the weight average molecular weight was 4230. $^1$H-NMR and $^{13}$C-NMR measurement was carried out to find that the reaction product contained a compound defined by the following chemical formula (28).

(28)

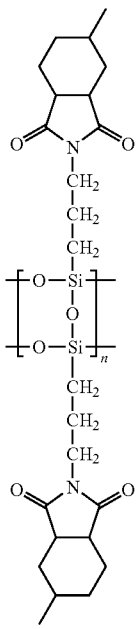

¹HNMR: 0.45-0.70 (bs, 2H), 0.88 (d, 3H), 1.25-1.4 (bs, 2H), 1.45-1.6 (bs, 2H), 1.73 (bd, 2H), 1.9-2.1 (bs, 1H), 2.15-2.25 (bs, 1H), 2.7-3.05 (bs, 2H), 3.3-3.5 (bs, 2H)

¹³C-NMR: 10.2, 21.3, 21.8, 22.4, 23.9, 29.3, 31.0, 35.4, 39.4, 40.6, 179.1

Synthesis Example 5

Synthesis (2) of poly(γ-phthalimidopropylsilsesquioxane)

A 300 mL of four-necked flask equipped with a stirrer, a temperature sensor, and a total condenser was loaded with 37 g of diglyme previously dried by molecular sieve, 62.1 g of 3-(triethoxysilyl)propyl isocyanate, and 37.2 g of phthalic anhydride and while being stirred, the mixture was heated to start refluxing in condition of circulating dried nitrogen and decarbonation reaction was carried out by keeping temperature for 8 hours after stabilization and it was confirmed by high performance liquid chromatography that phthalic anhydride was completely consumed.

The reaction product was sampled and subjected to measurement by ¹H-NMR, ¹³C-NMR, MALDI-TOF-MS to find that the product contained a compound defined by the chemical formula (21) in Synthesis Example 1 in which all of methoxy groups at terminals were replaced with ethoxy groups.

Successively, 13.6 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 8.5 g of pyridine was loaded and as it was, the temperature was increased again and while condensation water was recovered, the temperature was increased to 160° C. for 3 hours and the reaction solution was kept at that temperature for 2 hours and cooled to room temperature.

The reaction product was a dark brown and highly viscous liquid containing 75.6% of a non-volatile component and when the molecular weight was measured by GPC, the number average molecular weight was 2280 and the weight average molecular weight was 2920. ¹H-NMR and ¹³C-NMR measurement was carried out to find that the reaction product contained a compound defined by a composition formula same as the chemical formula (22) in Synthesis Example 1.

Synthesis Example 6

Synthesis (3) of poly(γ-phthalimidopropylsilsesquioxane)

A 300 mL of four-necked flask equipped with a stirrer, a temperature sensor, and a total condenser was loaded with 20.2 g of N,N'-dimethylacetamide previously dried by molecular sieve, 20.2 g of similarly dried diglyme, 54.5 g of 3-chloropropyltrimethoxysilane, and 40.3 g of phthalimide and while the mixture was stirred at 60° C. in condition of circulating dried nitrogen, 26.1 g of pyridine was dropwise added for 4 hours. After completion of the dropwise addition, stirring was continued at 80° C. for 8 hours and it was confirmed by high performance liquid chromatography that phthalimide was completely consumed.

The reaction product was sampled and subjected to measurement by ¹H-NMR, ¹³C-NMR, MALDI-TOF-MS to find that the product contained a compound defined by the chemical formula (21) in Synthesis Example 1.

Successively, 14.8 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 9.2 g of pyridine was loaded and as it was, the temperature was increased again and while condensation water was recovered, the temperature was increased to 160° C. for 3 hours and the reaction solution was kept at that temperature for 2 hours and cooled to 60° C.

The reaction product was a dark brown and highly viscous liquid containing 76.3% of a non-volatile component and when the molecular weight was measured by GPC, the number average molecular weight was 2330 and the weight average molecular weight was 3050. ¹H-NMR and ¹³C-NMR measurement was carried out to find that the reaction product contained a compound defined by a composition formula same as the chemical formula (22) in Synthesis Example 1.

Synthesis Example 7

Trial of synthesis from poly(3-aminopropyl)silsesquioxane

A 500 mL of four-necked flask equipped with a stirrer, a temperature sensor, and a total condenser was loaded with 357.3 g of 1N hydrochloric acid and in stirring condition at room temperature, 42.7 g of 3-aminopropyltrimethoxysilane was added and the mixture was kept for 3 hours and then kept for 4 hours after heated to 60° C. The obtained reaction solution was transferred to a square tray made of PTFE and left overnight at 80° C. in an oven to remove volatile component and further left at 120° C. and reduced pressure of 5 kPa for 2 hours in the oven to obtain poly(3-aminopropyl)silsesquioxane. The yield was 34.9 g.

Since the reaction product, poly(γ-aminopropyl)silsesquioxane was dissolved only in water, an aqueous 10% solution was produced and phthalic anhydride was added, however, no desired reaction product was obtained and instead a large quantity of phthalic acid was produced.

When the silane compounds obtained finally in the respective Synthesis Examples 1 to 7 were determined, no alkoxy group was detected by $H^1$-NMR spectra and silanol groups were confirmed by near infrared spectra. Accordingly, it was confirmed that those silane compounds had silanol groups at molecular terminals.

Synthesis Example 8

Synthesis of poly[(cis-4-cyclohexene-1,2-imido)propylsilsesquioxane}

A 500 mL of four-necked flask equipped with a stirrer, a temperature sensor, and a total condenser was loaded with 103.7 g of diglyme previously dried by molecular sieve and 177.6 g of 3-aminopropyltrimethoxysilane and while being stirred, the mixture was heated to 100° C. in condition of circulating dried nitrogen to remove water in the system. Next, the reaction solution temperature was kept at 80° C., 150.7 g of cis-4-cyclohexene-1,2-dicarboxylic acid anhydride was loaded in a tetrameric manner for 30 minutes. In 3 hours after completion of the loading, it was confirmed by high performance liquid chromatography that cis-4-cyclohexene-1,2-dicarboxylic acid anhydride was completely consumed.

The reaction product was sampled and subjected to measurement by $^1$H-NMR, $^{13}$C-NMR, MALDI-TOF-MS to find that the product contained the compound defined by the following chemical formula (29).

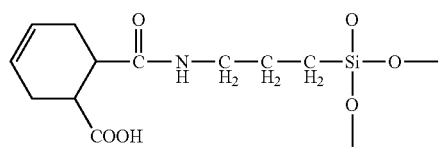

(29)

$^1$HNMR: 0.72 (t, 2H), 1.81 (m, 2H), 2.23 (dd, 4H), 2.74 (m, 1H), 2.91 (dd, 1H), 3.48 (dd, 2H), 3.72 (s, 9H), 5.74 (m, 2H), 11.0 (bs, 1H)

$^{13}$C-NMR: 9.1, 22.2, 25.5, 26.8, 40.6, 42.3, 43.1, 44.7, 131.7, 168.8, 172.7

MALDI-TOF-MS: 338 (M+Li)

Successively, 53.4 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 7.9 g of pyridine was loaded and as it was, the temperature was increased again and while condensation water was recovered, the temperature was increased to 160° C. for 3 hours and the reaction solution was kept at that temperature for 2 hours and cooled to room temperature.

The reaction product was a dark brown and highly viscous liquid containing 74.3% of a non-volatile component and when the molecular weight was measured by GPC, the number average molecular weight was 2041 and the weight average molecular weight was 2838. $^1$H-NMR and $^{13}$C-NMR measurement was carried out to find that the reaction product contained a compound defined by the following chemical formula (30).

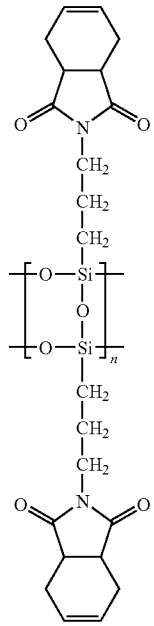

(30)

$^1$HNMR: 0.25-0.55 (bs, 2H), 1.3-1.5 (bs, 2H), 2.0-2.5 (dd, 4H), 2.9-3.1 (bs, 2H), 3.2-3.35 (bs, 2H), 5.65-5.8 (bs, 2H)

$^{13}$C-NMR: 10.0, 21.0, 23.8, 39.0, 41.1, 127.8, 180.5

The final products obtained in Synthesis Examples 1 to 4 and Synthesis Example 8 were put in aluminum trays and left in a reduced oven at 160° C. and 5 kPa to completely evaporate volatile components and isolate 5 kind silane compounds. The silane compounds in Synthesis Examples 1 to 4 and 8 correspond to the silane compounds A, B, C, D, and E, respectively.

silane compound A: poly(γ-phthalimidopropylsilsesquioxane)

silane compound B: poly{γ-(1,8-naphthalimido)propylsilsesquioxane} silane compound C: poly{γ-(5-norbornene-2,3-imido)propylsilsesquioxane} silane compound D: poly{γ-(hexahydro-4-methylphthalimido)propylsilsesquioxane} silane compound E: poly{(cis-4-cyclohexene-2,3-imido)propylsilsesquioxane}

Cage-Like Silsesquioxane

Synthesis Example 9

Synthesis of octa(γ-phthalimidopropyl)silsesquioxane

According to the synthesis technique described in Reference Document 1 (F. J. Feher and K. D. Wyndham, Chem. Comm., 1998, 323-324), octa(γ-phthaloimidopropyl)silsesquioxane was synthesized and subjected to the following reaction. A 300 mL of four-necked flask equipped with a stirrer, a temperature sensor, and a total condenser was loaded with 160.6 g of diglyme previously dried by molecular sieve, 16.34 g of octa(3-chloroammoniumopropyl)silsesquioxane, and 16.67 g of phthalic anhydride and while being stirred, the mixture was heated to 60° C. in condition of circulating dried nitrogen to remove water in the system and 6.37 g of diazabicycloundecene was loaded in a tetrameric manner for 30 minutes. After completion of the loading, the reaction solution was kept at 60° C. for 4 hours and it was confirmed by high performance liquid chromatography that phthalic anhydride was completely consumed. After being cooled to room temperature, the reaction solution was filtered to separate light yellow solid matter. The filtrate was sampled and subjected to measurement by $^1$H-NMR, $^{13}$C-NMR, MALDI-TOF-MS to find that the product contained the compound defined by the following chemical formula (31).

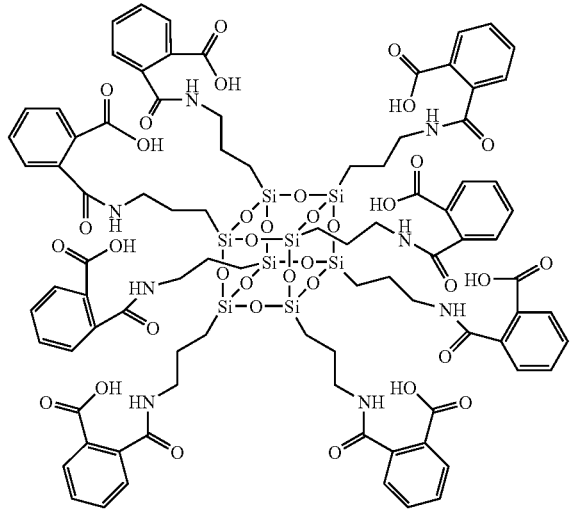

(31)

$^1$HNMR: 0.72 (t, 2H), 1.81 (m, 2H), 3.48 (dd, 2H), 4.71 (bs, 1H), 7.56-7.72 (m, 2H), 7.73-7.86 (m, 2H), 11.0 (bs, 1H)

$^{13}$C-NMR: 9.1, 22.2, 40.6, 122.3, 122.4, 122.5, 132.4, 134.0, 134.2, 168.7, 172.0

MALDI-TOF-MS: 2073 (M+Li)

Further, the filtrate was turned back again to the reaction apparatus and the total condenser was replaced with a partial condenser and thereafter, again the temperature was increased and while condensation water was recovered, the reaction solution temperature was increased to 120° C. for 3 hours. At the time when the temperature reached 120° C., 0.9 g of pyridine was loaded and while condensation water was recovered, the temperature was increased to 160° C. for 3 hours and the reaction solution was kept at that temperature for 2 hours and cooled to room temperature.

The reaction product was a dark brown solution containing 25.3% of a non-volatile component and when the molecular weight was measured by GPC; very sharp peaks were observed that the number average molecular weight was 1915 and the weight average molecular weight was 1923. $^1$H-NMR and $^{13}$C-NMR measurement was carried out to find that the reaction product contained a compound defined by the following chemical formula (32).

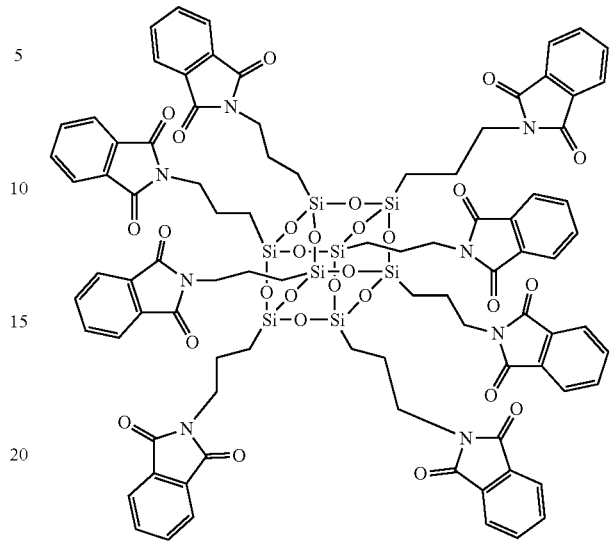

(32)

$^1$HNMR: 0.41 (t, 2H), 1.34 (m, 2H), 3.27 (t, 2H), 7.66 (dd, 2H), 8.13 (5, 2H)

$^{13}$C-NMR: 9.2, 21.0, 40.7, 123.1, 132.3, 133.7, 168.1

MALDI-TOF-MS: 1929 (M+Li)

Synthesis Example 10

Synthesis of octa{γ-(5-norbornene-2,3-imidopropyl) silsesquioxane

According to the synthesis technique described in Reference Document 1 (F. J. Feher and K. D. Wyndham, Chem. Comm., 1998, 323-324), octa(γ-chloroammoniumpropyl) silsesquioxane was synthesized and subjected to the following reaction. A 300 mL of four-necked flask equipped with a stirrer, a temperature sensor, and a total condenser was loaded with 157.9 g of diglyme previously dried by molecular sieve, 15.05 g of octa(3-chloroammoniumopropyl)silsesquioxane, and 17.02 g of 5-norbornene-2,3-dicarboxylic acid anhydride and while being stirred, the mixture was heated to 60° C. in condition of circulating dried nitrogen to remove water in the system and 10.06 g of sodium tert-butoxide was loaded in a tetrameric manner for 30 minutes. After completion of the loading, the reaction solution was kept at 60° C. for 4 hours and it was confirmed by high performance liquid chromatography that 5-norbornene-2,3-dicarboxylic acid anhydride was completely consumed. After being cooled to room temperature, the reaction solution was filtered to separate light yellow solid matter. The filtrate was sampled and subjected to measurement by $^1$H-NMR, $^{13}$C-NMR, MALDI-TOF-MS to find that the product contained the compound defined by the following chemical formula (33).

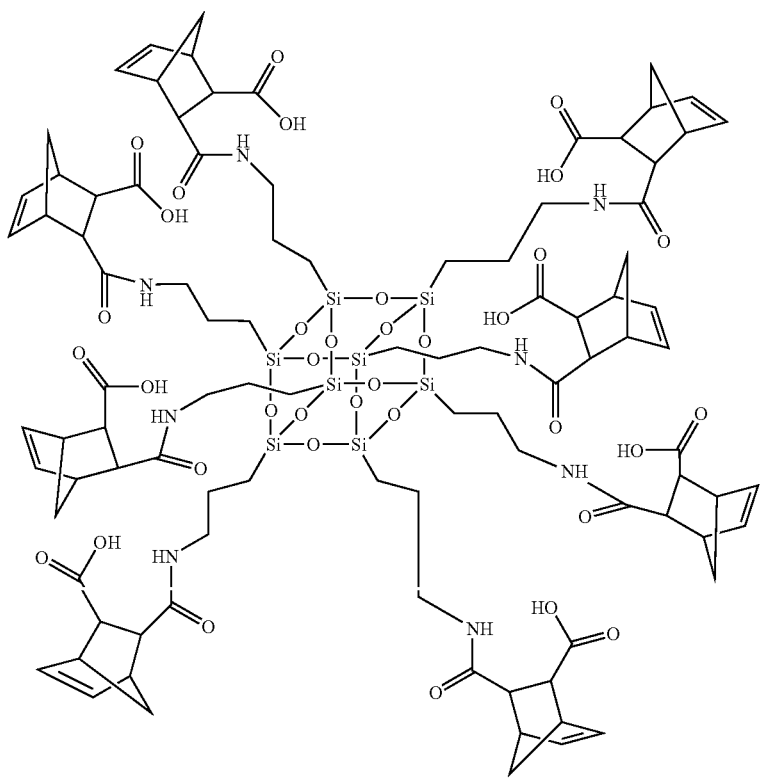

(33)

$^1$HNMR: 0.40 (t, 2H), 1.35 (m, 2H), 1.46 (dd, 2H), 3.08-3.17 (m, 1H), 3.20 (dd, 2H), 3.28-3.37 (m, 1H), 3.42 (m, 1H), 3.48 (m, 1H), 5.91 (s, 2H), 6.22 (bs, 1H), 11.0 (bs, 1H)

$^{13}$C-NMR: 8.1, 21.2, 40.6, 44.9, 45.8, 50.6, 52.3, 134.5, 177.8, 178.1

MALDI-TOF-MS: 2202 (M+Li)

Further, the filtrate was turned back again to the reaction apparatus and the total condenser was replaced with a partial condenser and thereafter, again the temperature was increased and while condensation water was recovered, the reaction solution temperature was increased to 120° C. for 3 hours. At the time when the temperature reached 120° C., 0.9 g of pyridine was loaded and while condensation water was recovered, the temperature was increased to 160° C. for 3 hours and the reaction solution was kept at that temperature for 2 hours and cooled to room temperature.

The reaction product was a dark brown liquid containing 25.1% of a non-volatile component and when the molecular weight was measured by GPC, very sharp peaks were observed that the number average molecular weight was 2020 and the weight average molecular weight was 2035. $^1$H-NMR, $^{13}$C-NMR, and MALDI-TOF-MS measurement was carried out to find that the reaction product contained a compound defined by the following chemical formula 34).

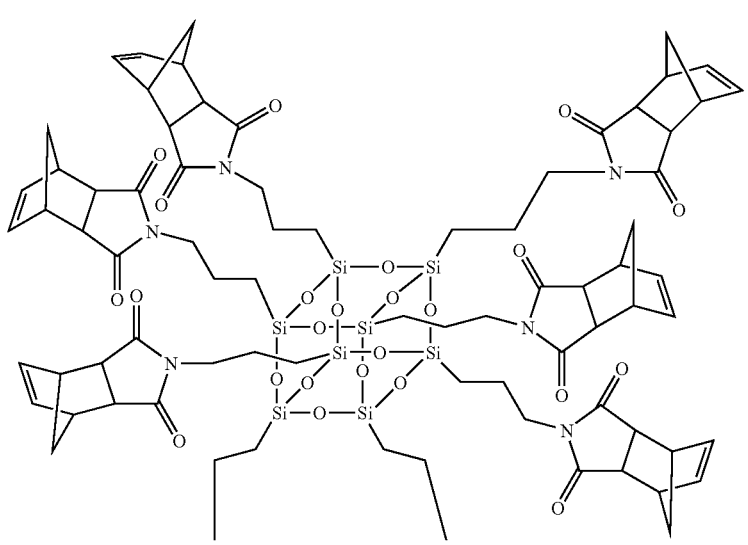

(34)

-continued

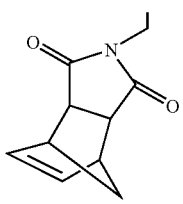 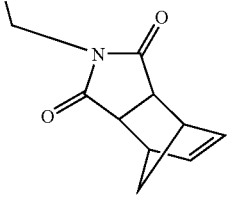

¹HNMR: 0.41 (t, 2H), 1.34 (m, 2H), 1.53 (dd, 2H), 3.17 (m, 4H), 3.27 (t, 2H), 5.98 (s, 2H)
¹³C-NMR: 9.2, 21.1, 40.7, 45.0, 46.0, 52.3, 134.6, 177.8
MALDI-TOF-MS: 2058 (M+Li)

The final product liquids obtained in Synthesis Examples 9 and 10 were put in aluminum trays and left in a reduced oven at 160° C. and 5 kPa to completely evaporate volatile components and isolate 4 kind silane compounds. The silane compounds in Synthesis Example 9 are the silane compounds F and H. The silane compounds in Synthesis Example 10 are the silane compounds G and I.

silane compound F: poly(γ-phthalimidopropyl)silsesquioxane
silane compound G: poly{γ-(5-norbornene-2,3-imido)propyl}silsesquioxane
silane compound H: octa{γ-(phthalimidopropyl)silsesquioxane}
silane compound I: octa{γ-(5-norbornene-2,3-imido)propyl}silsesquioxane}

Synthesis Example 11

A 500 mL of four-necked flask equipped with a stirrer, a temperature sensor, and a total condenser was loaded with 67 g (60 mmol) of 1-dimethylsiloxy-3,5,7,9,11,13,15-heptakis(trimethylsiloxy) pentacyclo[9.5.1.1$^{3.9}$.1$^{5.15}$.1$^{7.13}$]octasiloxane dissolved into 600 g of toluene. Thereinto, 40 mg of a toluene solution of platinum (0) divinyltetramethyldisiloxane complex (3% by weight of platinum) was added. Under stirring at a room temperature, 13.7 g (68 mmol) of N,N-bis(trimethylsilyl)allylamine was added. The reaction had completed after the stirring was kept for 24 hours at a room temperature. The reaction mixture was condensed under reduced pressure. The obtained crude product was washed three times with 6 mL of acetonitrile and dried in a vacuum. As a result, 68.6 g of a white solid was obtained. When the obtained white solid was measured by GPC, the number average molecular weight was 1348 and the weight average molecular weight was 1350. ¹H-NMR, ¹³C-NMR, and ²⁹Si-NMR, MALDI-TOF-MS, and GPC were carried out to find that the obtained white solid contained a compound defined by the following formula (35):

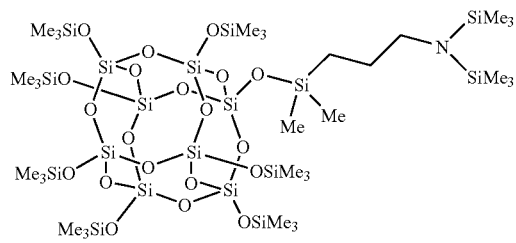

(35)

The yield was 86.8%. The analysis results are shown below.
¹HNMR: 0.08 (18H, s), 0.13 (6H, s), 0.15 (63H, s), 0.50-0.44 (2H, m), 1.39-1.28 (2H, m), 2.85-1.67 (2H, m)

¹³C-NMR: −0.5, 1.2, 1.3, 2.1, 14.9, 28.6, 49.0
²⁹Si-NMR: −109.0, 5.1, 12.5
MALDI-TOF-MS: 1338 (M+Na+)

Successively, a 500 mL of four-necked flask equipped with a stirrer, a temperature sensor, and a total condenser was loaded with 27 g of the compound defined by the above formula (35), 3.3 g of phthalic anhydride, and 100 g of diglyme. The mixture was stirred for 8 hours in condition of circulating nitrogen to remove a volatile component by a rotating evaporator. As a result, 29.3 g of a light yellow solid was obtained. When the obtained light yellow solid was measured by GPC, the number average molecular weight was 1340 and the weight average molecular weight was 1345. The obtained light yellow solid was also measured for a mass analysis by MALDI-TOF-MS. The following results were obtained.

MALDI-TOF-MS: 1338(M+Na+)

This result showed that the obtained compound was a compound represented by the following formula (36):

(36)

Me₃SiO, OSiMe₃
Me₃SiO
Me₃SiO OSiMe₃
Me₃SiO OSiMe₃

Synthesis Example 12

A light yellow powder was obtained using octa(dimethylhydroxy)silsesquioxane (trade name: OctaSilane POSS SH1310, product of Hybrid Plastics) instead of 1-dimethylsiloxy-3,5,7,9,11,13,15-heptakis(trimethylsiloxy)pentacyclo[9.5.1.1$^{3.9}$.1$^{5.15}$.1$^{7.13}$]octasiloxane. When the obtained light yellow solid was measured by GPC, the number average molecular weight was 2476 and the weight average molecular weight was 2488. The obtained light yellow solid was also measured for a mass analysis by MALDI-TOF-MS. The following results were obtained.

MALDI-TOF-MS: (M+Na+)

This result showed that the obtained compound is a compound represented by the following formula (37):

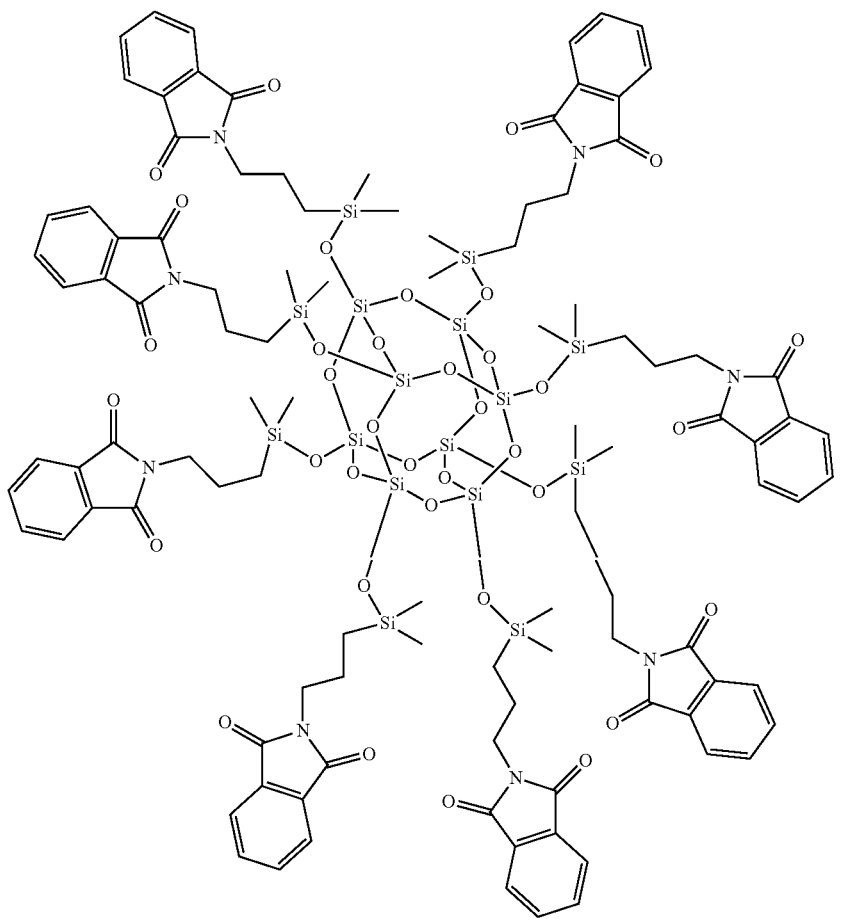

(37)

The final products obtained in Synthesis Examples 11 to 12 were put in aluminum trays and left in a reduced oven at 160° C. and 5 kPa to completely evaporate volatile components and isolate 2 kind silane compounds. The silane compound J was produced in Synthesis Example 11 and defined by the above formula (36). The silane compound K was produced in Synthesis Example 12 and defined by the above formula (37).

Adhesive Composition

Synthesis Example 13

Synthesis of poly{γ-(octenylsuccinimido)propylsilsesquioxane}

A 300 mL of four-necked flask equipped with a stirrer, a temperature sensor, and a total condenser was loaded with 36.9 g of diglyme previously dried by molecular sieve, 36.9 g of xylene, and 50.74 g of 3-aminopropyltrimethoxysilane and while being stirred, the mixture was heated to 100° C. in condition of circulating dried nitrogen to remove water in the system. Next, while the reaction solution temperature was kept at 80° C., 60.10 g of octenylsuccinic acid anhydride (isomer mixture) was loaded in a tetrameric manner for 30 minutes. In 3 hours after completion of the loading, it was confirmed by high performance liquid chromatography that octenylsuccinic acid anhydride was completely consumed.

When the reaction product was sampled and subjected to measurement by $^1$H-NMR, detailed spectrum determination was difficult due to bulky aliphatic skeleton, however, it was found that there are a singlet peak with large integrated value attributed to methoxysilyl group at δ=3.48 ppm; broad singlet peaks attributed to NH group and COOH group, respectively, at δ=4.71 ppm and 11.0 ppm; and a diastereotropic quartet peak attributed to ethylene bond at δ=5.72 ppm. Further, when $^{13}$C-NMR measurement was carried out, it was found that there are a peak attributed to methoxysilyl group at δ=50.5 ppm; peaks attributed to isomers derived from ethylene bond at δ=126.3 ppm, 130.6 ppm, 134.7 ppm, and 138 ppm; and peaks attributed to carbonyl carbon at δ=177.0 ppm and 179.9 ppm. Further, MALDI-TOF-MS was measured, the mass value of main peak was M=397 (M+Li) and accordingly, it was determined that the product contained a compound defined by the following chemical formula (38).

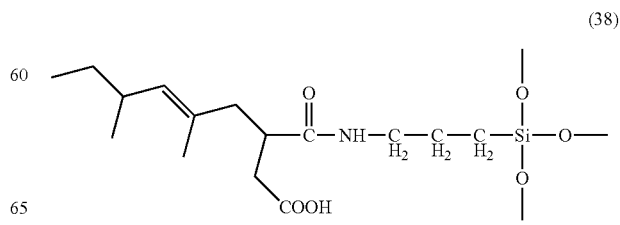

(38)

Successively, 15.3 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 2.3 g of pyridine was loaded and as it was, the temperature was increased again and while condensation water and toluene were recovered, the temperature was increased to 160° C. for 3 hours and the reaction solution was kept at that temperature for 2 hours and cooled to room temperature.

The reaction product was a dark brown and highly viscous liquid containing 70.6% of a non-volatile component and when the molecular weight was measured by GPC, the number average molecular weight was 2420 and the weight average molecular weight was 3140. When $^1$H-NMR measurement was carried out and the spectrum was compared with that of the above-mentioned chemical formula (35), it was found that the peaks at δ=3.48 ppm, 4.71 ppm, and 11.0 ppm disappeared. When $^{13}$C-NMR measurement was carried out, it was found that the peaks at δ=172.7 ppm and 176.3 ppm appeared in place of peaks at δ=177.0 ppm and 179.9 ppm. Accordingly, it was determined that the reaction product contained a compound defined by the following chemical formula (39).

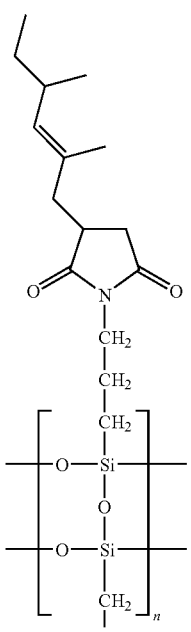

(39)

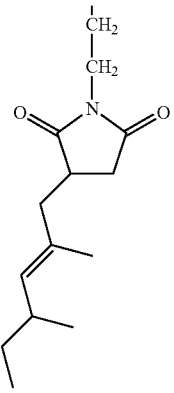

Synthesis Example 14

Synthesis of poly{γ-(dodecenylsuccinimido)propyl-silsesquioxane}

A 300 mL of four-necked flask equipped with a stirrer, a temperature sensor, and a total condenser was loaded with 42.0 g of diglyme previously dried by molecular sieve, 42.0 g of xylene, and 48.58 g of 3-aminopropyltrimethoxysilane and while being stirred, the mixture was heated to 100° C. in condition of circulating dried nitrogen to remove water in the system. Next, while the reaction solution temperature was kept at 80° C., 72.89 g of dodecenylsuccinic acid anhydride (isomer mixture) was loaded in a tetrameric manner for 30 minutes. In 3 hours after completion of the loading, it was confirmed by high performance liquid chromatography that dodecenylsuccinic acid anhydride was completely consumed.

When the reaction product was sampled and subjected to measurement by $^1$H-NMR, detailed spectrum determination was difficult due to bulky aliphatic skeleton, however, it was found that there are a singlet peak with large integrated value attributed to methoxysilyl group at δ=3.48 ppm; broad singlet peaks attributed to NH group and COOH group, respectively, at δ=4.71 ppm and 11.0 ppm; and a diastereotropic quartet peak attributed to ethylene bond at δ=5.72 ppm. Further, when $^{13}$C-NMR measurement was carried out, it was found that there are a peak attributed to methoxysilyl group at δ=50.5 ppm; peaks attributed to isomers derived from ethylene bond at δ=126.3 ppm, 130.6 ppm, 134.7 ppm, and 138 ppm; and peaks attributed to carbonyl carbon at δ=177.0 ppm and 179.9 ppm. Further, MALDI-TOF-MS was measured, the mass value of main peak was M=453 (M+Li) and accordingly, it was determined that the product contained a compound defined by the following chemical formula (40).

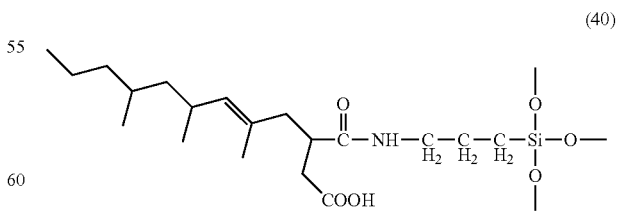

(40)

Successively, 14.7 g of deionized water was collectively loaded and after the temperature was increased to reflux methanol byproduct by the total condenser and the reaction system was kept for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 2.3 g of pyridine was loaded and as it was, the temperature was increased again and while condensation water and toluene were recovered, the temperature was increased to 160° C. for 3 hours and the reaction solution was kept at that temperature for 2 hours and cooled to room temperature.

The reaction product was a dark brown and highly viscous liquid containing 69.8% of a non-volatile component and when the molecular weight was measured by GPC, the number average molecular weight was 2890 and the weight average molecular weight was 3730. When $^1$H-NMR measurement was carried out and the spectrum was compared with that of the above-mentioned chemical formula (37), it was found that the peaks at δ=3.48 ppm, 4.71 ppm, and 11.0 ppm disappeared. When $^{13}$C-NMR measurement was carried out, it was found that the peaks at δ=172.7 ppm and 176.3 ppm appeared in place of peaks at δ=177.0 ppm and 179.9 ppm. Accordingly, it was determined that the reaction product contained a compound defined by the following chemical formula (41).

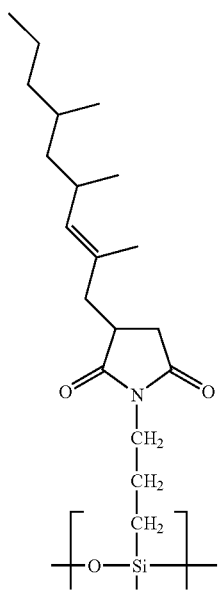

(41)

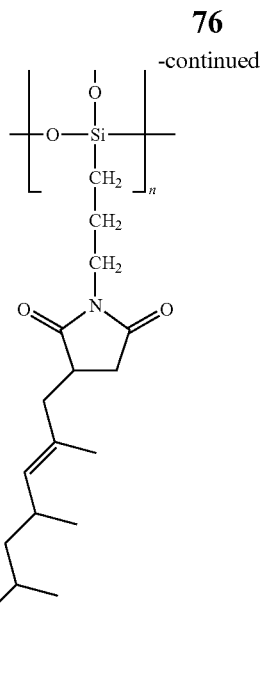

-continued

The final products obtained in Synthesis Examples 13 and 14 were put in aluminum trays and left in a reduced oven at 160° C. and 5 kPa to completely evaporate volatile components and isolate 2 kind silane compounds. The silane compound L was produced in Synthesis Example 13. The silane compound M was produced in Synthesis Example 14.

silane compound L: poly{γ-(octenylsuccinimide)propyl}silsesquioxane silane compound M: poly{γ-(dodecenylsuccinimide)propyl}silsesquioxane Examples 1 to 9 and Comparative Example 1

<Evaluation of Heat Resistance of Silane Compounds>

The above-mentioned silane compounds A to E and J to M were subjected to TGA analysis. For comparison, polyphenylsilsesquioxane (trade name: PPSQ-H, manufactured by Konishi Kagaku Kogyo) was used.

TGA analysis conditions were as follows.

Employed apparatus: TGA 50H (manufactured by Shimadzu Corporation)

Measurement conditions: temperature range 30° C. to 550° C., heating speed 10° C./min, circulated gas: dried air 50 mL/min., sampled weight 10 to 15 mg.

The resistance to hydrolysis was performed by immersing the above-mentioned silane compound into a 30% aqueous solution of sodium hydroxide at 25° C. for one week. The silane compound was evaluated as good if the appearance was not changed after the immersion. If the change was observed or the compound was completely decomposed and dissolved into the solution, the silane compound was evaluated as bad.

TABLE 1

|  | Example 1 | Example 2 | Example 3 | Example 4 | Example 5 | Example 6 | Example 7 | Example 8 | Example 9 | Comparative Example 1 |
|---|---|---|---|---|---|---|---|---|---|---|
| Silane compound | A | B | C | D | E | J | K | L | M | PPSQ-H |
| TGA 5% weight loss temperature | 463° C. | 473° C. | 441° C. | 430° C. | 465° C. | 394° C. | 380° C. | 350° C. | 338° C. | 383° C. |
| Resistance to hydrolysis | Good | Good | Good | Good | Good | Bad | Bad | Bad | Good | Good |

As shown in Table 1, the 5% weight loss temperature of the silane compounds within the scope of the invention under air circulation was all 400° C. or higher, whereas it did not reach 400° C. for polyphenylsilsesquioxane of Comparative Example. Among the silane compounds in the present application, in the silane compounds including an olefin chain-containing imide group such as the compounds L and M, the thermal decomposition temperature was reduced. Such a result shows that any of an aromatic ring, heterocyclic, and alicyclic skeletons, as in the silane compounds A to E, are preferable as the imide skeleton. Further, among the silane compounds in the present application, the silane compounds A to E having only $RSiO_3$ structure as the main skeleton are better than the silane compounds J and K which has the siloxane main skeleton containing a plurality of silicon clusters such as $SiO_4$ and $R_3SiO$ in view of an improvement in the heat resistance and the resistance to hydrolysis.

Evaluation of Characteristics Depending on Ratio of Organic Group Having Imide Skeleton Connected to Si Atom Synthesis Example 15

A 200 mL of four-necked flask equipped with a stirrer, a temperature sensor, and a total condenser was loaded with 44.0 g of diglyme previously dried by molecular sieve, 41.5 g of 3-aminopropyltrimethoxysilane and while being stirred, the mixture was heated to 100° C. in condition of circulating dried nitrogen to remove water in the system. Then, while the reaction solution was maintained at 80° C., 38.0 g of 5-norbornene-2,3-dicarboxylic anhydride was loaded in a tetrameric manner for 30 minutes. In 3 hours after completion of the loading, it was confirmed by high performance liquid chromatography that the 5-norbornene-2,3-dicarboxylic anhydride was completely consumed.

Successively, 17.9 g of deionized water was collectively loaded and after the temperature was increased to reflux methanol byproduct by the total condenser and the reaction system was kept under reflux for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 1.3 g of pyridine was loaded and as it was, the temperature was increased again and while condensation water was recovered, the temperature was increased to 160° C. for 3 hours and the reaction solution was kept at that temperature for 2 hours and cooled to room temperature. As a result, a silane compound N was obtained.

The silane compound N was a dark brown and highly viscous liquid containing 62.1% of a non-volatile component and when the molecular weight was measured by GPC, the number average molecular weight was 2530 and the weight average molecular weight was 3010. When $^1$H-NMR measurement was carried out, it was found that the ratio of the organic group including an imide skeleton was 69.7% relative to the organic groups connected to the Si atom. The ratio was almost equivalent to the ratio of the charged organic group including an imide skeleton.

Synthesis Example 16

A 200 mL of four-necked flask equipped with a stirrer, a temperature sensor, and a total condenser was loaded with 46.1 g of diglyme previously dried by molecular sieve, 29.4 g of 3-aminopropyltrimethoxysilane, and 32.5 g of phenyltrimethoxysilane and while being stirred, the mixture was heated to 100° C. in condition of circulating dried nitrogen to remove water in the system. Then, while the reaction solution was maintained at 80° C., 26.9 g of 5-norbornene-2,3-dicarboxylic anhydride was loaded in a tetrameric manner for 30 minutes. In 3 hours after completion of the loading, it was confirmed by high performance liquid chromatography that the 5-norbornene-2,3-dicarboxylic anhydride was completely consumed.

Successively, 17.7 g of deionized water was collectively loaded and after the temperature was increased to reflux methanol byproduct by the total condenser and the reaction system was kept under reflux for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 1.3 g of pyridine was loaded and as it was, the temperature was increased again and while condensation water was recovered, the temperature was increased to 160° C. for 3 hours and the reaction solution was kept at that temperature for 2 hours and cooled to room temperature. As a result, a silane compound P was obtained.

The silane compound P was a dark brown and highly viscous liquid containing 60.3% of a non-volatile component and when the molecular weight was measured by GPC, the number average molecular weight was 3300 and the weight average molecular weight was 3850. When $^1$H-NMR measurement was carried out, it was found that the ratio of the organic group including an imide skeleton was 50.3% relative to the organic groups connected to the Si atom. The ratio was almost equivalent to the ratio of the charged organic group including an imide skeleton.

Synthesis Example 17

A 200 mL of four-necked flask equipped with a stirrer, a temperature sensor, and a total condenser was loaded with 47.0 g of diglyme previously dried by molecular sieve, 22.6 g of 3-aminopropyltrimethoxysilane, and 58.3 g of phenyltrimethoxysilane and while being stirred, the mixture was heated to 100° C. in condition of circulating dried nitrogen to remove water in the system. Then, while the reaction solution was maintained at 80° C., 20.9 g of 5-norbornene-2,3-dicarboxylic anhydride was loaded in a tetrameric manner for 30 minutes. In 3 hours after completion of the loading, it was confirmed by high performance liquid chromatography that the 5-norbornene-2,3-dicarboxylic anhydride was completely consumed.

Successively, 22.7 g of deionized water was collectively loaded and after the temperature was increased to reflux methanol byproduct by the total condenser and the reaction system was kept under reflux for 6 hours, the total condenser was replaced with a partial condenser and again the temperature was increased and while methanol byproduct and condensation water were recovered, the reaction solution temperature was increased to 120° C. for 3 hours. At the time when the temperature reached 120° C., 1.3 g of pyridine was loaded and as it was, the temperature was increased again and while condensation water was recovered, the temperature was increased to 160° C. for 3 hours and the reaction solution was kept at that temperature for 2 hours and cooled to room temperature. As a result, a silane compound Q was obtained. The silane compound Q was a dark brown and highly viscous liquid containing 60.3% of a non-volatile component and when the molecular weight was measured by GPC, the number average molecular weight was 3480 and the weight average molecular weight was 4010. When $^1$H-NMR measurement was carried out, it was found that the ratio of the organic group including an imide skeleton was 30.8% relative to the organic groups connected to the Si atom. The ratio was almost equivalent to the ratio of the charged organic group including an imide skeleton.

Examples 10 and 11 and Reference Example

As performed in Examples 10 to 9 and Comparative Example 1, the silane compounds were subjected to the TGA analysis and the evaluation for the resistance to hydrolysis. Table 2 shows the evaluation results. In Table 2, the evaluation results of the silane compound C used in Example 3 and the silane compound PPSQ-H in Comparative Example 1 are also shown for comparison. The ratio in Table 2 shows a ratio of the organic group containing an imide skeleton relative to the organic groups connected to the Si atom.

TABLE 2

|  | Example 3 | Example 10 | Example 11 | Reference Example | Comparative Example 1 |
|---|---|---|---|---|---|
| Silane compound | C | N | P | Q | PPSQ-H |
| Proportion | 100% | 69.7% | 50.3% | 30.8% | 0% |
| TGA 5% weight loss temperature | 441° C. | 453° C. | 430° C. | 393° C. | 383° C. |
| Resistance to hydrolysis | Good | Good | Good | Bad | Good | acetate in a manner that the equivalent ratio was adjusted to be 1.0 and next, triphenylphosphine was added as a curing catalyst and further propylene glycol methyl ether acetate was additionally added to adjust the non-volatile component concentration to be 60% to obtain resin compositions A to H. The silane compound content in the solid matter and curing catalyst content ratio were adjusted to be 35% by weight and 1.0% by weight, respectively, in the total amount of the solid matter.

Each composition was applied to a PTFE film (trade name: Aflex, manufactured by Asahi Glass Co., Ltd.; film thickness 50 μm) so as to be a wet coating thickness of 200 μm and thereafter dried at 80° C. for 5 minutes in air atmosphere and at 110° C. for 3 minutes in air atmosphere and cured at 180° C. for 2 hours in air atmosphere by an oven to obtained cured articles.

The appearance and touch of each obtained film were confirmed and TGA analysis of the film was carried out. The analysis conditions were same as those of the TGA analysis for the silane compounds. The weight loss of the film was investigated before and after each obtained film was left in an oven at 220° C. for 100 hours in air atmosphere.

TABLE 3

|  | Example 12 | Example 13 | Example 14 | Example 15 | Example 16 | Example 17 | Comparative Example 2 | Comparative Example 3 |
|---|---|---|---|---|---|---|---|---|
| Sample name | Resin composition A | Resin composition B | Resin composition C | Resin composition D | Resin composition E | Resin composition F | Resin composition G | Resin composition H |
| Silane compound | A | B | C | D | J | K | PPSQ-H | No added |
| Film appearance | Dark brown, transparent | Dark brown, transparent | Yellow, transparent | Yellow, transparent | Light yellow, opaque | Light yellow, opaque | White turbid | Yellow, transparent |
| Film touch | Flexible | Flexible | Flexible | Flexible | Flexible | Flexible | Very fragile | Fragile |
| TGA 5% weight loss temperature | 421° C. | 428° C. | 419° C. | 405° C. | 373° C. | 360° C. | 352° C. | 335° C. |
| Weight loss ratio at 220° C. | 0.15% | 0.08% | 0.18% | 0.21% | 2.5% | 1.8% | 6.8% | 10.5% |

As shown in Table 2, if the ratio of the organic group containing an imide skeleton relative to the organic groups connected to the Si atom was 50% or more, the TGA 5% weight loss temperature was 400° C. or more and an excellent heat resistance was exhibited, and also an excellent resistance to hydrolysis was exhibited. That is, it was found that if the ratio of the organic group containing an imide skeleton was 70% or more (69.4 to 70.4%), the compound exhibited characteristics excellent in both of the heat resistance and the resistance to hydrolysis. If the ratio of the organic group containing an imide skeleton was about 70%, the compound exhibited the most excellent characteristics in both of the heat resistance and the resistance to hydrolysis. If the ratio thereof was less than 50% as in Reference Example, the balance between the resistance to hydrolysis and the heat resistance was deteriorated in comparison to Examples 10 and 11.

Examples 12 to 17 and Comparative Examples 2 and 3

<Evaluation of Heat Resistance of Resin Compositions>

The silane compounds A to D, J, K and PPSQ-H were dissolved in a resin mixed solution obtained by mixing and dissolving cresol-novolak type epoxy resin (trade name: EOCN 1020-65, manufactured by Nippon Kayaku Co., Ltd.; epoxy equivalent 195 g/mol), phenolaralkyl resin (trade name: HE100C-10, manufactured by Air-Water, hydroxyl equivalent 118 g/mol) in propylene glycol methyl ether As shown in Table 3, similarly to a conventional epoxy resin composition, the cured film of Comparative Example 3 in which no silane compound was added had properties of yellow, transparent and fragile, and the film of Comparative Example 2 in which polyphenylsilsesquioxane was added was opaque and the film itself was more fragile than the film with no addition. On the other hand, films obtained from the resin compositions containing the silane compounds within the scope of the invention were dark colored while keeping the transparency and improved in the flexibility. The films produced using the resin compositions containing the silane compounds J and K were opaque, but had improved flexibility.

With respect to the heat resistance, the films of Comparative Examples 2 and 3 had TAG 5% weight loss temperature not higher than 400° C. and significant weight, loss ratio, 5% or higher, at 220° C. and the addition effect of the silane compound was slight, whereas the films of Examples 12 to 15 had TAG 5% weight loss temperature of 400° C. or higher and also low weight loss ratio not higher than 0.3% by weight at 220° C. and thus showed excellent heat resistance. In addition, the films of Examples 16 and 17 had TAG 5% weight loss temperature of 350° C. or higher and also low weight loss ratio not higher than 2.5% by weight at 220° C. and thus showed excellent heat resistance.

Examples 18 to 25 and Comparative Examples 4 and 5

<Evaluation of Heat Resistance of Resin Compositions>

After the above-mentioned silane compounds B, C, and E were dry-blended with three kind epoxy resins in amounts described in Table 4, a phenol type curing agent, a maleimide compound, fused silica, and an epoxy curing promoting agent, the blended mixtures were melted and kneaded by a hot roll kneader to obtain compounds. The kneading conditions were adjusted to be roll surface temperature at 70° C., roll fastening pressure at 0.5 MPa, and kneading time for 10 minutes. The obtained compounds were transferred to the inside of a plate type mold (cavity distance: 1 mm) to press-mold the compounds at 180° C. and 8 MPa for 3 minutes and then left at 180° C. for 7 hours in nitrogen gas circulating condition to obtain molded bodies with thickness of 1 mm.

Each molded body was cut into 10 mm×10 mm×1 mm and left at 220° C. for 1000 hours in air circulating condition to investigate weight loss ratio before and after being left.

The results are shown in Table 4. In Table 4, the addition amounts were all shown as parts by weight.

tive Examples 4 and 5 and the weight loss after 1000 hours-standstill was around 2%, whereas the silane compounds of the invention were added in Examples 18 to 21 to result in weight loss very slight as 0.1 to 0.5%. Further, maleimide compounds were added in Examples 22 to 25 and the weight loss was further lowered by one-digit to 0.02 to 0.08%.

Examples 26 to 29, Comparative Example 6

<Measurement of Silanol Group Concentration of Silane Compounds>

After being loaded with 1.0 g of each of the above-mentioned silane compounds, 5.0 g of chloroform, and 0.1 g of hexamethyldisilazane, a 10 ml vial container made of glass was immersed in a shaker bath. Thereafter, the mixture was dried at 110° C. in a vacuum oven to carryout trimethylsilylation of the silanol group. The obtained sample was subjected to $^1$H-NMR and the silanol group concentration as [molar number of Si—OH bond]/[molar number of Si—O bond] in the silane compounds F to I was calculated from the ratio of the integrated values of trimethylsilyl group and α-methylene group. The results are shown in Table 5.

TABLE 4

| | Example 18 | Example 19 | Example 20 | Example 21 | Example 22 | Example 23 | Example 24 | Example 25 | Comparative Example 4 | Comparative Example 5 |
|---|---|---|---|---|---|---|---|---|---|---|
| Epoxy resin | 7.40 | 7.75 | 5.47 | 3.42 | 5.01 | 4.52 | 4.55 | 4.33 | 6.26 | 4.00 |
| Phenol curing agent | 8.77 | 9.19 | 6.48 | 4.06 | 5.94 | 5.36 | 5.40 | 5.13 | 7.42 | 4.74 |
| Silane compound B | 8.71 | 2.99 | — | — | — | — | — | — | — | — |
| Silane compound C | — | — | 7.97 | — | 4.70 | — | 4.27 | — | — | — |
| Silane compound E | — | — | — | 7.48 | — | 6.59 | — | 5.10 | — | — |
| Comparative silane compound | — | — | — | — | — | — | — | — | 11.19 | 3.74 |
| Maleimide compound (I) | — | — | — | — | 4.27 | 3.62 | — | — | — | — |
| Maleimide compound (II) | — | — | — | — | — | — | 5.70 | 5.36 | — | 4.96 |
| Fused silica | 74.63 | 79.68 | 79.68 | 84.75 | 79.68 | 80.36 | 79.68 | 79.68 | 74.63 | 82.21 |
| Curing promoting agent | 0.50 | 0.40 | 0.40 | 0.30 | 0.40 | 0.40 | 0.40 | 0.40 | 0.50 | 0.35 |
| Weight loss (%) after kept at 220° C. × 1000 hours | 0.13 | 0.21 | 0.43 | 0.48 | 0.08 | 0.05 | 0.03 | 0.02 | 2.38 | 1.93 |

The reagents used in Table 4 were shown below.
Epoxy resin: trisphenol type epoxy resin (trade name: EPPN 501H, manufactured by Nippon Kayaku Co., Ltd.)
Phenol curing agent: biphenyl type phenol aralkyl resin (trade name: MEH 7851SS, manufactured by Nippon Kayaku Co., Ltd.)
Comparative silane compound: polyphenylsilsesquioxane (trade name: PPSQ-H, manufactured by Konishi Kagaku Kogyo)
Maleimide compound (I): 4,4'-diphenylmethanebismaleimide (trade name: BMI 1000, manufactured by Daiwa Kasei K.K.)
Maleimide compound (II): bisphenol A diphenyl ether bismaleimide (trade name: BMI 4000, manufactured by Daiwa Kasei K.K.)
Fused silica: trade name: SO-E2, manufactured by Admatechs Co., Ltd.
Curing promoting agent: triphenylphosphine As shown in Table 4, conventionally known polyphenylsilsesquioxanes were added to the compositions of Compara- <Evaluation of Moisture Absorption of Resin Compositions>

After cresol novolak type epoxy resin (trade name: EOCN 1020-65, manufactured by Nippon Kayaku Co., Ltd.; epoxy equivalent 195 g/mol) and phenolaralkyl resin (trade name: XLC-4L, manufactured by Mitsui Chemicals, Inc.; hydroxyl equivalent 168 g/mol) were weighted to give equivalent 1.0 and total weight 10 g and loaded to a 100 ml of separable flask, 2.5 g each of the silane compounds F to I and commercialized polyphenylsilsesquioxane (trade name: PPSQ-H, manufactured by Konishi Kagaku Kogyo) were dissolved and next as a curing catalyst, triphenylphosphine was added and after being melted at 100° C. for 5 minutes, each mixture was poured in an injection frame made of glass having a 1 mm-thick spacer and left still at 180° C. for 7 hours to obtain a cured resin plate.

The cured resin plate was cut into a 20 mm square and left in condition of saturated steam at 121° C. and 0.2 Mpa for 24 hours and the moisture absorption property was evaluated based on the weight alteration before and after being left. The results are shown in Table 5

TABLE 5

|  |  | Example 26 | Example 27 | Example 28 | Example 29 | Comparative Example 6 |
|---|---|---|---|---|---|---|
|  | Sample name | Silane compound F | Silane compound G | Silane compound H | Silane compound I | PPSQ-H |
|  | Silanol concentration in silane compound | 4.0% | 3.8% | 0 | 0 | 0.6% |
| Resin composition | Appearance after moisture absorption | Transparent | Transparent | Transparent | Transparent | White turbid |
|  | Moisture absorption ratio of cured product | 2.7% | 3.1% | 2.1% | 2.5% | 3.8% |

As shown in Table 5, although having a higher silanol group concentration than that of Comparative Example, the silane compounds F to I of the invention had high affinity with the matrix resin even after the moisture absorption treatment and low moisture absorption. The silane compounds H and I were found having no silanol and show the lowest moisture absorption. That is, a comparison between Examples 26 and 27, and Examples 28 and 29 showed that the films were more excellent in the resistance to moisture absorption if the silanol group concentration is small.

Examples 30 to 35 and Comparative Examples 7 to 12

These silane compounds L and M were dissolved at the ratios shown in Table 6 in toluene in a manner that the non-volatile component concentration was adjusted to be 70% by weight to prepare resin compositions. The materials used were as follows.

silane compound L: poly{γ-(octenylsuccinimido)propylsilsesquioxane}
silane compound M: poly{γ-(dodecenylsuccinimido)propylsilsesquioxane}
commercialized silane compound: polyphenylsilsesquioxane (trade name: PPSQ-H, manufactured by Konishi Kagaku Kogyo)
polyolefin 1: hydroxyl-terminated polyolefin (trade name: Epol, manufactured by Idemitsu Petrochemical Co., Ltd.)
polyolefin 2: carboxyl-terminated polyolefin (trade name: Kuraprene LIR410, manufactured by Kuraray Co., Ltd.)
polyolefin 3: epoxy-terminated polyolefin (trade name: Denalex R-45EPT, manufactured by Nagase Chemtech Ltd.)
curing agent 1: hexamethylene diisocyanate
curing agent 2: 1,6-hexanediol diglycidyl ether
curing agent 3: amino-terminated polypropylene glycol (trade name: Jeffamine D400, manufactured by Nitsui Fine Chemicals Inc.)
curing promoting agent 1: dibutyltin dilaurate
curing promoting agent 2: triphenylphosphine <Adhesiveness Evaluation>
After 4-inch Si wafers were immersed in acetone and washed by ultrasonic treatment, Si wafers were coated with the above-mentioned resin compositions in a thickness of 50 μm on the basis of solid matter and dried in condition of 80° C.×30 minutes in an oven and further after being transferred to an inert gas oven in nitrogen atmosphere, the wafers were treated condition of 130° C.×30 minutes+condition of 180° C.×1 hour to obtain cured film-bearing wafers. Using the wafers, a cross-cut adhesion test was carried out to evaluate the adhesiveness of the cured films to Si. The evaluation results are shown in Table 6.

<Moisture Adsorption Evaluation of Resin Compositions>
The above-mentioned silane compounds E and F and commercialized polyphenylsilsesquioxane (trade name: PPSQ-H, manufactured by Konishi Kagaku Kogyo) were dissolved at the ratios shown in Table 6 in toluene in a manner that the non-volatile component concentration was adjusted to be 70% by weight to prepare resin compositions. A PET film was coated with the above-mentioned resin compositions in a thickness of 50 μm on the basis of solid matter and dried in condition of 80° C.×30 minutes in an oven and further after being transferred to an inert gas oven in nitrogen atmosphere, the PET film was treated condition of 130° C.×30 minutes+condition of 180° C.×1 hour and the PET film was removed to obtain cured films.

The cured films were cut in 20 mm square and left in condition of at 121° C. and 0.2 MPa for 24 hours in saturated steam. The moisture absorption property was evaluated based on the weight alteration ratio before and after the standstill test. The evaluation results are shown in Table 6.

<Heat Resistance Valuation>
Using the same samples subjected to the moisture absorption evaluation, TG-DTA analysis was carried out. The analysis conditions were adjusted to be air circulation of 200 mL/min and heating speed of 10° C./min. The evaluation results are shown in Table 6.

TABLE 6

|  | Example | | | | | | Comparative Example | | | | | |
|---|---|---|---|---|---|---|---|---|---|---|---|---|
|  | 30 | 31 | 32 | 33 | 34 | 35 | 7 | 8 | 9 | 10 | 11 | 12 |
| Silane compound L | 45 | — | 40 | — | 60 | — | — | — | — | — | — | — |
| Silane compound M | — | 35 | — | 50 | — | 45 | — | — | — | — | — | — |
| Commercially available silane compound | — | — | — | — | — | — | — | — | — | 50 | 50 | 50 |
| Polyolefin 1 | 46.5 | 54.9 | — | — | — | — | 84.5 | — | — | 42.3 | — | — |
| Polyolefin 2 | — | — | 56.9 | 47.5 | — | — | — | 94.9 | — | — | 47.5 | — |
| Polyolefin 3 | — | — | — | — | 34.3 | 47.1 | — | — | 85.7 | — | — | 42.9 |
| Curing agent 1 | 8.5 | 10.1 | — | — | — | — | 15.5 | — | — | 7.7 | — | — |
| Curing agent 2 | — | — | 3.1 | 2.5 | — | — | — | 5.1 | — | — | 2.5 | — |
| Curing agent 3 | — | — | — | — | 5.7 | 7.9 | — | — | 14.3 | — | — | 7.1 |
| Curing promoting agent 1 | 0.3 | 0.3 | — | — | — | — | 0.3 | — | — | 0.3 | — | — |

TABLE 6-continued

|  |  | Example | | | | | | Comparative Example | | | | | |
| --- | --- | --- | --- | --- | --- | --- | --- | --- | --- | --- | --- | --- |
|  |  | 30 | 31 | 32 | 33 | 34 | 35 | 7 | 8 | 9 | 10 | 11 | 12 |
| Curing promoting agent 2 | | — | — | 0.3 | 0.3 | — | — | — | 0.3 | — | — | 0.3 | — |
| Adhesiveness | Cross-cut adhesion test | Good | Good | Good | Good | Good | Good | Good | Good | Good | Bad | Bad | Bad |
| Moisture absorption property | Moisture absorption rate (%) | 0.5 | 0.6 | 0.5 | 0.4 | 0.4 | 0.5 | 1.5 | 1.3 | 1.3 | 0.7 | 0.5 | 0.6 |
| Heat resistance | 5% weight loss temperature (° C.) | 351 | 335 | 342 | 360 | 363 | 349 | 270 | 283 | 251 | 350 | 361 | 332 |

As shown in Comparative Examples 7 to 9, although the compositions containing no silane compound were excellent in the adhesion, they have low heat resistance and high moisture absorption as well. In Comparative Examples 10 to 12, the compositions containing the commercialized silane compound, the adhesiveness was decreased although the heat resistance was increased. On the other hand, in Examples 30 to 35, the compositions containing the silane compounds of the present invention, both of the heat resistance and the resistance to moisture absorption were improved simultaneously without decreasing the adhesiveness. As a result, the comparison between the resin compositions containing the silane compounds L and M with the resin compositions containing the PPSQ-M used in Comparative Examples 10 to 12 verifies that a particularly excellent adhesion could be exhibited if the resin compositions were mixed with the polyolefin resin.

<Evaluation of dielectric Characteristic of Resin Composition>

A 100 mL of separable flask equipped with a temperature sensor, a stirrer, and a decompression device was loaded with compounds at proportions shown in the following Table 7. The compounds were melted and mixed at 110° C. with vacuumed at 1 kPa for 5 minutes. The mixture was poured in an injection frame made of glass having a 2 mm-thick spacer and left still at 200° C. for 8 hours in an oven and then demolded to obtain a cured resin plate. The silane compound C produced in Synthesis Example 3 was used.

The cured resin plate was cut into a 30 mm square and measured for dielectric characteristics. With respect to the measurement, the TEM mode coaxial resonator produced by AET Inc. was used; the measuring temperature was 23° C.; and the measuring frequency was 1 GHz or 5 GHz.

TABLE 7

|  |  | Example 36 | Example 37 | Comparative Example 13 |
| --- | --- | --- | --- | --- |
| Epoxy compound | | — | 24.8 | 49.6 |
| Phenol compound | | — | 25.2 | 50.4 |
| Silane compound C | | 65.6 | 39.6 | — |
| Maleimide Compound | | 34.4 | 11.4 | — |
| 1 GHz | Relative dielectric constant | 3.09 | 3.03 | 3.47 |
|  | Dielectric loss tangent | 0.0072 | 0.0088 | 0.0215 |
| 5 GHz | Relative dielectric constant | 3.08 | 3.00 | 3.33 |
|  | Dielectric loss tangent | 0.0074 | 0.0090 | 0.0273 |

The compounds in Table 7 are mentioned below. Epoxy compound: Phenol novolac epoxy resin (trade name "EOCN1020-65", produced by NIPPON KAYAKU Co., Ltd.) Phenol compound: Biphenylene phenol aralkyl resin (trade name "MEH-7851SS", produced by Showa Kasei Kogyo Co., Ltd.) Maleimide compound: m-phenylene bismaleimide (produced by Wako Pure Chemical Industries, Ltd.)

As shown in Table 7, the resin compositions including the silane compounds in Examples 36 and 37 had a more reduced dielectric constant in comparison to the composition not including the silane compound in Comparative Example 13. Particularly, the effect of reducing the dielectric loss tangent was remarkable. As the mixing ratio of the silane compound was increased, the effect of reducing the dielectric loss tangent was remarkably observed. Such a result shows that the resin compositions including the above-mentioned silane compound and the organic resin have excellent characteristics as a resin composition for low dielectric materials.

Evaluation of Resin Composition for Bond Magnets

Synthesis Example 18

A 300 mL of four-necked flask equipped with a stirrer, a temperature sensor, and a total condenser was loaded with 35.1 g of diglyme previously dried by molecular sieve and 30.8 g of 3-aminopropyltrimethoxysilane and while being stirred, the mixture was heated to 100° C. in condition of circulating dried nitrogen to remove water in the system. Then, while the reaction solution was maintained at 100° C., 28.2 g of 5-norbornene-2,3-dicarboxylic anhydride was loaded in a tetrameric manner for 30 minutes. In 9 hours after completion of the loading, it was confirmed by high performance liquid chromatography that the 5-norbornene-2,3-dicarboxylic anhydride was completely consumed. Successively, 9.3 g of deionized water was collectively loaded and after the temperature was increased to reflux methanol byproduct by the total condenser and the reaction system was kept at 95° C. for 10 hours, the total condenser was replaced with a partial condenser and again the temperature was increased and while methanol byproduct and condensation water were recovered, the reaction solution temperature was increased to 120° C. for 3 hours. At the time when the temperature reached 120° C., 1.4 g of pyridine was loaded and as it was, the temperature was increased again and while condensation water was recovered, the temperature was increased to 160° C. for 3 hours and the reaction solution was kept at that temperature for 2 hours and cooled to room temperature. The reaction solution a dark brown and highly viscous liquid containing 58.2% of a non-volatile component and when the molecular weight was measured by GPC, the number average molecular weight was 2340 and the weight average molecular weight was 2570. When $^1$H-NMR and $^{13}$C-NMR measurements were carried out, it was found that this reaction solution was a polysiloxane compound containing γ(5-norbornene-2,3-imide)propyl group. In a 100 mL of four-necked flask equipped with a stirrer, a temperature sensor, and a total condenser, 24.0 g of this reaction solution and 26.0 g of cresol novolac epoxy resin (trade name "EOCN-1020-65", epoxy equivalent: 210 g/mol, produced by NIPPON KAYAKU Co., Ltd.) were mixed at 120° C. The mixture was cooled after the diglyme was evaporated. As a result, a resin composition I that was a light yellow transparent solid was obtained. The yield was 38.3 g and the epoxy equivalent was 323 g/mol.

Synthesis Example 19

A resin composition J that was a brownish solid was obtained in the same manner as in Synthesis Example 18 except that phenol aralkyl resin (trade name "MEH-7851-SS", produced by MEIWA PLASTIC INDUSTRIES, LTD.) was used instead of the cresol novolac epoxy resin (trade name "EOCN-1020-65", epoxy equivalent: 210 g/mol, produced by NIPPON KAYAKU Co., Ltd.). The yield was 38.3 g and the hydroxyl group equivalent was 312 g/mol.

Synthesis Example 20

A 1 L of four-necked flask equipped with a gas inlet, a Dean-Stark trap, and a stirring bar was loaded with 432.9 g of phenol, 172.2 g of benzoguanamine, and 179.2 g of 37% formaldehyde solution and while the white turbid solution was stirred at 60° C. in condition of circulating nitrogen, 9 mL of ammonia water was added to the solution. After the reaction solution became transparent, the solution was heated to 80° C. Under stirring, the reaction solution was maintained for 4 hours and then heated again. The reaction solution was heated to 180° C. while generated water which started to be distilled around at 100° C. was collected into the trap. After residual phenol was distilled in vacuum, the solution was cooled to obtain a resin composition K that was a milky-white solid. The yield was 406 g, the thermalsoftening temperature was 92° C., the hydroxyl group value was 170 g/mol, and the inorganic compound content was 0%.

Synthesis Example 21

A 2 L of four-necked flask equipped with a gas inlet, a Dean-Stark trap, and a stirring bar Was loaded with 302.6 g of p-xylylene glycol, 687.0 g of phenol, and 12.6 g of p-toluenesulfonic acid. Then, the mixture was heated in condition of circulating nitrogen. Around at 115° C., water started to be generated, and while the water was collected into the trap, the solution was heated to 150° C. and maintained for 6 hours. When 79 g of water was collected; generation of water was finished. Further, the temperature was increased again in condition of circulating nitrogen. The solution was kept stirring until the temperature reached 180° C. After unreacted phenol was distilled in vacuum, the solution was cooled to obtain a brownish semisolid resin composition L. The yield was 491 g, the thermalsoftening temperature was 43° C., the hydroxyl group value was 155 g/mol, and the inorganic compound content was 0%.

Synthesis Example 22

A 500 mL of four-necked flask equipped with a gas inlet, a Dean-Stark trap, and a stirring bar was loaded with 168 g of cresol novolac epoxy resin (trade name "EOCN-1020-65", epoxy equivalent: 210 g/mol, produced by NIPPON KAYAKU Co., Ltd. and 122.3 g of ethylene glycol diacrylate. After the mixture was stirred at 80° C. until dissolution was completed, 0.011 g of 4-hydroxy-2,2,6,6-tetramethylpiperidine-1-oxyl and 1.01 g of tetraphenyl phosphonium bromide were loaded and in condition of circulating air, 59.1 g of acrylic acid was added dropwise into the mixture at 110° C. for 2 hours. After the loading, the reaction solution was stirred at 115° C. for 6 hours in condition of circulating air. After it was confirmed that the acid value of the reaction solution was 7 mg KOH/g or less, the reaction solution was cooled to 40° C. to obtain a light yellow liquid resin composition M. The yield was 343 g, the inorganic compound content was 0%, and the non-volatile matter content was 64%.

Mixing of magnetic powders with resin compositions I to M and preparation of samples for physical property evaluation Commercially available SmFeN anisotropic magnetic powders (product of SUMITOMO METAL MINING CO., LTD.) and the above-mentioned resin compositions I to M, a curing catalyst, and a silane coupling agent were mixed by a hot roll kneader. The mixing ratio by weight of each component is as shown in Table 8. The kneading was performed at 80° C. for 5 minutes at a roll pressure of 0.5 MPa. The obtained compound was molded into a flat plate with a thickness of 1 mm using a pressure molding machine. Then, from the flat plate, a sample for evaluation was prepared using a freezing-crushing machine.

Heat Resistance of Molded Products

With respect to the evaluation of the heat resistance, the above-mentioned samples for evaluation were heated in condition of circulating air using TG-DTA (product name TG-DTA 2000SR, produced by Bruker Co., Ltd.) to be measured for a ratio of weight change. The measuring temperatures were 150° C., 180° C., and 200° C. The measuring time was 24 hours. The sampling interval was 180 seconds. Table 8 shows the results.

TABLE 8

|  |  | Example 38 | Example 39 | Example 40 | Example 41 |
|---|---|---|---|---|---|
| Magnetic powder | | 97.00 | 97.00 | 97.00 | 97.00 |
| Resin composition I | | 1.53 | — | — | — |
| Resin composition J | | 1.47 | — | — | — |
| Resin composition K | | — | 1.40 | — | — |
| Resin composition L | | — | — | 1.27 | — |
| Resin composition M | | — | — | — | 3.00 |
| YX4000H | | — | 1.60 | — | — |
| NC7000 | | — | — | 1.73 | — |
| TPP | | 0.06 | 0.06 | 0.06 | — |
| PERBUTYL O | | — | — | — | 0.06 |
| Rate of weight change (%) | 150° C. | 0.13 | 0.21 | 0.17 | 0.14 |
|  | 180° C. | 0.22 | 0.67 | 0.73 | 0.81 |
|  | 200° C. | 0.31 | 1.13 | 1.38 | 1.76 |

Experiment Results

In the molded products in Examples 38 to 41, the rate of weight change was almost the same when the molded products were heated at about 150° C. Therefore, the molded products in Examples 38 to 41 seemed to have almost the same oxidation resistance. However, if the molded products were heated at higher temperatures of 180° C. and 200° C., in Examples 39 to 41, the rate of weight change was increased and therefore the oxidation resistance seemed to be deteriorated. In Example 38, the rate of weight change was moderately increased and the oxidation resistance was slightly reduced.

The invention claimed is:

1. A siloxane compound having a siloxane bond and an imido bond,
wherein the siloxane compound comprises a structure unit formed by connecting at least one organic skeleton having an imido bond to a silicon atom forming a siloxane bond,
wherein the siloxane compound is defined by the following average composition formula:

$X_a Y_b Z_c SiO_d$ wherein X in the average composition formula is defined by the following formula (5):

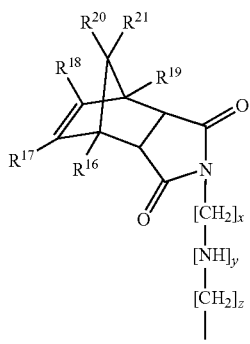

(5)

in the formula,
$R^{16}$ to $R^{21}$ may be same or different and independently denote at least one selected from the group consisting of hydrogen atom, alkyl group, halogen atom, or aromatic groups;
x and z may be same or different and independently denote an integer of 0 or higher and 5 or lower; and
y is 0 or 1;
Z may be same or different and denotes an organic group having no imido bond;
Y is a hydroxyl group or an OR group, in which R is an alkyl group having 1 to 8 carbon atom(s);
a is 1;
b is 0 or a numeral less than 3;
c is 0;
d is a numeral less than 2 but not 0; and
a+b+c+2d=4.

2. The siloxane compound according to claim 1, wherein x+z is 3, and y is 0.

3. The siloxane compound according to claim 1, wherein the number of bonds between a silicon atom to which X is connected and an oxygen atom is 3.

4. The siloxane compound according to claim 1, wherein the number of bonds between a silicon atom forming the siloxane bond and an oxygen atom is 3.

5. The siloxane compound according to claim 1, wherein a ratio of a silanol group amount, calculated by the following formula ($\alpha$), is 0.1 or less; molar number of (Si—OH bond]/[molar number of Si—O bond] ($\alpha$).

6. The siloxane compound according to claim 1, wherein the siloxane compound has a cage-like molecular structure.

7. The siloxane compound according to claim 1, wherein the siloxane skeleton of the siloxane compound is defined as $(SiO_m)_n$, wherein m is 1.5, and n denotes the polymerization degree and is 2 to 1000.

* * * * *